(12) United States Patent
Madsen et al.

(10) Patent No.: US 9,353,211 B2
(45) Date of Patent: May 31, 2016

(54) POLYMERIC PHOTOINITIATORS AND PHOTOINITIATOR MONOMERS

(71) Applicant: Coloplast A/S, Humlebaek (DK)

(72) Inventors: Niels Joergen Madsen, Alleroed (DK); Petr Sehnal, York (GB); David George Anderson, York (GB); Bo Rud Nielsen, Alleroed (DK)

(73) Assignee: Coloplast A/S, Humlebaek (DK)

( * ) Notice: Subject to any disclaimer, the term of this patent is extended or adjusted under 35 U.S.C. 154(b) by 0 days.

(21) Appl. No.: 14/401,127

(22) PCT Filed: May 14, 2013

(86) PCT No.: PCT/DK2013/050145
§ 371 (c)(1),
(2) Date: Nov. 14, 2014

(87) PCT Pub. No.: WO2013/170859
PCT Pub. Date: Nov. 21, 2013

(65) Prior Publication Data
US 2015/0166716 A1  Jun. 18, 2015

(30) Foreign Application Priority Data

May 16, 2012  (DK) ................................. 2012 70263
Jun. 12, 2012  (DK) ................................. 2012 70317
Jun. 12, 2012  (DK) ................................. 2012 70318

(51) Int. Cl.
| | | |
|---|---|---|
| *C08F 2/46* | (2006.01) | |
| *C08F 2/50* | (2006.01) | |
| *C08G 61/04* | (2006.01) | |
| *C08G 18/66* | (2006.01) | |
| *C08G 18/48* | (2006.01) | |
| *C08G 18/73* | (2006.01) | |
| *C08G 18/32* | (2006.01) | |
| *C07C 217/54* | (2006.01) | |
| *C08F 120/18* | (2006.01) | |
| *C08G 18/72* | (2006.01) | |
| *C08J 3/24* | (2006.01) | |
| *C08J 3/28* | (2006.01) | |

(52) U.S. Cl.
CPC .......... *C08G 18/6674* (2013.01); *C07C 217/54* (2013.01); *C08F 2/50* (2013.01); *C08F 120/18* (2013.01); *C08G 18/3215* (2013.01); *C08G 18/4833* (2013.01); *C08G 18/72* (2013.01); *C08G 18/73* (2013.01); *C08J 3/24* (2013.01); *C08J 3/28* (2013.01); *C08J 2375/08* (2013.01)

(58) Field of Classification Search
CPC ............... C08G 18/6674; C08G 18/72; C08G 18/4833; C08G 18/3215; C08G 18/73; C08J 3/24; C08J 2375/08; C08J 3/28; C07C 217/54; C08F 120/18; C08F 2/50

USPC ............. 522/35, 33, 6, 71, 189, 184, 1; 520/1
See application file for complete search history.

(56) References Cited

U.S. PATENT DOCUMENTS

| | | | |
|---|---|---|---|
| 4,602,097 | A | 7/1986 | Curtis |
| 4,861,916 | A | 8/1989 | Kohler et al. |
| 4,992,547 | A | 2/1991 | Berner et al. |
| 6,031,044 | A | 2/2000 | Kokel et al. |
| 2007/0078246 | A1 | 4/2007 | Herr et al. |
| 2010/0049146 | A1 | 2/2010 | Nielsen et al. |

FOREIGN PATENT DOCUMENTS

| | | |
|---|---|---|
| CN | 1817914 A | 8/2006 |
| CN | 101012180 A | 8/2007 |
| CN | 101029095 A | 9/2007 |
| CN | 101495162 A | 7/2009 |
| EP | 0627452 A1 | 12/1994 |
| EP | 1676870 A1 | 7/2006 |
| EP | 2130817 A1 | 12/2009 |
| EP | 2199273 A1 | 6/2010 |
| GB | 2320027 A1 | 6/1998 |
| JP | H10182781 | 7/1998 |
| WO | 9633156 A1 | 10/1996 |
| WO | 9749664 A1 | 12/1997 |
| WO | 9833764 A1 | 8/1998 |
| WO | 9851759 A1 | 11/1998 |
| WO | 03033492 A1 | 4/2003 |
| WO | 2004009651 A1 | 1/2004 |

(Continued)

OTHER PUBLICATIONS

Mukundan et al. "A photocrosslinkable melt processible acrylonitrile terpolymer as carbon fiber precursor." Polymer 47 (2006), pp. 4163-4171.

Naskar et al. "UV assisted stabilization routes for carbon fiber precursors produced from melt-processible polyacrylonitrile terpolymer." Carbon 43 (2005), pp. 1065-1072.

Wei et al. "Novel Polymeric, Thio-Containing Photoinitiator Comprising In-Chain Benzophenone and an Amine Coinitiator or Photopolyrnerization." Journal of Polymer Science: Part A: Polymer Chemistry, vol. 45, pp. 576-587 (2007).

Wei et al: ""Novel PU-type polymeric photoinitiator comprising side-chain benzophenone and coinitiator amine for photopolymerization of PU acrylate"", Polymers for advanced technologies 2008 John Wiley and sons ltd; the Atrium gb, vol. 19, No. 12, 2008, pp. 1763-1770.

(Continued)

*Primary Examiner* — Ling Choi
*Assistant Examiner* — Jessica E Whiteley
(74) *Attorney, Agent, or Firm* — Coloplast Corp., Coloplast A/S; Nick Baumann

(57) ABSTRACT

The present invention provides polymeric photoinitiators being co-polymers of photoinitiator monomers and at least one further monomer, as well as the photoinitiator monomers being intermediates in the preparation of such polymeric photoinitiators. Additionally there is provided polyacrylate obtained by radical polymerization of at least one acrylate monomer (Ac) in the presence of such polymeric photoinitiators. In the photoinitiator monomers and polymeric photoinitiators, a photoinitiator moiety and a tertiary amine are incorporated into the photoinitiator structure.

38 Claims, 1 Drawing Sheet

(56) References Cited

FOREIGN PATENT DOCUMENTS

| WO | 2007/092935 | * | 8/2007 |
| WO | 2007092935 A1 | | 8/2007 |
| WO | 2008070737 A1 | | 6/2008 |
| WO | 2009060235 A1 | | 5/2009 |
| WO | 2010063612 A1 | | 6/2010 |
| WO | 2010069758 A1 | | 6/2010 |
| WO | 2010072479 A1 | | 7/2010 |
| WO | 2011160641 A2 | | 12/2011 |
| WO | 2012062333 A1 | | 5/2012 |

OTHER PUBLICATIONS

J. P. Griffiths et al: "'Surface functional polymers by post-polymerization modification, release and regeneration of hydrogen peroxide and bacterial activity'", Langmuir, vol. 26, Jul. 30, 2010, pp. 14142-14153.

J. Wei, H. Wang, X. Jiang, J. Yin, Macromolecules, 40 (2007), 2344-2351.

J. Wei, F. Liu Macromolecules, 42 (2009), 5486-5491.

T. Corrales, F. Catalina, C. Peinado, N.S. Allen J. Polym. Sci., Part A: Polym.Chem., 159 (2003), 103-114.

A. Gilbert, J. Baggott: "Essentials of Molecular Photochemistry", Blackwell, London, 1991.

M.L Gould, S. Narayan-Sarathy, T.E. Hammond, and R.B. Fechter from Ashland Specialty Chemical, USA (2005): "Novel Self-Initiating UV-Curable Resins: Generation Three", Proceedings from RadTech Europe 05, Barcelona, Spain, Oct. 18-20, 2005, vol. 1, p. 245-251, Vincentz.

C.K. Nguyen, W. Kuang, and C.A. Brady from Albemarle Corporation and Brady Associates LLC, both USA (2003): "Maleimide Reactive Oligomers", Proceedings from RadTech Europe 03, Berlin, Germany, Nov. 3-5, 2003, vol. 1, p. 589-94, Vincentz.

J.P. Fouassier: "Excited-State Reactivity in Radical Polymerisation Photo-initiators", Ch. 1, pp. 1-61, in "Radiation curing in Polymer Science and technology", vol. II ("Photo-initiatingSystems"), ed. by J.P. Fouassier and J.F. Rabek, Elsevier, London, 1993.

S. Kopeinig and R. Liska from Vienna University of Technology, Austria (2005): "FurtherCovalently Bonded Photoinitiators", Proceedings from RadTech Europe 05, Barcelona, Spain, 15 Oct. 18-20, 2005, vol. 2, p. 375-81, Vincentz.

Left blank on purpose.

J. Med. Chem. 2001, 3810-3820.

J. Med. Chem. 1998, 3976-3986.

J. Med. Chem. 1989, 105-118.

Tetrahedron 2009, 4429-4439.

J. Phys. Org. Chem. 2001, 14, 247-255.

J. Med. Chem. 1991, 34, 1552-1560.

Polymer Synthesis: Theory and Practice, Fundamentals, Methods, Experiments, 4th edition, Springer, 319-324, 2005.

Peinado et al: Synthesis of novel 2-(3'-dialkylaminopropoxy)-thioxanthone derivatives. Photochemistry and evaluation as photoinitiators of butyl acrylate polymerization, European Polymer Journal, Pergamon Press Ltd. Oxford, GB, vol. 28, No. 10, Oct. 1, 1992, pp. 1315-1320.

Jianwen yang et al: "Amine-linked Thioxanthones as water-compatible photoinitiators", Journal of polymer science: Part A: Polymer Chemistry, vol. 36, Jan. 1, 1998, pp. 2563-2570.

Gokhan Temel et al: "'Photopolymerization and photophysical properties of amine linked benzophenone photoinitiator for free radical polymerization'", Journal of Photochemistry and photobiology, A: Chemistry, Elsevier Sequoia, Lausanne, CH, vol. 219, No. 1, Jan. 21, 2011, pp. 26-31.

Scott K. Christensen et al: "Gelation of Copolymers with Pendent Benzophenone Photo-Cross-Linkers", Macromolecules, vol. 45, No. 12, Jun. 26, 2012, pp. 5237-5246.

* cited by examiner

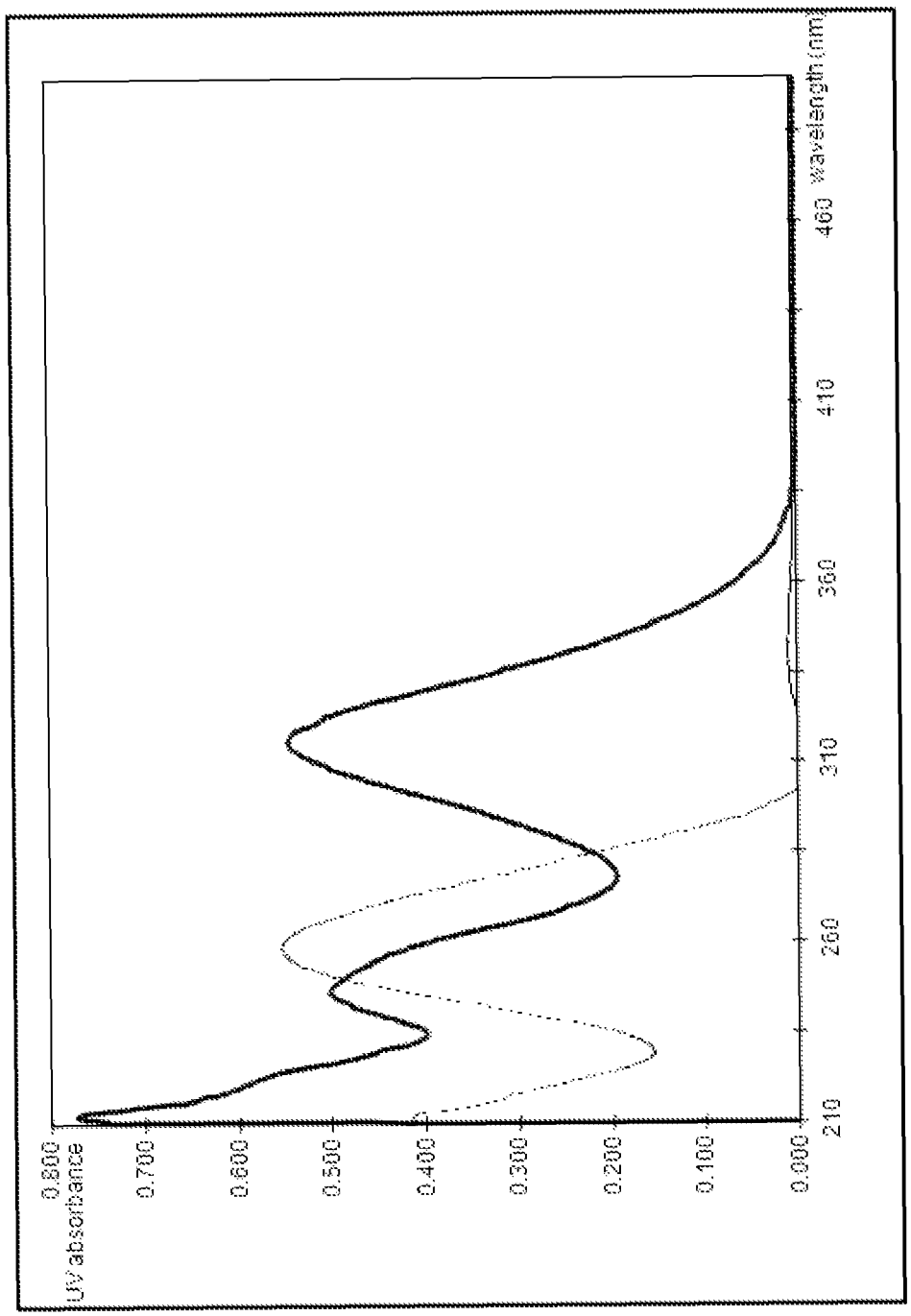

POLYMERIC PHOTOINITIATORS AND PHOTOINITIATOR MONOMERS

FIELD OF THE INVENTION

The present invention relates to polymeric photoinitiators where the photoinitiator moieties are incorporated as pendant groups on the polymeric backbone, as well as photoinitiator monomers being intermediates in the preparation of such polymeric photoinitiators. Additionally the present invention relates to polyacrylates obtained by radical polymerization of at least one acrylate monomer (Ac) in the presence of a polymeric photoinitiator. The intermediate photoinitiator monomers allow for preparation of initial linear photoinitiator polymers due to a branching point with two functional groups. Due to the presence of a tertiary amine the polymeric photoinitiators and the photoinitiator monomers in themselves have an inbuilt catalytic and/or co-reagent functionality.

BACKGROUND OF THE INVENTION

Curing of coatings through ultraviolet (UV) radiation requires efficient methods of initiating the chemical reaction responsible for the curing process. Curing of polymeric material through generation of radical species upon irradiation with UV light is widely used to produce coatings for medical devices. The paint and lacquer industry also makes use of UV-initiated curing of acrylates, where photoinitiators in many cases are employed. These two examples illustrate the diversity of UV curable coatings.

In a UV curing process, a photoinitiator moiety (low molecular weight or polymer-bound) absorbs UV light and undergoes transition to an excited state, which undergoes further processes which result in the formation of free radicals. This stage is known as initiation.

A polymer photocrosslinking process starts out with long linear polymer chains, and the initiation stage proceeds as described above. Through hydrogen abstraction, the free radicals can be transferred from the photoinitiator to an existing polymer backbone. Hereby forming new carbon-carbon bonds via radical recombination between the polymer chains providing a cross-linking of the before linear polymer chain. Such photoinitiators can be either of low molecular weight or bound in a polymer backbone.

One advantage of this photocrosslinking method is that a linear polymer has considerably different properties than the same type of polymer being cross-linked. The linear polymer may for example be soluble and can then be used in different production processes; it may be e.g. applied on medical devices by spraying or dip coating. The photocrosslinking process may then be initiated afterwards, cross-linking the polymer attaching it to the surface it is applied upon. It will neither dissolve nor melt.

Alternatively, the free radicals formed in the initiation stage may react with unsaturated monomers. This is then called a radical propagation stage. As the unsaturated moieties are transformed to new carbon-carbon bonds, the molecular weight of the radical grows and a new polymer chain is formed, i.e. the polymer is formed from unsaturated monomers and is cross-linked in the same process.

Until recently, polymers designed for use in coatings have relied on photoinitiators with relatively low molecular weight to initiate the cross-linking. In addition, the polymerization reactions for preparing the initial linear polymer often comprise co-reagents and catalysts of the polymerization process which also have relatively low molecular weight. Low molecular weight substances, and their by-products in the polymerization reaction, are generally difficult to remove from the resultant cross-linked polymer, but instead remain within the polymer matrix and diffuse slowly to the surface of the polymer during its lifetime. Over time, low molecular weight substances therefore leach from the polymer into the surrounding environment.

This presents particular problems in the polymers used in the medical field, as patient safety considerations limit the amount and type of substance which can leach from a given polymer. This is especially relevant if the polymer is to be used as a coating or adhesive which is designed to be in contact with the inside or outside of the patient's body. Notably, certain low molecular weight co-reagents and catalysts of polyurethane polymerization are toxic to plants and animals (e.g. dibutyltin dilaurate (DBTDL) or 1,4-diazabicyclo [2.2.2]octane (DABCO)).

Higher molecular weight photoinitiators, in particular polymeric photoinitiators, have comparably higher intrinsic viscosities which most likely result in longer diffusion times through a matrix. Migration of the UV active substances to the surface is therefore diminished when polymeric photoinitiators are used as opposed to lower molecular weight photoinitiators. Scarce literature within the field of polymeric photoinitiators suggests that development of such polymers could lead to novel applications and present solutions for existing needs, such as providing a material with negligent migration of substances to the surface/patient.

The majority of commercial polymeric initiators are based on linear polymer backbone structures where a photoinitiator species is attached by a linking group to one (WO 96/33156) or both (U.S. Pat. No. 4,602,097) ends of a polymeric chain. While this type of structure provides a cost effective route to production of non-migratable photoinitiators, the linear structures tend to give rise to viscous oils and resinous materials. More problematic, the active photoinitiator weight fraction of the molecule is significantly reduced compared to the parent monomer and therefore a reduction in photoactivity by 50% or more is typically observed.

Polymeric photoinitiators based on a polyurethane main chain have been reported by Wei et al. (Macromolecules 2009, 42, 5486-5491). However, all materials prepared are linear polymeric structures with initiator species within the chain itself. While synthetically available, the present inventors find that 'in-chain' polymeric photoinitiators tend to suffer from intrinsically lower photoactivity compared to the photoinitiator monomers. Moreover, linear polymers with in-chain aromatic moieties are prone to give materials with higher degree of crystallinity and much lower solubility compared to other polymer architectures.

Accordingly, it is an object of the present invention to provide polymeric photoinitiators having better photoactivity, in order to efficiently substitute low weight photoinitiators, where migration from the final products is critical. Additionally, it is desirable that such polymeric photoinitiators have good processing properties in the linear polymer state, for use in e.g. coating processes.

Additionally, it is an object of the present invention to further minimize or completely eliminate migration of low molecular weight catalysts, byproducts or co-reagents from final polymeric products, allowing for safer use.

The present invention provides polymer photoinitiators in which the photoinitiator moiety itself becomes an integral part of the polymer, and remains so, during and after the polymerization process. Leaching of photoinitiator and photoinitiator by-products is therefore reduced or even eliminated.

At the same time, the particular design of the photoinitiator monomers allows a reduction in the amount of or even the elimination of co-reagents and catalysts in the polymerization process. In that such substances are minimised or eliminated, their concentrations in the resulting polymers are also reduced, so that leaching of such substances is correspondingly reduced or eliminated. Polymers likely to improve medical safety are thereby obtained.

SUMMARY OF THE INVENTION

In a first aspect, the present invention provides polymeric photoinitiators, being co-polymers of at least one monomer (A) with at least one monomer (B), wherein:

monomer (A) is a photoinitiator monomer (A) of the formula (I):

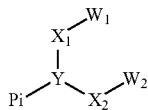

(I)

wherein:
Pi is a photoinitiator moiety;
Y is:

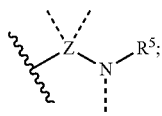

(II)

Z is a linker moiety selected from optionally substituted —O—($C_1$-$C_{12}$ alkylene)-, optionally substituted —S—($C_1$-$C_{12}$ alkylene)-, and optionally substituted —$NR^2$—($C_1$-$C_{12}$ alkylene)-;
—$X_1$—$W_1$ and —$X_2$—$W_2$ are each independently attached to Y at the Z-linker;
—$X_1$—$W_1$ and —$X_2$—$W_2$ may be attached to the Z-linker wherever it is chemically feasible, corresponding to formula (IIa):

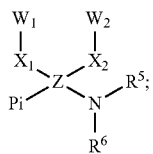

(IIa)

$R^2$ is optionally substituted $C_1$-$C_{12}$ alkyl;
$X_1$ and $X_2$ are each independently selected from a single bond, optionally substituted $C_1$-$C_{12}$ alkylene, optionally substituted $C_2$-$C_{12}$ alkenylene, —O—, —S—, —$NR^4$—, —C(=O)—, —C(=$NR^3$)—, —Si($R^3$)$_2$—O—, optionally substituted $C_3$-$C_8$ cycloalkyl, optionally substituted heterocyclyl, optionally substituted aryl, and combinations thereof;
Z si selected such that N is a tertiary amine;
$R^3$ is H or optionally substituted $C_1$-$C_{12}$ alkyl;
$R^4$ is optionally substituted $C_1$-$C_{12}$ alkyl;
$R^5$ and $R^6$ are each independently selected from optionally substituted $C_1$-$C_6$ alkyl, wherein the carbon atom adjacent to the N-atom is in a —$CH_2$— moiety;

$W_1$ and $W_2$ are each independently selected from —OH, —$CH_2OH$, —$NH_2$, —$NHR^8$, —SH, —NCO, —NCS, and —COOH;
$R^8$ is $C_1$-$C_6$ alkyl; and
any optional substituents are selected from —F, —Cl, —Br, —I, —CN, —$NO_2$, —$C_1$-$C_6$ alkyl, aryl, —O—($C_1$-$C_6$ alkyl), —C(O)—O—($C_1$-$C_6$ alkyl), —S—($C_1$-$C_6$ alkyl), —S(O)—($C_1$-$C_6$ alkyl), —$SO_2$—($C_1$-$C_6$ alkyl), —NH—C(O)—($C_1$-$C_6$ alkyl), —C(O)—NH—($C_1$-$C_6$ alkyl), and —C(O)—$NH_2$;
monomer (B) comprises at least two functional groups $W_3$ and $W_4$, said $W_3$ and $W_4$ being independently selected from —OH, —$CH_2OH$, —$NH_2$, —$NHR^{11}$, —SH, —Si(O$R^{11}$)$_2$—H, —C(=O)—OSi($R^{11}$)$_3$, —NCO, —NCS, —COOH, —COO$R^{11}$, —COO-aryl, —C(=O)—Cl, —O—C(=O)—Cl, —C(O)—$NH_2$, —C(O)—$NHR^{10}$, —NH—C(O)—O$R^{11}$, and —OC(O)—$NHR^{11}$, wherein $R^{10}$ is H or $C_1$-$C_6$ alkyl, and wherein $R^{11}$ is $C_1$-$C_6$ alkyl;
wherein $W_1$, $W_2$, $W_3$ and $W_4$ are selected such that—in the co-polymerization of monomers (A) and (B)—$W_1$ reacts with $W_3$ to form a urethane, thiourethane, urea, thiourea, ester, ether, amide, carbonate, allophanate or biuret moiety, and $W_2$ reacts with $W_4$ to form a urethane, thiourethane, urea, thiourea, ester, ether, amide, carbonate, allophanate or biuret moiety.

Co-polymerization using photoinitiator moieties having the general formula (I) are able to at least partially replace nucleophilic low molecular weight amine catalysts (e.g. DABCO) in polyurethane polymerization processes. The physical and chemical properties of the polymeric photoinitiators of the present invention can be tailored as required, e.g. by varying the relative amounts and the nature of each monomer (A) or (B).

In a second aspect, the present invention provides intermediates to be used in preparation of the polymeric photoinitiators: photoinitiator monomers of the general formula (I):

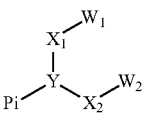

(I)

Wherein formula (I), Pi, Y, $X_1$, $X_2$, $W_1$ and $W_2$ are each as defined herein above for the first aspect of the invention.

With regard to both the first, second and third aspect of the invention it is preferred that Z may be selected from optionally substituted —O—($C_1$-$C_6$ alkylene)-, optionally substituted —S—($C_1$-$C_6$ alkylene)-, and optionally substituted —$NR^2$—($C_1$-$C_6$ alkylene)-. Alternatively that Z may be selected from optionally substituted —O—($C_1$-$C_{12}$ alkylene)-, preferably optionally substituted —O—($C_1$-$C_6$ alkylene)-.

With regard to these aspects it is furthermore preferred that $W_1$ and $W_2$ each independently may be selected from —$CH_2OH$, —OH (i.e. forming a secondary alcohol), —$NH_2$, —$NHR^8$, and —SH. Preferably $W_1$ and $W_2$ may be the same.

Additionally, it is preferred that $X_1$ and $X_2$ independently may be selected from a single bond, optionally substituted $C_1$-$C_{12}$ alkylene, preferably optionally substituted $C_1$-$C_6$ alkylene. Preferably $X_1$ and $X_2$ may be the same. More preferably $X_1$ and $X_2$ may independently be selected from a single bond and optionally substituted $C_1$-$C_{12}$ alkylene, and $W_1$ and $W_2$ may be —$CH_2OH$.

Further details and preferred embodiments for each of the moieties of formula (I) and monomer (B) are described herein in the section "detailed disclosure of the invention" and will be apparent from the claims.

The particular structure of the photoinitiator monomer with two functional groups allows it to be incorporated as a monomer into a linear polymer chain e.g. a polyurethane polymer. Therefore the monomers of formulas (I) are intermediates in the formation of the corresponding polymers. Symmetrical photoinitiator monomers of formula (I) with two functional groups provide good control of the polymerization reaction as each functional group has the same degree of reactivity. In addition, photoinitiators having the general formula (I) are able to at least partially replace nucleophilic low molecular weight amine catalysts (e.g. DABCO) in polyurethane polymerization processes. Furthermore, the use of an alkoxy, amine or alkylsulfanyl link as Z, Za or Zc confers good hydrolytic stability at the same time as providing an improved UV absorption profile due to positive mesomeric effect (M+) of the heteroatoms (N, O or S) in the linker.

In a third aspect, the present invention provides a polyacrylate obtained by radical polymerization of at least one acrylate monomer (Ac) in the presence of a polymeric photoinitiator. The polymeric photoinitiator is a co-polymer of at least one monomer (A) with at least one monomer (B), wherein:

monomer (A) is a photoinitiator monomer (A) of the formula (I):

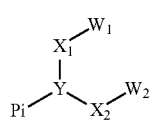

wherein formula (I) is as defined herein for the first and second aspect of the invention;

monomer (B) is as defined herein for the first aspect of the invention; and wherein—in the co-polymerization of monomers (A) and (B) in the polymeric photoinitiator—$W_1$ reacts with $W_3$ to form a urethane, thiourethane, urea, thiourea, ester or amide moiety, and $W_2$ reacts with $W_4$ to form a urethane, thiourethane, urea, thiourea, ester or amide moiety.

Polymerization of acrylate monomers in the presence of the polymeric photoinitiators of the invention is rapid, and—as the polymeric photoinitiator remains bound in the polyacrylate—leaching of photoinitiator is reduced or even completely eliminated.

The invention furthermore provides methods for producing the polymeric photoinitiator; of cross-linking the polymeric photoinitiator by means of UV radiation and/or heat; and for producing a polyacrylate using the polymeric photoinitiator as described.

Additionally, the invention provides the use of the polymeric photoinitiator as a photoinitiator of radical polymerization; the use of a polymeric photoinitiator as a photoinitiator of radical polymerization of acrylate monomers; and the use of a photoinitiator of formula (I) for preparation of a polymeric photoinitiator.

Further details of the above aspects of the invention are presented in the section "detailed disclosure of the invention" and in the dependent claims.

FIGURES

FIG. 1: shows the UV absorption spectra of Speedcure BMS (4-[(4-methylphenyl)sulfanyl]benzophenone; 0.001% w/v in methanol, 1 cm path length; bold black line) and of Speedcure MBP (4-methylbenzophenone; 0.001% w/v in methanol, 1 cm path length; thin dotted line). Illustrating the advantage of having a heteroatom, here —S—, in the para-position adjacent of a photoinitiator moiety.

DETAILED DISCLOSURE OF THE INVENTION

Polymeric photoinitiators being copolymers of monomer (A) of formula (I) provides the means for efficient curing of polymeric materials, such as for example coatings on, or materials in, medical devices, paints, or lacquers. The photoinitiator monomers of the present invention by their two functional groups, allow for incorporation by covalent bonds into polymeric materials, hereby limiting or even preventing the migration of the photoinitiator itself, or its by products, to the surface of the final product encompassing the polymeric material.

As the present photoinitiator monomers or polymeric photoinitiators additionally encompass a tertiary amine, the number of additives used in the polymerization process can further be minimized, which again minimizes the number of chemical used and the therewith associated potential leaching problems. The present photoinitiator monomers and polymeric photoinitiators are hereby specially suited for medical purposes where special considerations in this regard are to be made, both in relation to patient health and regulatory approvals.

It has been found by the present inventors that the inbuild tertiary amine of the photoinitiator monomer may function as a catalyst in the polymerization reaction connecting the photoinitiator monomers of formula (I) as a monomer with one or more further monomers (e.g. monomer (A) and (B) as described herein). Hereby making the addition of such a catalyst unnecessary, and limiting the potential migration of byproducts or co-reagents from a final product.

Additionally, in a UV photocrosslinking of a linear polymer chain, the inbuilt tertiary amine will in a UV photocrosslinking of a linear polymer chain function as an "amine synergist" for the photoinitiator moiety (Pi). When the Pi absorbs UV light and undergoes transition to an excited state, and then forms a radical this may be transferred to a carbon atom adjacent to the inbuilt tertiary amine. The hereby formed radicals will then readily undergo intermolecular recombination to form a covalent crosslink between two proximal polymer chains.

The polymeric photoinitiators have the photoinitiator moieties attached—via a tertiary amine containing linker—as pendant groups on the polymer chain. This polymer design may reduce steric hindrance around the photoactive moiety, hereby increasing photoactivity and may also provide materials with lower viscosity and higher solubility.

The photoinitiator monomers and polymeric photoinitiators of the present invention are useful in connection with a wide variety of polymers, such as for example polyurethanes, polyureas, polythiourethanes, polythioureas, polydithiourethanes, polyesters, polycarbonates, polyphosphonites, polyphosphonates and polyphosphates.

The photoinitiator monomers of the present invention having two functional groups, provide an advantage when used in polymerization into the above polymers, as two or more different types of monomers may be used in forming a linear polymer chain. Hereby allowing for fine tuning and variation of the physical and chemical properties of the obtained polymers. For example more hydrophobic or more hydrophilic polymers may be desired. The latter may be obtained by inserting linkers or varying the polymer chain with monomers, which e.g. enhance and stabilize hydrogenbonding giving better adhesion of the polymer to polar surfaces. This is especially of relevance when a polymeric polyurethane is to be used as a coating on top of another polyurethane material, hereby giving good adhesion and subsequent good cross-linking, binding the two materials together.

As an example of such a polymeric polyurethane photoinitiator can be mentioned a polyurethane having incorporated polyalkylether chain segments. In the definition of the polymeric photoinitiators of the invention such a polymer may correspond to a monomer (A) being of formula (I), a monomer (B) being a diisocyanate and one or more additional monomers (C) being a polyalkylether macromonomer, e.g. a polypropylene glycol or a polyethylene glycol (PEG), such as PEG 400, PEG 2000, PEG 4000 etc. Further details about suitable monomer (C) are described herein elsewhere.

This possibility of variation is in contrast to known copolymerisable unsaturated photoinitiator monomers having e.g. one vinylic functional group. Such variety of properties of polymeric photoinitiators may be difficult to achieve when these are constructed from polymer backbones containing only carbon-carbon bonds (e.g. polyacrylates). Despite the fact that many examples of polymeric photoinitiators based on radical co-polymerisation of acrylic monomers (Macromolecules 2012, 45(12), 5237-5246) have been reported in the literature, such approach suffers from disadvantages. Often, radical co-polymerisation of different monomers mixed in a particular ratio does not provide a polymeric chain in which all the co-monomers are randomly interspersed in the same ratio. This is due to variations in the propagation rate for the different co-monomers. As a result, one of the co-monomers may be left largely unreacted at the end of the polymerisation reaction, or a block co-polymer is obtained, in which the less reactive co-monomer units are concentrated around the polymer end rather than randomly distributed throughout the whole polymer chain.

Polyurethanes

A polyurethane (PU) is a polymer consisting of a chain of organic units joined by urethane (carbamate) links —NH—(C=O)—O—. Polyurethanes are formed by the reaction between one monomer having at least two isocyanate functional groups (—NCO), and another monomer or macromonomer (e.g. a PEG) having at least two alcohol (—OH) groups. In their simplest form, due to the nature of the monomers from which they are prepared, polyurethanes comprise alternating A and B monomers (ABABABABA . . . ). In the second aspect of the present invention, monomer A may contain at least two —OH groups or two —NCO groups and hence participate in the formation of a polyurethane polymer.

A polyurethane according to the present invention may in this manner also be a polymer having such urethane links in the chain in between macromonomer moieties of e.g. polyether, polyester or polycarbonate. This may for example be the case when a polyurethane comprises A and B monomers and a C macromonomer, where A has two alcohol groups, B has two isocyanate groups, and C is a macromonomer having two terminal alcohol functional groups or two terminal isocyanate functional groups (giving e.g. ABCBABCBCBA when C has two alcohol groups). C could here for instance be a polyalkylether (e.g. PEG) or polyester having two terminal alcohol groups. In a preferred embodiment of the second aspect of the invention the polymeric photoinitiator is a polyurethane.

Polyureas

A polyurea is a polymer consisting of a chain of organic units joined by urea (carbamide) moieties —NH—(C=O)—NH—. Polyureas are typically formed by the reaction between one monomer having at least two isocyanate functional groups (—NCO) or macromonomer having two terminal —NCO groups, and another monomer or macromonomer having at least two amine (—NH$_2$) groups. Alternatively, polyureas can be formed by the reaction between one monomer having at least two amine (—NH$_2$) groups, and phosgene (COCl$_2$) or diphosgene (Cl—CO—OCCl$_3$).

A polyurea according to the present invention may in this manner also be a polymer having such urea moieties in the chain in between macromonomer moieties of e.g. polyether, polyester or polycarbonate. This may for example be the case when a polyurea comprises A, B and C monomers, where A has two amine groups, B has two isocyanate groups, and C is a polyamine macromonomer having two free terminal amine groups (giving e.g. ABCBABCBCBA) or C is an polyalkylether macromer having two free functional hydroxyl groups (giving e.g. ABCBCBABCBCBA). The first case providing a polyurea polymer having both urea moieties and amine moieties in the chain, and the later case providing a polymer having both polyurea, polyalkylether and polyurethane moieties in the chain. For example, polyether macromonomer moieties are introduced into the main polymer chain when polyetheramines such as Jeffamine D-400, Jeffamine D-2000 or Jeffamine D-4000 etc. are used as macromonomers with two amine (—NH$_2$) groups. Polyester macromonomer moieties may be introduced into the main polymer chain when amine-terminated polyesters such as those disclosed in U.S. Pat. No. 5,525,683 are used.

Polythiourethanes

A polythiourethane is a generic name for polymers consisting of a chain of organic units joined by —NH—(C=O)—S— or —NH—(C=S)—O— links. The former type of polythiourethanes is formed by the reaction between one monomer having at least two isocyanate functional groups (—NCO), and another monomer having at least two thiol (—SH) groups. The latter type of polythiourethanes is formed by the reaction between one monomer having at least two isothiocyanate functional groups (—NCS), and another monomer having at least two alcohol (—OH) groups.

A polythiourethanes according to the present invention may in this manner also be a polymer having such —NH—(C=O)—S— or —NH—(C=S)—O— links in the chain in between macromonomer moieties of e.g. polyether or polydisulfide. This may for example be the case when a polythiourethane comprises monomers A, B and C, where A has two thiol (—SH) groups, B has two isocyanate groups, and C is a poly(ethylene glycol)dithiol pre-polymer having two free terminal thiol groups (giving e.g. ABCBABCBCBA) or C is an polyalkylether pre-polymer containing disulfide linkages (—S—S—) such as Thiokol® LP-32 or Thiokol® LP-33 two terminal thiol (—SH) functional groups (giving e.g. ABCB-CBABCBCBA). The first case providing a polythiourethane polymer having both polythiourea moieties and polyalkylether moieties in the chain, and the later case providing a polymer having both polythiourea, polyalkylether and disulfide moieties in the chain.

Polythioureas

A polythiourea is a polymer consisting of a chain of organic units joined by thiourea (thiocarbamide) moieties —NH—(C=S)—NH—. Polythioureas are typically formed by the reaction between one monomer having at least two isothiocyanate functional groups (—NCS), and another monomer having at least two amine (—NH$_2$) groups. Alternatively, polythioureas can be formed by the reaction between one monomer having at least two amine (—NH$_2$) groups, and thiophosgene (S=CCl$_2$).

A polythiourea according to the present invention may in this manner also be a polymer having such thiourea moieties in the chain in between macromonomer moieties of e.g. polyether, polyester or polycarbonate. This may for example be the case when a polythiourea comprises A, B and C monomers, where A has two amine groups, B has two isothiocyanate groups, and C is a polyamine macromonomer having two free terminal amine groups (giving e.g. ABCBABCBCBA) or C is a polyalkylether macromer having two free functional hydroxyl groups (giving e.g. ABCBCBABCBCBA). The first case providing a polythiourea polymer having both thiourea moieties and amine moieties in the chain, and the latter case providing a polymer having both polythiourea, polyalkylether and polythiourethane moieties in the chain. For example, polyether macromonomer moieties are introduced into the main polymer chain when polyetheramines such as Jeffamine D-400, Jeffamine D-2000 or Jeffamine D-4000 etc. are used as macromonomers with two amine ($-NH_2$) groups. Polyester macromonomer moieties may be introduced into the main polymer chain when amine-terminated polyesters such as those disclosed in U.S. Pat. No. 5,525,683 are used.

Polydithiourethanes

A polydithiourethane is a polymer consisting of a chain of organic units joined by dithiourethane links —NH—(C=S)—S—. Polydithiourethanes are typically formed by the reaction between one monomer having at least two isothiocyanate functional groups (—NCS), and another monomer having at least two thiol (—SH) groups.

A polydithiourethane according to the present invention may in this manner also be a polymer having such dithiourethane links in the chain in between macromonomer moieties of e.g. polyether or polydisulfide. This may for example be the case when a polydithiourethane comprises monomers A, B and C, where A has two thiol (—SH) groups, B has two isothiocyanate groups, and C is a poly(ethylene glycol)dithiol pre-polymer having two free terminal thiol groups (giving e.g. ABCBABCBCBA) or C is a polyalkylether pre-polymer containing disulfide linkages (—S—S—) such as Thiokol® LP-32 or Thiokol® LP-33 two terminal thiol (—SH) functional groups (giving e.g. ABCBCBABCBCBA). The first example case providing a polydithiourethane polymer having both polydithiourea moieties and polyalkylether moieties in the chain, and the later case providing a polymer having both polydithiourea, polyalkylether and disulfide moieties in the chain.

Polyesters

A polyester is a polymer consisting of a chain of organic units joined by ester moieties —(C=O)—O—. Polyesters are typically formed by the reaction between one monomer having at least two carboxylic acid functional groups (—COOH), two carboxylic ester functional group (—COO-alkyl or —COO-aryl) or two carboxylic acid halide (—COO—X, where X is Cl or Br); and another monomer having at least two alcohol (—OH) groups. The first reaction is an esterification reaction that proceeds in the presence of a Brønsted or Lewis acid catalyst with concomitant removal of water formed during the reaction. The second reaction is a transesterification reaction that proceeds in the presence of a Brønsted or Lewis acid catalyst with concomitant removal a volatile alcohol by-product formed during the reaction. The third reaction proceeds in the presence of a catalytic or stoichiometric quantity of a base such as trialkylamine.

A polyester according to the present invention may in this manner also be a polymer having such ester moieties in the chain in between macromonomer moieties of e.g. a polyether. This may for example be the case when a polyester comprises A, B and C monomers, where A has two alcohol groups, B has two carboxylic acid groups, and C is a polyalkyl ether macromonomer having two terminal hydroxy groups (giving e.g. ABCBABCBCBA). This provides a polyester polymer having both ester moieties and polyether moieties in the chain. For example, polyether macromonomer moieties are introduced into the main polymer chain when polyalkylether, e.g. a polypropylene glycol or a polyethylene glycol (PEG), such as PEG 400, PEG 2000, PEG 4000 etc. are used as monomer C.

Polycarbonate

A polycarbonate is a polymer consisting of a chain of organic units joined by carbonate moieties —O—(C=O)—O—. Polycarbonates are typically formed by the reaction between one monomer having at least two hydroxy functional groups (—OH), and another monomer having at least two chloroformate (—O—(C=O)—Cl) groups. Alternatively, polycarbonates can be formed by the reaction between one monomer having at least two hydroxy functional groups (—OH), and phosgene ($COCl_2$) or diphenyl carbonate (($PhO)_2CO$).

A polycarbonate according to the present invention may in this manner also be a polymer having such carbonate moieties in the chain in between macromonomer moieties of e.g. a polyester or polyamide. This may for example be the case when a polycarbonate comprises monomers A, B and C, where A has two alcohol (—OH) groups, B is ethylenebis(chloroformate), and C is a linear hydroxyl-terminated polyester macromonomer, such as Desmophen 850, (giving e.g. ABCBABCBCBA) or C is a hydroxyl-terminated linear polyamide macromonomer containing amide linkages (—C(O)—NH—) such as those disclosed in patent EP0449419 (giving e.g. ABCBCBABCBCBA). The first case providing a polycarbonate polymer having both carbonate moieties and polyester moieties in the chain, and the later case providing a polymer having both carbonate and amide moieties in the chain.

Polyphosphonites

A polyphosphonite is a polymer consisting of a chain of organic units joined by phosphonite links —O—P(R)—O—, where R is typically methyl or phenyl. Polyphosphonites are typically formed by the reaction between one monomer having at least one dichlorophosphine functional group (—$PCl_2$) or bis(diethylamino)phosphine group (—$P(NEt_2)_2$), and another monomer having at least two alcohol (—OH) groups.

Polyphosphonates

A polyphosphonate is a polymer consisting of a chain of organic units joined by phosphonate links —O—P(=O)(R)—O—, where R is typically methyl or phenyl. Polyphosphonates are typically formed by the reaction between one monomer having at least one phosphonoyl dichloride functional group (—P(=O)$Cl_2$), and another monomer having at least two alcohol (—OH) groups.

Polyphosphates

A polyphosphate is a polymer consisting of a chain of organic units joined by phosphate links —O—P(=O)(OR)—O—, where R is typically methyl or phenyl. Polyphosphates are typically formed by the reaction between one monomer having at least one phosphorodichloridate functional group (—O—P(=O)$Cl_2$), and another monomer having at least two alcohol (—OH) groups.

Curing

When using photoinitiator monomers or polymeric photoinitiators according to the present invention, curing is primarily initiated by exposing the photopolymerizable system containing the polymeric photoinitiators to high energy irradiation, preferably UV light. The photoinitiated process takes place by methods which are known per se, through irradiation with light or UV irradiation in the wavelength range from 100 to 800 nm, and more usually from 280-800 nm. Irradiation sources which may be used are sunlight or artificial lamps, lasers, or vacuum corona processes. Mercury high-pressure, medium pressure or low-pressure lamps and xenon and tungsten lamps, for example, are advantageous. Similarly, excimer, solid-state and diode-based lasers are advantageous. Diode-based light sources in general are advantageous for initiating the chemical reactions.

The ultraviolet spectrum is divided into A, B and C segments where UV A extend from 400 nm down to 315 nm, UV B from 315 to 280 nm, and UV C from 280 to 100 nm. By using a light source that generates light with wavelengths in the visible region (400 to 800 nm) some advantages are obtained with respect to the depth of the curing, provided that the photoinitiator can successfully cure the material at these wavelength. In particular, scattering phenomena are less pronounced at longer wavelength, thus giving a larger penetration depth in the material. Thus, photoinitiator moieties which absorb, and can induce curing, at longer wavelength are of interest. By judiciously choosing substituents on the phenone moieties, the absorption spectrum of the photoinitiator can to some extent be red-shifted, which would then facilitate curing at comparatively greater depths.

Photoinitiator Monomers and Photoinitiator Moieties

The present invention provides photoinitiator monomers of general formula (I) together with polymeric photoinitiators being a co-polymer of at least one monomer (A) with at least one monomer (B). Said monomer (A) is a photoinitiator of general formula (I):

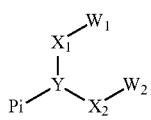

(I)

wherein
Pi is a photoinitiator moiety,
Y is selected from:

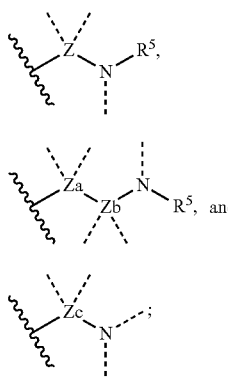

—$X_1$—$W_1$ and —$X_2$—$W_2$ are each independently attached to Y at either the N-atom or the —Z—, -Za-, -Zb-, or -Zc-linker, one or both of the —$X_1$—$W_1$ and —$X_2$—$W_2$ may be attached to the same linker moiety wherever it is chemically feasible (the dotted lines represent a point of attachment on N-atom or linkers, and the wavy line represent the attachment point of Pi); with the proviso that when the linker is either Z or -Za-Zb-, at least one of —$X_1$—$W_1$ and —$X_2$—$W_2$ is attached to an atom other than the N-atom;

when one of —$X_1$—$W_1$ or —$X_2$—$W_2$ is attached to the N-atom, said N-atom is also substituted with $R^5$; when neither of —$X_1$—$W_1$ or —$X_2$—$W_2$ are attached to the N-atom, it is substituted with $R^5$ and $R^6$;

Z is a linker moiety;

Za and Zb together form a linker in which Za is selected from optionally substituted —[O—($C_1$-$C_{12}$ alkylene)]$_n$-, optionally substituted —[$NR^2$—($C_1$-$C_{12}$ alkylene)]$_n$, and optionally substituted —[S—($C_1$-$C_{12}$ alkylene)]$_n$-, wherein Za is joined to Pi via the O, N or S atom in Za, and Zb is a linker moiety;

Zc is a linker moiety selected from —C(O)—($C_1$-$C_{12}$ alkylene)-, —C(O)—$CH_2$—($C_2$-$C_{12}$ alkenylene)-, —C(O)—O—($C_1$-$C_{12}$ alkylene)-, —C(O)—O—($C_2$-$C_{12}$ alkenylene)-, —C(O)—NR—($C_1$-$C_{12}$ alkylene)-, —C(O)—NR—($C_2$-$C_{12}$ alkenylene)-, —($C_1$-$C_{12}$ alkylene)-C(O)—($C_1$-$C_{12}$ alkylene)-, —($C_1$-$C_{12}$ alkylene)-C(O)—O—($C_1$-$C_{12}$ alkylene)-, —($C_1$-$C_{12}$ alkylene)-O—C(O)—($C_1$-$C_{12}$ alkylene)-, —($C_1$-$C_{12}$ alkylene)-C(O)—NR—($C_1$-$C_{12}$ alkylene)-, —($C_1$-$C_{12}$ alkylene)-NR—C(O)—($C_1$-$C_{12}$ alkylene)-, —($C_1$-$C_{12}$ alkylene)-NH—C(O)—NH—($C_1$-$C_{12}$ alkylene)-, —NH—C(O)—NH—($C_1$-$C_{12}$ alkylene)-, and —[$NR^2$—($C_1$-$C_{12}$ alkylene)]$_n$-, wherein any alkylene or alkenylene moiety each independently is optionally substituted with one or more substituents;

$R^1$ is H or optionally substituted $C_1$-$C_{12}$ alkyl;
$R^2$ is optionally substituted $C_1$-$C_{12}$ alkyl;
n is an integer from 1-20;
$X_1$ and $X_2$ are each independently selected from optionally substituted $C_1$-$C_{12}$ alkylene, optionally substituted $C_2$-$C_{12}$ alkenylene, —O—, —S—, —$NR^4$—, —C(=O)—, —C(=$NR^3$)—, —Si($R^3$)$_2$—O—, optionally substituted $C_3$-$C_8$ cycloalkyl, optionally substituted heterocyclyl, optionally substituted aryl, and combinations thereof;

Z, Za, Zb, Zc, $X_1$ and $X_2$ are selected such that N is a tertiary amine;

$X_1$ and $X_2$, or a part thereof, may be linked to one another or to linkers Z, Za, Zb, or Zc to form one or more ring structures;

$R^3$ is H or optionally substituted $C_1$-$C_{12}$ alkyl;
$R^4$ is optionally substituted $C_1$-$C_{12}$ alkyl;
$R^5$ and $R^6$ are each independently selected from optionally substituted $C_1$-$C_6$ alkyl, wherein the carbon atom adjacent to the N-atom is in a —$CH_2$— moiety;

$W_1$ and $W_2$ are each independently selected from —OH, —$CH_2OH$, —$NH_2$, —$NHR^8$, —SH, —Si($OR^8$)$_2$—H, —C(=O)—OSi($R^8$)$_3$, —NCO, —NCS, —COOH, —$COOR^8$, —COO-aryl, —C(=O)—Cl, —O—C(=O)—Cl, —C(O)—$NH_2$, —C(O)—$NHR^7$, —NH—C(O)—$OR^7$, and —OC(O)—$NHR^7$;

$R^7$ is H or $C_1$-$C_6$ alkyl; and
$R^8$ is $C_1$-$C_6$ alkyl;

Pi, $X_1$, $X_2$, $W_1$, $W_2$, Z, Za, Zb, Zc, $R^1$, $R^2$, $R^3$, $R^4$, $R^5$, $R^6$, $R^7$, and $R^8$, will be further described herein below.

A photoinitiator is defined as a substance which, on absorption of light, generates reactive species (ions or radicals) and initiates one or several chemical reactions or transformation. One preferred property of the photoinitiator is good overlap between the emission spectrum of the UV light source and the absorption spectrum of the photoinitiator. Another desired property is a minor or no overlap between the photoinitiator absorption spectrum and the intrinsic combined absorption spectrum of the other components in the polymer matrix. Good compatibility of the photoinitiator with the matrix consisting of material to be cured is also a property of interest.

The photoinitiator monomers with the general formula (I) comprise a photoinitiator moiety, Pi, which provides the required response to UV radiation.

The photoinitiator moieties of the invention are efficient in transforming light from the UV or visible light source to reactive radicals which can abstract hydrogen atoms and other labile atoms from polymers and hence effect polymerization and cross-linking.

Radical photoinitiator moieties can be classified as either cleavable (Norrish type I reaction) or non-cleavable (of which the Norrish type II reaction is a special case, see e.g. A. Gilbert, J. Baggott: "Essentials of Molecular Photochemistry", Blackwell, London, 1991). Upon excitation, cleavable photoinitiator moieties spontaneously break down into two radicals, at least one of which is reactive enough to abstract a hydrogen atom from most substrates. Benzoin ethers (including benzil dialkyl ketals), phenyl hydroxyalkyl ketones and phenyl aminoalkyl ketones are important examples of cleavable photoinitiator moieties. Addition of electron donors is not required but may enhance the overall efficiency of cleavable photoinitiator moieties.

Excited non-cleavable photoinitiators do not break down to radicals but abstract a hydrogen atom from an organic molecule or, more efficiently, abstract an electron from an electron donor (such as an amine or a thiol). The electron transfer produces a radical anion on the photo-initiator and a radical cation on the electron donor. This is followed by proton transfer from the radical cation to the radical anion to produce two uncharged radicals; of these the radical on the electron donor is sufficiently reactive to abstract a hydrogen atom from most substrates. When a non-cleavable photoinitiator moiety is covalently attached as a pendant group via a linker to a polymer chain, there are, in principle, three pathways to form new carbon-carbon bond cross-links as a result of UV irradiation: 1) Coupling of ketyl and aliphatic radicals, 2) dimerisation of ketyl radicals to form a benzopinacol, 3) dimerisation of aliphatic radicals. In cases where the polymeric photoinitiator is a polyurethane with in-chain polyether macromonomer moieties, the hydrogen atom could for instance be abstracted from a —$CH_2$—O— group within the main polymer chain (forming a reactive —CH—O— radical).

Benzophenones and related ketones such as thioxanthones, xanthones, anthraquinones, fluorenones, dibenzosuberones, benzils, and phenyl ketocoumarins are important examples of non-cleavable photoinitiators, and fall within the definition of photoinitiator moieties according to the present invention. Most amines with a C—H bond in α-position to the nitrogen atom and many thiols will work as electron donors. In a preferred embodiment of the invention, Pi of general formula (I) is a non-cleavable photoinitiator, more preferably a Norrish type II photoinitiator. This due to the goal of the present invention to provide photoinitiator monomers of formula (I) where the migration of by-products from the final polymer product is avoided or at least considerably decreased.

Another self-initiating system based on maleimides has also been identified by C. K. Nguyen, W. Kuang, and C. A. Brady from Albemarle Corporation and Brady Associates LLC, both USA (2003): "Maleimide Reactive Oligomers", Proceedings from RadTech Europe 03, Berlin, Germany, Nov. 3-5, 2003, vol. 1, p. 589-94, Vincentz. Maleimides initiate radical polymerization mainly by acting as non-cleavable photo-initiators and at the same time spontaneously polymerize by radical addition across the maleimide double bond. In addition, the strong UV absorption of the maleimide disappears in the polymer, i.e. maleimide is a photobleaching photoinitiator moiety; this could make it possible to cure thick layers. However, as the maleimides in themself are very reactive, undesired side-reactions may occur and therefore in some embodiments of the present invention the Pi of formula (I) does not include maleimides either alone or when mentioned herein in groups of Pi.

A blend of several photoinitiators may exhibit synergistic properties, as is e.g. described by J. P. Fouassier: "Excited-State Reactivity in Radical Polymerization Photo-initiators", Ch. 1, pp. 1-61, in "Radiation curing in Polymer Science and technology", Vol. II ("Photo-initiating Systems"), ed. by J. P. Fouassier and J. F. Rabek, Elsevier, London, 1993. Briefly, efficient energy transfer or electron transfer takes place from one photoinitiator moiety to the other in the pairs [4,4'-bis(dimethylamino)benzophenone+benzophenone], [benzophenone+2,4,6-trimethylbenzophenone], [thioxanthone+methylthiophenyl morpholinoalkyl ketone]. However, many other beneficial combinations may be envisaged. So, in an embodiment of the invention, the photoinitiator moiety Pi includes at least two different types of photoinitiator moieties. In one embodiment of the invention the polymeric photoinitiator comprises at least two different types of photoinitiator moieties, these may be attached to the same or different monomers (A), preferably these may be attached to two different monomer (A) molecules. Preferably, the absorbance peaks of the different photoinitiator moieties are at different wavelengths, so the total amount of light absorbed by the system increases. The different photoinitiator moieties may be all cleavable, all non-cleavable, or a mixture of cleavable and non-cleavable. Preferably, however, the photoinitiator Pi comprises only one photoinitiator moiety.

UV self-crosslinkable terpolymers based on acrylonitrile, methyl acrylate and a UV sensitive comonomer, acryloyl benzophenone (ABP), have also been reported (A. K. Naskar et al. Carbon 43 (2005) 1065-1072; T. Mukundan et al. Polymer 47 (2006) 4163-4171). The free radicals generated during UV irradiation of the terpolymer have been shown to enhance crosslinking and cyclization of nitrile units within the polymer.

Furthermore, it has recently been found that covalently linked 2-hydroxy-1-(4-(2-hydroxyethoxyl)phenyl)-2-methylpropan-1-one, which is commercially available with the trade name Irgacure 2959, and benzophenone in the molecule 4-(4-benzoylphenoxy ethoxy)phenyl 2-hydroxy-2-propyl ketone gives considerably higher initiation efficiency of radical polymerization than a simple mixture of the two separate compounds, see S. Kopeinig and R. Liska from Vienna University of Technology, Austria (2005): "Further Covalently Bonded Photoinitiators", Proceedings from RadTech Europe 05, Barcelona, Spain, Oct. 18-20 2005, vol. 2, p. 375-81, Vincentz. This shows that different photoinitiator moieties may show significant synergistic effects when they are present in the same oligomer or polymer. Such covalently linked photoinitiator moieties are also within the scope of the present invention.

Photoinitiator moieties (Pi) in Formula (I) may be selected from, but not exclusively restricted to, the group consisting of benzoin ethers, phenyl hydroxyalkyl ketones, phenyl aminoalkyl ketones, benzophenones, thioxanthones, xanthones, acridones, anthraquinones, fluorenones, dibenzosuberones, benzils, benzil ketals, α-dialkoxy-acetophenones, α-hydroxy-alkyl-phenones, α-amino-alkyl-phenones, acyl-phosphine oxides, phenyl ketocoumarins, camphorquinones, silane and derivatives thereof, and maleimides. Of these, preferred photoinitiator moieties may be selected from benzophenones, thioxanthones, benzilketals and phenyl hydroxyalkyl ketones, such as 2-hydroxy-2-methyl-1-phenylpropan-1-ones. More preferred photoinitiator moieties may be selected from benzophenones and thioxanthones.

In particular, Pi may be a benzophenone having the general formula (V):

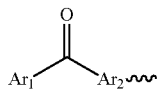
(V)

wherein $Ar_1$ and $Ar_2$ each independently are selected from the same or different aryl, where Y of general formula (I) may be attached at any position on $Ar_2$, i.e. ortho-, meta- or para-position (the attachment point is indicated in formula (V) by the wavy line), and where each aryl independently may be optionally substituted with one or more substituents selected from the group consisting of —F, —Cl, —Br, —I, —CN, —$NO_2$, —$C_1$-$C_6$ alkyl, —$C_2$-$C_6$ alkenyl, —$C_3$-$C_6$ cycloalkyl, aryl, heterocyclyl, —O—($C_1$-$C_6$ alkyl), —O—$C_3$-$C_8$ cycloalkyl, —O-aryl, —C(O)—($R^9$), —C(O)-aryl, —C(O)O—($C_1$-$C_6$ alkyl), —C(O)O-aryl, —O—C(O)-aryl, —O—C(O)—O—($C_1$-$C_6$ alkyl), —O—C(O)—O-aryl, —N($C_1$-$C_6$alkyl)$_2$, —N($C_1$-$C_6$alkyl)($C_3$-$C_6$ cycloalkyl), —N($C_1$-$C_6$alkyl)(aryl), —N(aryl)$_2$, —N($R^9$)—C(O)—($C_1$-$C_6$ alkyl), —N($R^9$)—C(O)-aryl, —C(O)—N($R^9$)$_2$, —C(O)—N($R^9$)-aryl, —C(O)—N(aryl)$_2$, —O—C(O)—N($R^9$)$_2$, —O—C(O)—NH—($C_1$-$C_6$aryl), —N($R^9$)—C(O)—O—($C_1$-$C_6$alkyl), —NH—C(O)—O—($C_1$-$C_6$aryl), —S(O)—($C_1$-$C_6$ alkyl), —S(O)-aryl, —$SO_2$—($C_1$-$C_6$ alkyl), —$SO_2$-aryl, —S—($C_1$-$C_6$ alkyl) and —S-aryl; wherein $R^9$ is H or $C_1$-$C_6$ alkyl.

In a preferred embodiment of the invention the one or more optional substituents are selected from the group consisting of —F, —Cl, —Br, —I, —CN, —$NO_2$, —$C_1$-$C_6$ alkyl, aryl, —O—($C_1$-$C_6$ alkyl), —C(O)—O—($C_1$-$C_6$alkyl), —S—($C_1$-$C_6$ alkyl), —S(O)—($C_1$-$C_6$ alkyl), —$SO_2$—($C_1$-$C_6$ alkyl), —NH—C(O)—($C_1$-$C_6$ alkyl), —C(O)—NH—($C_1$-$C_6$ alkyl), and —C(O)—$NH_2$.

Structures of the formula (V) wherein either or both of $Ar_1$ and $Ar_2$ are substituted in the ortho- or para-position with —OH or —$NH_2$ are known as UV absorbers, giving too low triplet quantum yields (Dr), for use as photoinitiators for practical purposes. Additionally, secondary amines (—NH—R) in the ortho- or para-position gives low triplet quantum yields in polar solvents, being less efficient photoinitiators (see Singh et al. J. Phys. Chem. A 104, 2000, 7002; Suppan et al. J. Photochem. Photobiol. A 94, 1996, 145.). Accordingly, Pi in general formula (I) herein does not include compounds of formula (V) having one or more —OH or —$NH_2$ groups in the ortho- or para-position of the aryl rings. Additionally, in one embodiment of the invention photoinitiators of formula (V) does not have a secondary amine (—NHR, where R e.g. is an alkyl group) in the ortho- or para-position of the aryl rings.

Suitably, $Ar_1$ and $Ar_2$ are the same. Preferably $Ar_1$ and $Ar_2$ each independently may be optionally substituted phenyl, where the phenyl each independently may be optionally substituted with one or more substituents selected from the herein immediately above specified group of substituents; and even more preferably both phenyl (i.e. unsubstituted). In one preferred embodiment of the invention Y (i.e. Z, Za or Zc as appropriate) is attached at the para-position on $Ar_2$, as this provides the maximum opportunity for electron interaction with the carbonyl group, and hence maximum stabilisation of the radical formed. In another preferred embodiment of the invention Y is attached at the ortho-position on $Ar_2$.

Benzophenones are well-studied, commercially-available photoinitiator moieties, and their UV absorption can be tailored according to the substitution pattern of the aryl groups. Preferred substituents on $Ar_1$ and $Ar_2$ are electron-donating groups or atoms such as N, O and S. Such substituents provide UV absorption at a longer wavelength, meaning that LED lamps can be used as a UV source. LED lamps provide advantages such as low energy consumption and generate less heat; thus the substrate temperature can be controlled more accurately.

Accordingly, in a preferred embodiment of the invention $Ar_1$ and $Ar_2$ may each independently optionally be substituted with one or more electron-donating groups or atoms; more preferably such one or more substituents, e.g. one, two, three or four substituents, may be selected from the group consisting of —$CH_3$, —$CH_2CH_3$, —$CH_2CH_2CH_3$, —$CH(CH_3)_2$, —$C_6H_5$, —$OCH_3$, —$OCH_2CH_3$, —$OCH_2CH_2CH_3$, —$OCH(CH_3)_2$, —$OC_6H_5$, —$SCH_3$, —$SCH_2CH_3$, —$SCH_2CH_2CH_3$, —$SCH(CH_3)_2$, —$SC_6H_5$, —$N(CH_3)_2$, —$N(CH_2CH_3)_2$, and —$N(CH_2CH_2OCH_2CH_2)_2$.

A sub-structure which describes photoinitiator monomers of Formula I has the general formula (Va)

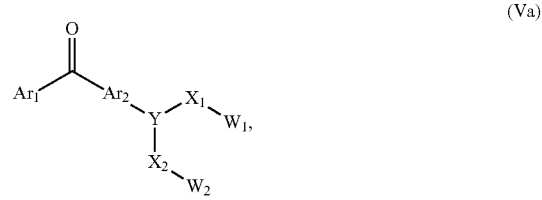
(Va)

wherein $Ar_1$, $Ar_2$, Y, $X_1$, $X_2$, $W_1$ and $W_2$, and preferred options for these groups, are as defined herein and where Y may be present at any position on $Ar_2$. Preferably Y may be present at the para-position on $Ar_2$.

Another sub-structure which describes photoinitiator monomers of general Formula (I), has the general formula (Vb):

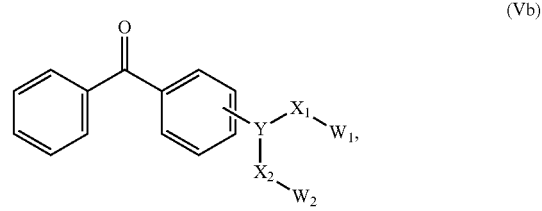
(Vb)

wherein Y, $X_1$, $X_2$, $W_1$ and $W_2$, and preferred options for these groups, are as defined herein. The two aryl rings of formula (Vb) are optionally substituted.

Another sub-structure which describes photoinitiator monomers of Formula (I) has the general formula (Vc):

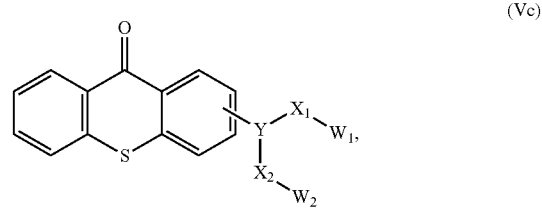
(Vc)

wherein Y, $X_1$, $X_2$, $W_1$ and $W_2$, and preferred options for these groups, are as defined herein. The two aryl rings of formula (Vc) are optionally substituted.

In formulas (Vb) and (Vc) Y may be attached at any position, i.e. ortho-, meta- or para-position to the carbonyl group (the attachment point is indicated in formulas (Vb) and (Vc) by the unattached bond of Y), and where each aromatic ring independently may be optionally substituted with one or more substituents selected from the group specified herein above for formula (V). Preferably Y may be present at the para-position to the carbonyl group.

Another sub-structure which describes photoinitiator monomers of Formula (I) has the general formula (Vd):

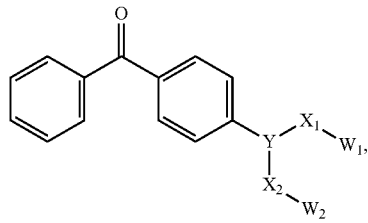

(Vd)

wherein Y, $X_1$, $X_2$, $W_1$ and $W_2$, and preferred options for these groups, are as defined herein. The two aryl rings of formula (Vd) are optionally substituted.

Another sub-structure which describes photoinitiator monomers of Formula (I) has the general formula (Ve):

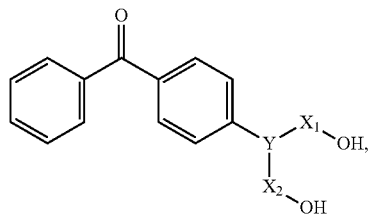

(Ve)

wherein Y, $X_1$, and $X_2$, and preferred options for these groups, are as defined herein. The two aryl rings of formula (Vb) are optionally substituted.

Judicious selection of functional groups can be used to obtain absorption maxima in a desired wavelength region (e.g. impart positive mesomeric effect within the photoinitiator). The ketones described in the present invention are inherent electron accepting groups, so careful selection of electron-donating groups as substituents on aromatic rings within the photoinitiator can lead to absorption profiles matching the light source best suited for the desired curing application. Mechanistically, the efficiency of photoinitiators relies on their ability to intersystem cross from an electronic excited (singlet) state to a triplet state. Some literature has described that such intersystem crossing is less efficient when a higher degree of charge transfer is present within the system. Thus, the absorption profile of a photoinitiator can be controlled to some extent but not without altering the efficiency of radical formation. (see N. J. Turro, *Modern Molecular Photochemistry*, University Science Books: Sausalito, 1991).

In one preferred embodiment of the present invention Y comprises the linker -Za-Zb-, as seen in the partial formula (III) herein above. Specifically Za is designed so that it is attached via a heteroatom, —O—, —$NR^2$—, or —S—, to Pi, i.e. to the $Ar_2$ of formula (V). This particular functionality of Za confers greater hydrolytic stability at the same time as increasing the absorption in the 383-387 nm band region. An example of this effect is the comparison of the UV spectrum of chloro-thioxanthone which has an absorption at 385 nm with a $E_1^1$ of 159 whereas its close relative which has a propoxy substituent on the aromatic ring, 1-chloro-4-propoxy thioxanthone has an absorption at 387 nm and an $E_1^1$ of 175. This enhanced extinction coefficient of absorption allows for faster curing. More preferably Za may be attached via a —O— moiety to Pi, hence in this case Za is —[O—($C_1$-$C_{12}$alkylene)]$_n$-, as such an alkoxy substituent confer greater hydrolytic stability as compared to e.g. ester or amide linkage.

A similar effect can be seen in comparing the UV spectra of 4-[(4-methylphenyl)sulfanyl]-benzophenone (Speedcure BMS) with 4-methylbenzophenone (Speedcure MBP). The absorption maximum of Speedcure BMS at 316 nm is extremely important in increasing the speed of cure of Speedcure BMS over Speedcure MBP. This band is non-existent in Speedcure MBP. FIG. 1 shows the UV spectra of BMS (0.001% w/v in methanol, 1 cm path length; bold black line) and MBP (0.001% w/v in methanol, 1 cm path length, thin dotted line).

The herein above described sub-formulas of photoinitiator monomers of general formula (I), applies for the polymeric photoinitiators and polyacrylates of the invention, including the first and third aspect of the invention, mutatis mutandis. By way of example, the first aspect of the invention defined by formula (I) may be limited to the photoinitiator monomers defined by any of sub-formulas (Vb-IIa), (Vb-IIb), (Va), (Vb), (Vc), (Vd) or (Ve), where Pi, Y, Z, $X_1$, $X_2$, $W_1$, $W_2$, $R^2$, $R^3$, $R^4$, $R^5$, $R^6$, and $R^8$ are as defined for formula (I) or any further embodiments of these as described herein.

DEFINITIONS

The term "alkyl", as used herein, unless otherwise indicated, includes saturated monovalent hydrocarbon radicals having straight or branched moieties. Examples of alkyl moieties include, but are not limited to, methyl, ethyl, propyl, isopropyl, n-butyl, iso-butyl, sec-butyl, tert-butyl and neopentyl. Alkyl may preferably be $C_1$-$C_6$ alkyl, i.e. groups containing from 1 to 6 carbon atoms, and for some embodiments of the present invention more preferably $C_1$-$C_4$ alkyl. The later is for example the case where crowding around a tertiary amine is to be avoided.

The term "alkylene" as used herein specify moieties derived from alkanes in which two H atoms have been removed to form a diradical species. The simplest alkylene is methylene —$CH_2$—, and other alkylenes include ethylene —$CH_2$—$CH_2$—, propylene —$C_3H_6$— and butylene —$C_4H_8$—. The term "alkylene" includes branched and linear alkylenes, with linear alkylenes being most preferred. An alkylene which is a $C_1$-$C_{12}$ alkylene is one which contains between 1 and 12 carbon atoms. Preferred alkylenes contain between 1 and 6 carbon atoms (i.e. $C_1$-$C_6$ alkylenes).

The term "cycloalkyl" as used herein, unless otherwise indicated, includes non-aromatic saturated cyclic alkylene moieties, where alkylene is as defined above, or cyclic alkyl moieties, where alkyl is as defined above. The first applies where the cycloalkyl is used in a linker moiety being attached at two points to the remaining part of the photoinitiator monomers of formula (I). The skilled person will be able to identify in each case what applies. Examples of cycloalkyl include, but are not limited to, cyclopropyl, cyclobutyl, cyclopentyl, cyclohexyl, cycloheptyl, cyclooctyl. Cycloalkyl is preferably $C_3$-$C_8$ cycloalkyl, i.e. cycloalkyl groups containing from 3 to 8 carbon atoms, and more preferably $C_3$-$C_6$ cycloalkyl.

The term "alkenylene" as used herein specify moieties derived from alkenes in which two H atoms have been removed to form a diradical species. Examples include ethenylene —CH═CH— and propenylene —$C_3H_4$— moieties. The term "alkenylene" includes branched, linear and cyclic alkenylene, with linear alkenylene being most preferred. Preferred alkenylenes contain between 2 and 6 carbon atoms (i.e. $C_2$-$C_6$ alkenylenes).

The term "aryl" as used herein define an unsaturated cyclic system which contains a delocalised π-electron system about the ring. Aryl groups may comprise from 4-12 atoms, suitably from 6-8 atoms, most suitably 6 atoms. "Aryl" may preferably comprise carbocyclic rings, and may preferably be phenyl (—$C_6H_5$).

The term "aryl" is also used to include aromatic heterocycles—rings in which one or more atoms in the ring (e.g. 1-3 atoms) are N, S, P or O. Aromatic heterocycles include pyrrole, furan, thiophene, imidazole, imidazoline, pyrazole, pyrazoline, oxazole, oxazoline, isoxazole, isoxazoline, thiazole, thiazoline, isothiazole, isothiazoline (5-membered rings), pyridine, pyran, thiopyran (6-membered rings). The term "aryl" also includes fused ring systems.

When referring to a linker moiety (e.g. Z, Za, Zb, Zc, $X_1$, $X_2$, Q, T), the term "aryl" is used to define moieties derived from arenes in which two H atoms have been removed to form a diradical species (i.e. arylene). Examples include 1,2-phenylene, 1,3-phenylene and 1,4-phenylene.

The term "heterocyclyl" as used herein means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. Preferred heterocyclyls contain about 5 to about 6 ring atoms. The prefix aza, oxa or thia before the heterocyclyl root name means that at least a nitrogen, oxygen or sulfur atom, respectively, is present as a ring atom. The heterocyclyl can be optionally substituted as described above. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,3-dioxolanyl, 1,4-dioxanyl, tetrahydrofuranyl, tetrahydrothiophenyl, tetrahydrothiopyranyl, and the like.

The term "acrylate monomer" is used to describe substances containing the functional group C═C—C(═O)—O—, which are able to polymerize via the alkene C═C moiety. The carbon atoms of the alkene may be substituted.

The term "leaving group", abbreviated "LG", is used to describe a reactive moiety bound to a carbon atom that can be displaced by another moiety in a substitution reaction thus forming a new carbon-carbon or carbon-heteroatom bond. Typically a leaving group LG is —F, —Cl, —Br, —I, —$OSO_2CH_3$, —$OSO_2$-(p-$C_6H_4$)—$CH_3$, —$OSO_2CF_3$.

The term "macromonomers" as used herein to describe a polymer or oligomer, that has two reactive groups, often at the ends, which enables it to act as a monomer in further polymerisation reactions becoming attached to the main backbone of the final polymer. Macromonomers may also be referred to as "pre-polymers". Non-limiting examples of suitable macromonomers or pre-polymers are polyalkylethers, polyesters, polydisulfides, polyamines, or polycarbonates having two free reactive groups, such as —OH groups, —$NH_2$ groups, —COOH groups, or —SH groups. Suitable macromers or pre-polymers to be used in polymeric photoinitiators of the present invention are described further in relation to monomer C.

When photoinitiator monomers of formula (I), comprise only two end groups $W_1$ and $W_2$ capable of taking part in a particular polymerisation reaction, the monomer of formula (I) will be incorporated in the polymer backbone with the photoinitiator as a pendant group via the linkers Z, ZaZb and Zc, branching of the polymer is additionally avoided. It is therefore to be avoided that other functional groups being capable of participating in the desired polymer reaction are present in the photoinitiator monomers of the present invention. This therefore also applies to any optional substituents being present on photoinitiators of formula (I). Accordingly, in the following, when a part of a molecule, or a moiety, is described as "optionally substituted" or "is optionally substituted with one or more substituents" it refers to the optional possibility that one or more hydrogen atoms of a moiety, such as e.g. alkyl, alkylene, alkenyl, alkenylene, cycloalkyl, aryl, and heterocyclyl moieties (all referring to $C_1$-$C_{12}$ alkyl, $C_1$-$C_6$ alkyl, $C_3$-$C_8$ cycloalkyl etc. as appropriate in the context), may or may not be substituted by one or more substituents. For example 1 to 4 substituents, preferably 1 to 3 substituents, more preferably 1 or 2 substituents. Such one or more optional substituents, unless otherwise specifically stated, may be selected from the group consisting of —F, —Cl, —Br, —I, —CN, —$NO_2$, —$C_1$-$C_6$ alkyl, —$C_2$-$C_6$ alkenyl, —$C_3$-$C_6$ cycloalkyl, aryl, heterocyclyl, —O—($C_1$-$C_6$ alkyl), —O—$C_3$-$C_8$ cycloalkyl, —O-aryl, —C(O)—($R^9$), —C(O)-aryl, —C(O)O—($C_1$-$C_6$ alkyl), —C(O)O-aryl, —O—C(O)-aryl, —O—C(O)—O—($C_1$-$C_6$ alkyl), —O—C(O)—O-aryl, —N($C_1$-$C_6$alkyl)$_2$, —N($C_1$-$C_6$alkyl)($C_3$-$C_6$ cycloalkyl), —N($C_1$-$C_6$alkyl)(aryl), —N(aryl)$_2$, —N($R^9$)—C(O)—($C_1$-$C_6$ alkyl), —N($R^9$)—C(O)-aryl, —C(O)—N($R^9$)$_2$, —C(O)—N($R^9$)-aryl, —C(O)—N(aryl)$_2$, —O—C(O)—N($R^9$)$_2$, —O—C(O)—NH—($C_1$-$C_6$aryl), —N($R^9$)—C(O)—O—($C_1$-$C_6$alkyl), —NH—C(O)—O—($C_1$-$C_6$aryl), —S(O)—($C_1$-$C_6$ alkyl), —S(O)-aryl, —$SO_2$—($C_1$-$C_6$ alkyl), —$SO_2$-aryl, —S—($C_1$-$C_6$ alkyl) and —S-aryl; wherein $R^9$ is H or $C_1$-$C_6$ alkyl.

In a preferred embodiment of the invention, the one or more optional substituents are selected from the group consisting of —F, —Cl, —Br, —I, —CN, —$NO_2$, —$C_1$-$C_6$ alkyl, aryl, —O—($C_1$-$C_6$ alkyl), —C(O)—O—($C_1$-$C_6$ alkyl), —S—($C_1$-$C_6$ alkyl), —S(O)—($C_1$-$C_6$ alkyl), —$SO_2$—($C_1$-$C_6$ alkyl), —NH—C(O)—($C_1$-$C_6$ alkyl), —C(O)—NH—($C_1$-$C_6$ alkyl), and —C(O)—$NH_2$.

Photoinitiator monomers of general formula (I) may contain chiral centers and therefore may exist in different enantiomeric or diasteromeric forms. This invention relates to all optical isomers and all stereoisomers of general formula (I), both as racemic mixtures and as individual enantiomers and diastereomers ((+)- and (−)-optically active forms) of such photoinitiator monomers and mixtures thereof. Individual isomers, if desired, can be obtained by known methods, such as optical resolution, optically selective ractions or chromatographic separation in the preparation steps or for the final products.

It will be apparent to one skilled in the art when a photoinitiator of the invention can exist as a salt or solvate form, especially as an acid addition salt or a base addition salt. When a photoinitiator can exist in a salt or solvate form, including hydrated forms, such forms are included within the scope of the invention. Examples of acid addition salts are fluorides, chlorides, bromides, iodides, sulfates, carbonates, phosphates, tetrafluoroborates, tetraarylborates (e.g. tetraphenylborates), hexafluorophosphates, alkyl carboxylates (e.g. acetates), aryl carboxylates (e.g. benzoates), alkyl sulfonates (e.g. mesylates) and aryl sulfonates (e.g. tosylates). Examples of base addition salts are lithium, sodium, potassium, calcium, ammonium and phosphonium salts.

The photoinitiator monomers of general formula (I) may contain a protecting group. The protective group is a group that protects the functional groups of the photoinitiator monomers prior to use in polymerization reactions, such protecting group may be covalently bound independently to $W_1$ and $W_2$ through a labile bond that can be broken before or during polymerisation. Photoinitiator monomers of formula (I) incorporating such protecting groups, are within the scope of the invention. The term "protecting group" or "protective group" as used herein, refers to e.g. silyl protecting group for —OH, —CH$_2$OH, —NH$_2$ or —NHR$^8$, which is selected from typical —Si(CH$_3$)$_3$, —Si(CH$_2$CH$_3$)$_3$, —Si(CH(CH$_3$)$_2$)$_3$, —Si(C$_6$H$_5$)$_3$ and —Si(CH$_3$)$_2$(C(CH$_3$)$_3$) groups. The term "protecting group" as used herein, also refers to e.g. thermally labile protecting group for —NCO or —NCS of $W_3$ or $W_4$ of monomer (B), which is selected from typical diethyl malonate (—CH(COOCH$_2$CH$_3$)$_2$ or 3,5-dimethylpyrazole (—N(—C(CH$_3$)=CH—C(CH$_3$)=N—)) as described in e.g. Protective Groups in Organic Synthesis edited by T. W. Greene et al. (John Wiley & Sons, 1991).

Linkers, Z, -Za-Zb-, and Zc

The portion of the photoinitiator of general Formula (I) indicated by Y, represent a linker moiety in combination with a tertiary amine. The sub-formulas (II), (III), and (IV) incorporates the linkers Z, -Za-Zb-, or Zc, respectively. The linker acts to both bind the photoinitiator moiety to the polymer backbone, and simultaneously hold the photoinitiator at a certain distance from the backbone. The linkers Z, -Za-Zb-, and Zc therefore have two ends. At one end, the linker is joined to the photoinitiator moiety; at the other end, it is joined to the polyurethane backbone. General Formula (I) and sub-formulas (II), (III), and (IV):

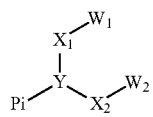
(I)

Y is selected from:

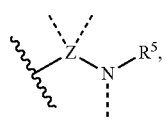
(II)

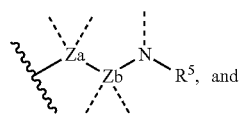
(III)

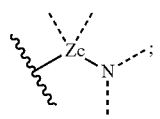
(IV)

—X$_1$—W$_1$ and —X$_2$—W$_2$ are each independently attached to Y at either the N-atom or the —Z—, -Za-, -Zb-, or -Zc- linker, one or both of the —X$_1$—W$_1$ and —X$_2$—W$_2$ may be attached to the same linker moiety wherever it is chemically feasible; with the proviso that when the linker is either Z or -Za-Zb-, at least one of —X$_1$—W$_1$ and —X$_2$—W$_2$ is attached to an atom other than the N-atom;

when neither of —X$_1$—W$_1$ or —X$_2$—W$_2$ are attached to the N-atom, it is substituted with R$^5$ and R$^6$, and when one of —X$_1$—W$_1$ or —X$_2$—W$_2$ is attached to the N-atom, said N-atom is also substituted with R$^5$ (so as the N-atom remain a tertiary amine);

the dotted lines represent a point of attachment on N-atom or linkers, and the wavy line represent the attachment point of Pi;

Pi, X$_1$, X$_2$, W$_1$, W$_2$, Z, Za, Zb, Zc, R$^5$ and R$^6$, will be further described herein below.

The size of the linker is selected according to the desired properties of the photoinitiator. A short linker will provide most opportunity for amine synergist interaction between the amine group N and the photoinitiator moiety. On the other hand, a long linker will provide freer movement of the photoinitiator moiety in the polymerization process, which also provides advantages. A rigid structure may lower the possibility that radicals formed at one site propagate to polymer chains in the vicinity of the photoinitiator, whereas a "loose" structure could facilitate dispersion of radical functionalities over a wider area. Suitably, the linker has a molecular weight of less than 10000 Da, suitably less than 5000 Da, most suitably less than 1000 Da. The linker preferably comprises no more than 50 atoms, preferably no more than 30 atoms.

In addition to the above, photoinitiator monomers and polymeric photoinitiators of the present invention having the —X$_1$—W$_1$ and the —X$_2$—W$_2$ groups removed from the N-atom and attached to the Z, Zc, Za or Zb linker, provide better catalytic properties, as the steric hindrance of the tertiary amine decreases and its availability as a catalyst thereby increases. In addition, when the N-atom has small R$^5$ and R$^6$ groups attached the steric hindrance is decreased further. It is therefore particularly advantageous if R$^5$ and R$^6$ contain a carbon atom adjacent to the N-atom which carry no more than one substituent other than hydrogen.

By excluding secondary amines from the —Z—, -ZaZb-, and -Zc- linkers, the linker will not participate in the polymer reaction, i.e. if such secondary amines where present they could for example form polyurea or allophanate bonds, during a polyurethane polymerisation reaction leading to undesirable cross-linking, when a linear polymer chain is desirable.

In some instances it is desirable to avoid a double bond of an alkenylene group next do the tertiary amine groups. Such moieties are called enamines and, while being good bases, are reactive nucleophiles and might therefore attack —NCO or —NCS moieties of monomer (B, see herein below) and thus interfere with the polymerisation reaction.

Photoinitiator Monomers of Formula (I) Having Formulas (IIa) and (IIb)

The photoinitiator monomers of Formula (I), where Y is sub-formula (II):

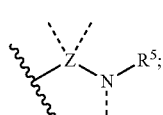
(II)

wherein,

Z is a linker moiety;

—$X_1$—$W_1$ and —$X_2$—$W_2$ are each independently attached to Y at either the N-atom or the Z-linker, one or both of the —$X_1$—$W_1$ and —$X_2$—$W_2$ may be attached to the Z-linker wherever it is chemically feasible (the dotted lines represent points of attachment on N-atom or Z-linker);

with the proviso that at least one of —$X_1$—$W_1$ and —$X_2$—$W_2$ is attached to an atom other than the N-atom;

when one of —$X_1$—$W_1$ or —$X_2$—$W_2$ is attached to the N-atom, said N-atom is also substituted with $R^5$; when neither of —$X_1$—$W_1$ or —$X_2$—$W_2$ are attached to the N-atom, it is substituted with $R^5$ and $R^6$;

$X_1$ and $X_2$ are each independently selected from optionally substituted $C_1$-$C_{12}$ alkylene, optionally substituted $C_2$-$C_{12}$ alkenylene, —O—, —S—, —$NR^4$—, —C(=O)—, —C(=$NR^3$)—, —Si($R^3$)$_2$—O—, optionally substituted $C_3$-$C_8$ cycloalkyl, optionally substituted heterocyclyl, optionally substituted aryl, and combinations thereof;

Z, $X_1$ and $X_2$ are selected such that N is a tertiary amine;

$X_1$ and $X_2$, or a part thereof, may be linked to one another or to linker Z to form one or more ring structures;

$R^3$ is H or optionally substituted $C_1$-$C_{12}$ alkyl;

$R^4$ is optionally substituted $C_1$-$C_{12}$ alkyl;

$R^5$ and $R^6$ are each independently selected from optionally substituted $C_1$-$C_6$ alkyl, wherein the carbon atom adjacent to the N-atom is in a —$CH_2$— moiety;

$W_1$ and $W_2$ are each independently selected from —OH, —$CH_2OH$, —$NH_2$, —$NHR^8$, —SH, —Si(OR$^8$)$_2$—H, —C(=O)—OSi($R^8$)$_3$, —NCO, —NCS, —COOH, —COOR$^8$, —COO-aryl, —C(=O)—Cl, —O—C(=O)—Cl, —C(O)—$NH_2$, —C(O)—$NHR^7$, —NH—C(O)—$OR^7$, and —OC(O)—$NHR^7$;

$R^7$ is H or $C_1$-$C_6$ alkyl; and $R^8$ is $C_1$-$C_6$ alkyl.

Formula (I), wherein Y is formula (II), corresponds to Formulas (IIa) and/or (IIb):

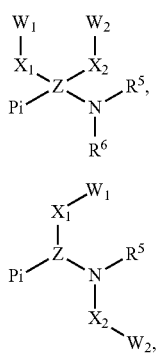

wherein Pi, $X_1$, $X_2$, $W_1$, $W_2$, $R^5$, and $R^6$, are as described herein above and below for general Formula (I).

When Y corresponds to sub-formula (II) comprising linker —Z—, i.e. Formula (IIa) or (IIb), then Z is selected such that N is a tertiary amine, i.e. Z is for example selected such that N in these formulas is not incorporated in an amide moiety.

In one embodiment of the invention, including the first and second aspect, photoinitiator monomers of Formula (IIa) are preferred as the N-atom of Formula (IIa) is less sterically hindered when the —$X_1$—$W_1$ and the —$X_2$—$W_2$ group are attached to the Z-linker. Photoinitiator monomers are hereby provided with increased catalytic properties.

Z may preferably be selected from the group consisting of optionally substituted $C_1$-$C_{12}$ alkylene, optionally substituted $C_2$-$C_{12}$ alkenylene, —O—, —S—, —$NR^2$—, —C(=O)—, —C(=O)—$NR^1$—, —$NR^1$—C(=O)—, —C(=$NR^1$)—, —$SO_2$—, —P(=O)(OR$^1$)—, optionally substituted —$C_3$-$C_8$ cycloalkyl, optionally substituted heterocyclyl, optionally substituted aryl, —[O—($C_1$-$C_{12}$ alkylene)]$_n$-, —[$NR^2$—($C_1$-$C_{12}$ alkylene)]$_n$, —[S—($C_1$-$C_{12}$ alkylene)]$_n$-, and combinations thereof, wherein $R^1$ is H or optionally substituted $C_1$-$C_{12}$ alkyl, $R^2$ is optionally substituted $C_1$-$C_{12}$ alkyl, and n is an integer from 1-20.

Z may be selected from optionally substituted $C_1$-$C_{12}$ alkylene, optionally substituted $C_2$-$C_{12}$ alkenylene, —O—, —S—, —$NR^2$—, —C(=O)—, —C(=O)—$NR^1$—, —$NR^1$—C(=O)—, —C(=$NR^1$)—, optionally substituted —$C_3$-$C_8$ cycloalkyl, optionally substituted heterocyclyl, optionally substituted aryl, —[O—($C_1$-$C_{12}$ alkylene)]$_n$-, —[$NR^2$—($C_1$-$C_{12}$ alkylene)]$_n$, —[S—($C_1$-$C_{12}$ alkylene)]$_n$-, and combinations thereof, wherein $R^1$ is H or optionally substituted $C_1$-$C_{12}$ alkyl, $R^2$ is optionally substituted $C_1$-$C_{12}$ alkyl, and n is an integer from 1-20.

Preferably n may be an integer from 1-10, more preferably from 1-5, such as e.g. 1, 2, 3, 4 or 5, and even more preferably from 1-2.

In that Z may comprise a combination of the above-mentioned groups, the invention encompasses photoinitiator and photoinitiator monomers (A) in which Z is made up of two or more of the above-mentioned groups in series, e.g.

—O—($C_1$-$C_{12}$ alkylene)-

—($C_1$-$C_{12}$ alkylene)-O—($C_1$-$C_{12}$ alkylene)-

—O—($C_1$-$C_{12}$ alkylene)-O—($C_1$-$C_{12}$ alkylene)-

—O—($C_1$-$C_{12}$ alkylene)-O-(aryl)-

—$NR^2$—($C_1$-$C_{12}$ alkylene)-

—($C_1$-$C_{12}$ alkylene)-NR—($C_1$-$C_{12}$ alkylene)-

—$NR^2$—($C_1$-$C_{12}$ alkylene)-NR—($C_1$-$C_{12}$ alkylene)-

—$NR^2$—($C_1$-$C_{12}$ alkylene)-O—($C_1$-$C_{12}$ alkylene)-

—O—($C_1$-$C_{12}$ alkylene)-NR—($C_1$-$C_{12}$ alkylene)-

—C(=O)—O—($C_1$-$C_{12}$ alkylene)-

—C(=O)—NR—($C_1$-$C_{12}$ alkylene)-

—O—C(=O)—($C_1$-$C_{12}$ alkylene)-

—N—C(=O)—($C_1$-$C_{12}$ alkylene)-

—O-aryl-

—($C_1$-$C_{12}$ alkylene)-C(=O)—NR—C(=O)—($C_1$-$C_{12}$ alkylene)-.

In all of the above, the —($C_1$-$C_{12}$ alkylene)-, —($C_2$-$C_{12}$ alkenylene)-, -cycloalkyl, -heterocyclyl-, and -aryl- groups may be substituted or unsubstituted. Other chemically feasible combinations of moieties for Z can be determined by the person skilled in the art. It is particularly advantageous if linker —Z— is attached to the N-atom via a carbon atom which carries no more than one substituent other than hydrogen (—$CH_2$—). This reduces steric hindrance on the N-atom.

$R^1$ may be H. $R^1$ may alternatively be optionally substituted $C_1$-$C_6$ alkyl, such as e.g. methyl, ethyl, propyl, butyl, pentyl or hexyl. In a preferred embodiment of formulas (IIa) or (IIb) $R^1$ is $C_1$-$C_4$ alkyl. $R_2$ may be optionally substituted $C_1$-$C_6$ alkyl, such as e.g. methyl, ethyl, propyl, isopropyl, butyl, isobutyl, pentyl, or isopentyl.

$R^5$ and $R^6$ may each independently be selected from optionally substituted $C_1$-$C_6$ alkyl. In a specific embodiment of the invention $R^5$ and $R^6$ are each independently selected from methyl, ethyl, n-propyl, sec-propyl, n-butyl, sec-butyl, n-pentyl, n-hexyl, sec-pentyl, benzyl, 2-methoxyethyl and 2-ethoxyethyl. More preferably $R^5$ and $R^6$ may each independently be selected from $C_1$-$C_4$ alkyl, such as e.g., methyl, ethyl, n-propyl, sec-propyl, n-butyl, or sec-butyl.

Suitably, Z is selected from optionally substituted $C_1$-$C_{12}$ alkylene, optionally substituted $C_2$-$C_{12}$ alkenylene, —O—, —S—, —$NR^2$—, —[O—($C_1$-$C_{12}$ alkylene)]$_n$-, and combinations thereof, wherein $R^2$ is optionally substituted $C_1$-$C_{12}$ alkyl and n is an integer from 1-20.

Z may specifically be selected from optionally substituted $C_1$-$C_{12}$ alkylene, optionally substituted $C_1$-$C_{12}$ alkenylene, —O—, —S—, —$NR^2$—, and —[O—($C_1$-$C_{12}$ alkylene)]$_n$-, wherein $R^1$ is optionally substituted $C_1$-$C_{12}$ alkyl and n is an integer from 1-20. Z may also be selected from optionally substituted $C_1$-$C_{12}$ alkylene, preferably optionally substituted $C_1$-$C_6$ alkylene.

Alternatively Z may be selected from optionally substituted $C_1$-$C_6$ alkylene, optionally substituted $C_2$-$C_6$ alkenylene, —O—, —S—, —$NR^2$—, —C(=O)—, —C(=O)—$NR^1$—, —$NR^1$—C(=O)—, —C(=$NR^1$)—, optionally substituted —$C_3$-$C_6$ cycloalkyl, optionally substituted heterocyclyl, optionally substituted aryl, —[O—($C_1$-$C_6$ alkylene)]$_n$-, —[$NR^2$—($C_1$-$C_6$ alkylene)]$_n$-, —[S—($C_1$-$C_6$ alkylene)]$_n$-, and combinations thereof; preferably from optionally substituted $C_1$-$C_6$ alkylene, —$NR^2$—, —C(=O)—, —[O—($C_1$-$C_6$ alkylene)]$_n$-, —[$NR^2$—($C_1$-$C_6$ alkylene)]$_n$-; wherein $R^1$ is H or optionally substituted $C_1$-$C_6$ alkyl, $R^2$ is optionally substituted $C_1$-$C_6$ alkyl, and n is an integer from 1-6, preferably 1-2.

Specifically, Z may be selected from $C_1$-$C_6$ alkylene, $C_2$-$C_6$ alkenylene, —$NR^2$—, —C(=O)—($C_1$-$C_6$ alkylene)-, —C(=O)—O—($C_1$-$C_6$ alkylene)-, —C(=O)—NR—($C_1$-$C_6$ alkylene), —$C_3$-$C_6$ cycloalkyl, aryl, heterocyclyl, —[O—($C_1$-$C_6$ alkylene)]$_n$-, —[($C_1$-$C_6$ alkylene)-O—($C_1$-$C_6$ alkylene)]$_n$-, —[$NR^2$—($C_1$-$C_6$ alkylene)]$_n$, and —[S—($C_1$-$C_6$ alkylene)]$_n$-, wherein $R^1$ is H or optionally substituted $C_1$-$C_6$ alkyl, $R^2$ is optionally substituted $C_1$-$C_6$ alkyl, n is an integer from 1-2, and wherein any $C_1$-$C_6$ alkylene, $C_2$-$C_6$ alkenylene, —$C_3$-$C_6$ cycloalkyl, aryl or heterocyclyl moiety each independently is optionally substituted with one or more substituents.

More specifically Z may be selected from $C_1$-$C_6$ alkylene, $C_2$-$C_6$ alkenylene, —$NR^2$—, —C(=O)—($C_1$-$C_6$ alkylene)-, —C(=O)—$NR^1$—, —C(=O)—O—($C_1$-$C_6$ alkylene)-, —C(=O)—NR—($C_1$-$C_6$ alkylene), —[O—($C_1$-$C_6$ alkylene)]$_n$-, —[($C_1$-$C_6$ alkylene)-O—($C_1$-$C_6$ alkylene)]$_n$-, —[$NR^2$—($C_1$-$C_6$ alkylene)]$_n$, and —[S—($C_1$-$C_6$ alkylene)]$_n$-, wherein $R^1$ is H or $C_1$-$C_6$ alkyl, $R^2$ is optionally substituted $C_1$-$C_6$ alkyl, n is an integer from 1-2, and wherein any $C_1$-$C_6$ alkylene, $C_2$-$C_6$ alkenylene, aryl or heterocyclyl moiety each independently is optionally substituted with one or more substituents.

Photoinitiator monomers and photoinitiator monomers (A) of Formula (I) having formulas (IIa) or (IIb) in which Z comprises an electron-donating group adjacent Pi are advantageous, as this provides opportunities to tailor the UV absorption of the photoinitiator moiety. Accordingly, Z may be selected from optionally substituted —O—($C_1$-$C_{12}$ alkylene)-, preferably optionally substituted —O—($C_1$-$C_6$ alkylene)-, optionally substituted —S—($C_1$-$C_{12}$ alkylene)-, preferably optionally substituted —S—($C_1$-$C_6$ alkylene)-, and optionally substituted —$NR^2$—($C_1$-$C_{12}$ alkylene)-, preferably optionally substituted —$NR^2$—($C_1$-$C_6$ alkylene)-; wherein $R^2$ is optionally substituted $C_1$-$C_{12}$ alkyl, preferably $C_1$-$C_6$ alkyl. Z may even be selected from optionally substituted —O—($C_1$-$C_{12}$ alkylene)-, preferably optionally substituted —O—($C_1$-$C_6$ alkylene)-. The above is for instance the case with regard to the first, second and third aspect of the invention.

Alternatively, Z may be selected from optionally substituted $C_1$-$C_6$ alkylene and optionally substituted —O—($C_1$-$C_6$ alkylene)-.

The optional substituents on linker Z is selected from the group specified herein under the definition of "optionally substituted". In a preferred embodiment of the invention, and in the first, second and third aspect, the optional substituents on linker Z is selected from the groups consisting of —F, —Cl, —Br, —I, —CN, —$NO_2$, —$C_1$-$C_6$ alkyl, aryl, —O—($C_1$-$C_6$ alkyl), —C(O)—O—($C_1$-$C_6$ alkyl), —S—($C_1$-$C_6$ alkyl), —S(O)—($C_1$-$C_6$ alkyl), —$SO_2$—($C_1$-$C_6$ alkyl), —NH—C(O)—($C_1$-$C_6$ alkyl), —C(O)—NH—($C_1$-$C_6$ alkyl), and —C(O)—$NH_2$.

Further, sub-structures which describe photoinitiator monomers of General Formula (I), wherein Y comprises the linker Z have the general formulas:

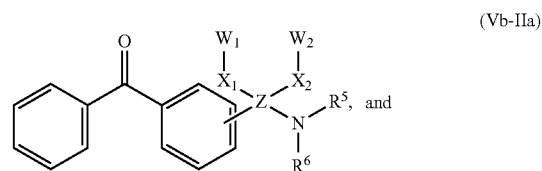
(Vb-IIa)

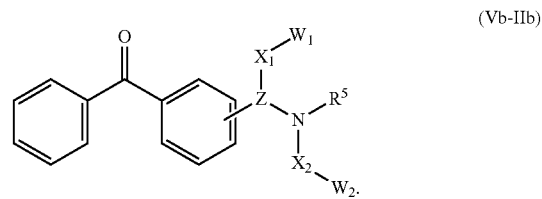
(Vb-IIb)

In a preferred embodiment of the invention the photoinitiator monomers are selected from Formula (IIa) or (Vb-IIa), as the N-atom of these Formulas are less sterically hindered when neither of the —$X_1$—$W_1$ and the —$X_2$—$W_2$ groups are attached to the N-atom. Hereby providing photoinitiator monomers with increased catalytic properties.

Photoinitiator Monomers of Formula (I) Having Formula (IIa), (IIIb), (IIIc), and (IIId)

Further aspects of the invention relates to photoinitiator monomers of Formula (I), where Y is sub-formula (III):

(III)

wherein

Za and Zb together form a linker in which Za is selected from optionally substituted —[O—($C_1$-$C_{12}$ alkylene)]$_n$-, optionally substituted —[$NR^2$—($C_1$-$C_{12}$ alkylene)]$_n$, and optionally substituted —[S—($C_1$-$C_{12}$ alkylene)]$_n$-, wherein Za is joined to Pi via the O, N or S atom in Za, and Zb is a linker moiety; —$X_1$—$W_1$ and —$X_2$—$W_2$ are each independently attached to Y at either the N-atom or the Za-linker or Zb-linker, one or both of the —$X_1$—$W_1$ and —$X_2$—$W_2$ may be attached to the same linker moiety wherever it is chemically feasible;

with the proviso that at least one of —$X_1$—$W_1$ and —$X_2$—$W_2$ is attached to an atom other than the N-atom;

when one of —$X_1$—$W_1$ or —$X_2$—$W_2$ is attached to the N-atom, said N-atom is also substituted with $R^5$; when neither of —$X_1$—$W_1$ or —$X_2$—$W_2$ are attached to the N-atom, it is substituted with $R^5$ and $R^6$;

$R^1$ is H or optionally substituted $C_1$-$C_{12}$ alkyl;
$R^2$ is optionally substituted $C_1$-$C_{12}$ alkyl;
n is an integer from 1-20;

$X_1$ and $X_2$ are each independently selected from optionally substituted $C_1$-$C_{12}$ alkylene, optionally substituted $C_2$-$C_{12}$ alkenylene, —O—, —S—, —NR$^4$—, —C(=O)—, —C(=NR$^3$)—, —Si(R$^3$)$_2$—O—, optionally substituted $C_3$-$C_8$ cycloalkyl, optionally substituted heterocyclyl, optionally substituted aryl, and combinations thereof;

Za, Zb, $X_1$ and $X_2$ are selected such that N is a tertiary amine;

$X_1$ and $X_2$, or a part thereof, may be linked to one another or to linkers Za or Zb, to form one or more ring structures;

$R^3$ is H or optionally substituted $C_1$-$C_{12}$ alkyl;

$R^4$ is optionally substituted $C_1$-$C_{12}$ alkyl;

$R^5$ and $R^6$ are each independently selected from optionally substituted $C_1$-$C_6$ alkyl, wherein the carbon atom adjacent to the N-atom is in a —CH$_2$— moiety;

$W_1$ and $W_2$ are each independently selected from —OH, —CH$_2$OH, —NH$_2$, —NHR$^8$, —SH, —Si(OR$^8$)$_2$—H, —C(=O)—OSi(R$^8$)$_3$, —NCO, —NCS, —COOH, —COOR$^8$, —COO-aryl, —C(=O)—Cl, —O—C(=O)—Cl, —C(O)—NH$_2$, —C(O)—NHR$^7$, —NH—C(O)—OR$^7$, and —OC(O)—NHR$^7$;

$R^7$ is H or $C_1$-$C_6$ alkyl; and $R^8$ is $C_1$-$C_6$ alkyl.

Formula (I), wherein Y is formula (III), corresponds to Formulas (IIIa), (IIIb), (IIIc), and/or (IIId):

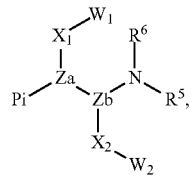

(IIIa)

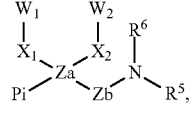

(IIIb)

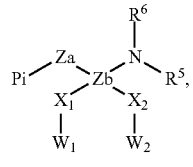

(IIIc)

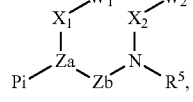

(IIId)

wherein Pi, Za, Zb, $X_1$, $X_2$, $W_1$, $W_2$, $R^5$, and $R^6$, are as described herein above and below for general Formula (I).

When Y corresponds to sub-formula (III) comprising linker -Za-Zb-, i.e. Formula (IIIa), (IIIb), (IIIc), and (IIId), then Zb is selected such that N is a tertiary amine, i.e. Zb is for example selected such that N in these formulas is not incorporated in an amide moiety.

In a preferred embodiment of the invention the photoinitiator monomers are selected from Formula (IIIa), (IIIb) and (IIIc) as the N-atom of these formulas are less sterically hindered when the —$X_1$—$W_1$ and the —$X_2$—$W_2$ group are attached to the linker(s) instead of to the N-atom. Hereby providing photoinitiator monomers with increased catalytic properties. In a more preferred embodiment of the invention the photoinitiator monomers are of Formula (IIIa) or (IIIb), as the N-atom here is even less sterically hindered, having the —$X_1$—$W_1$ and the —$X_2$—$W_2$ groups further from the N-atom.

In one embodiment of the invention Zb is selected from a single bond, optionally substituted $C_1$-$C_{12}$ alkylene, optionally substituted $C_2$-$C_{12}$ alkenylene, —O—, —S—, —NR$^2$—, —C(=O)—, —C(=O)—NR$^1$—, —NR$^1$—C(=O)—, —C(=NR$^1$)—, —SO$_2$—, —P(=O)(OR$^1$)—, optionally substituted $C_3$-$C_8$ cycloalkyl, optionally substituted heterocyclyl, optionally substituted aryl, optionally substituted —[O—($C_1$-$C_{12}$ alkylene)]$_n$-, optionally substituted —[NR$^2$—($C_1$-$C_{12}$ alkylene)]$_n$-, optionally substituted —[S—($C_1$-$C_{12}$ alkylene)]$_n$-, and combinations thereof, wherein $R^1$ is H or optionally substituted $C_1$-$C_{12}$ alkyl, $R^2$ is optionally substituted $C_1$-$C_{12}$ alkyl, and n is an integer from 1-20. More preferably, Zb may be a single bond.

In relation to Za and Zb n may preferably be an integer from 1-10, more preferably from 1-6, such as, e.g., 1, 2, 3, 4, 5 or 6, and even more preferably from 1-2.

$R^1$ may be H. $R^1$ may alternatively be optionally substituted $C_1$-$C_6$ alkyl, such as e.g. methyl, ethyl, propyl, butyl, pentyl or hexyl. $R_2$ may be optionally substituted $C_1$-$C_6$ alkyl, such as e.g. methyl, ethyl, propyl, isopropyl, butyl, isobutyl, pentyl, or isopentyl. In preferred embodiments of formulas (IIIa), (IIIb), (IIIc), or (IIId) $R^1$ or $R^2$ are each independently $C_1$-$C_4$ alkyl.

$R^5$ and $R^6$ may each independently be selected from optionally substituted $C_1$-$C_6$ alkyl. In a specific embodiment of the invention $R^5$ and $R^6$ are each independently selected from methyl, ethyl, n-propyl, sec-propyl, n-butyl, sec-butyl, n-pentyl, n-hexyl, sec-pentyl, benzyl, 2-methoxyethyl and 2-ethoxyethyl. More preferably $R^5$ and $R^6$ may each independently be selected from $C_1$-$C_4$ alkyl, such as e.g., methyl, ethyl, n-propyl, sec-propyl, n-butyl, or sec-butyl. The invention encompasses photoinitiator monomers in which the linker -Za-Zb- is made up of two or more of the above-mentioned groups in series, e.g.

—O—($C_1$-$C_{12}$ alkylene)-

—O—($C_1$-$C_{12}$ alkylene)-O—($C_1$-$C_{12}$ alkylene)-

—O—($C_1$-$C_{12}$ alkylene)-O-(aryl)-

—NR$^1$—($C_1$-$C_{12}$ alkylene)-

—NR$^1$—($C_1$-$C_{12}$ alkylene)-NR—($C_1$-$C_{12}$ alkylene)-

—NR$^1$—($C_1$-$C_{12}$ alkylene)-O—($C_1$-$C_{12}$ alkylene)-

—O—($C_1$-$C_{12}$ alkylene)-NR—($C_1$-$C_{12}$ alkylene)-.

In all of the above, the —($C_1$-$C_{12}$ alkylene)- —($C_2$-$C_{12}$ alkenylene)-, $C_3$-$C_8$ cycloalkyl, -heterocyclyl-, and -aryl- groups may be substituted or unsubstituted. Other chemically feasible combinations of moieties for Z can be determined by the person skilled in the art. It is particularly advantageous if linker -Zb- is attached to the N-atom via a carbon atom which carries no more than one substituent other than hydrogen (—CH$_2$—). This reduces steric hindrance on the N-atom.

In one preferred embodiment of the invention Zb is selected from a single bond, optionally substituted $C_1$-$C_{12}$ alkylene, optionally substituted $C_2$-$C_{12}$ alkenylene, —O—, —S—, —NR$^2$—, —[O—($C_1$-$C_{12}$ alkylene)]$_n$-, and combinations thereof, wherein $R^2$ is optionally substituted $C_1$-$C_{12}$ alkyl and n is an integer from 1-20. Specifically Zb may be selected from a single bond, optionally substituted $C_1$-$C_{12}$ alkylene, optionally substituted $C_2$-$C_{12}$ alkenylene, —O—, —S—, —NR$^2$—, and —[O—($C_1$-$C_{12}$ alkylene)]$_n$-, wherein $R^2$ is optionally substituted $C_1$-$C_{12}$ alkyl, and n is an integer from 1-20. Zb may also be selected from optionally substituted $C_1$-$C_{12}$ alkylene, preferably optionally substituted $C_1$-$C_6$ alkylene. Most preferably, Zb may be selected from a single bond, optionally substituted $C_1$-$C_6$ alkylene and optionally substituted —O—($C_1$-$C_6$ alkylene)-.

Photoinitiator monomers of Formula (I) having formulas (IIIa), (IIIb), (IIIc), or (IIId) in which the linker -Za-Zb- comprises an electron-donating group adjacent Pi are advantageous, as this provides opportunities to tailor the UV absorption of the photoinitiator moiety. Accordingly, in one preferred embodiment of the present invention Za is selected from optionally substituted —[O—($C_1$-$C_{12}$ alkylene)]$_n$-, optionally substituted —[$NR^2$—($C_1$-$C_{12}$ alkylene)]$_n$, and optionally substituted —[S—($C_1$-$C_{12}$ alkylene)]$_n$-; wherein $R^2$ is optionally substituted $C_1$-$C_{12}$ alkyl, and n is an integer from 1-6, preferably 1-2; wherein Za is joined to Pi via the O, N or S atom in Za. In a more preferred embodiment Za is selected from optionally substituted —O—($C_1$-$C_{12}$ alkylene)-, preferably optionally substituted —O—($C_1$-$C_6$ alkylene)-.

In another preferred embodiment Za is selected from optionally substituted —[O—($C_1$-$C_6$ alkylene)]$_n$-, optionally substituted —[$NR^2$—($C_1$-$C_6$ alkylene)]$_n$, and optionally substituted —[S—($C_1$-$C_6$ alkylene)]$_n$-, wherein Za is joined to Pi via the O, N or S atom in Za; and Zb is selected from a linker moiety; preferably Zb is selected from a single bond, optionally substituted $C_1$-$C_6$ alkylene, optionally substituted $C_2$-$C_6$ alkenylene, —O—, —S—, —$NR^2$—, and combinations thereof; more preferably Zb is selected from a single bond, optionally substituted $C_1$-$C_6$ alkylene, optionally substituted $C_2$-$C_6$ alkenylene, —O—, —S—, —$NR^2$—, and —[O—($C_1$-$C_6$ alkylene)]$_n$-; wherein $R^2$ is optionally substituted $C_1$-$C_6$ alkyl, n is an integer from 1-6, preferably 1-2; and Zb is selected so as the N-atom in Formulas (IIIa), (IIIb), (IIIc), and (IIId) is a tertiary amine.

In a specific embodiment of the invention, -Za- is selected from —[O—($C_1$-$C_6$ alkylene)]$_n$-, —[$NR^2$—($C_1$-$C_6$ alkylene)]$_n$, —[S—($C_1$-$C_6$ alkylene)]$_n$-, —O—($C_1$-$C_6$ alkylene)-$NR^2$—($C_1$-$C_6$ alkylene)-, —$NR^2$—($C_1$-$C_6$ alkylene)-O—($C_1$-$C_6$ alkylene)-, —S—($C_1$-$C_6$ alkylene)-O—($C_1$-$C_6$ alkylene)-, —O—($C_1$-$C_6$ alkylene)-S—($C_1$-$C_6$ alkylene)-, —S—($C_1$-$C_6$ alkylene)-NR—($C_1$-$C_6$ alkylene)-, and —$NR^2$—($C_1$-$C_6$ alkylene)-S—($C_1$-$C_6$ alkylene)-, wherein any $C_1$-$C_6$ alkylene moiety optionally is substituted with one or more substituents, wherein $R^2$ is $C_1$-$C_6$ alkyl, and n is an integer from 1-2.

In a specific embodiment of the invention -Zb- is selected from a single bond, —C(═O)—O—$C_1$-$C_6$ alkylene-, —O—C(═O)—$C_1$-$C_6$ alkylene-, —C(═O)—$C_1$-$C_6$ alkylene-, —C(═O)—$NR^1$—$C_1$-$C_6$ alkylene-, —$NR^1$—C(═O)—($C_1$-$C_6$ alkylene)-, —$SO_2$—$C_1$-$C_6$ alkylene-, —P(═O)($OR^1$)—($C_1$-$C_6$ alkylene)-, —C(═O)—O—$C_2$-$C_6$ alkenylene-, —O—C(═O)—$C_2$-$C_6$ alkenylene-, —C(═O)—$C_2$-$C_6$ alkenylene-, —C(═O)—NR—$C_2$-$C_6$ alkenylene-, —$NR^1$—C(═O)—$C_2$-$C_6$ alkenylene-, —C(═O)—NR—$C_2$-$C_6$ alkenylene-, —$SO_2$—$C_2$-$C_6$ alkenylene-, —P(═O)($OR^1$)—$C_2$-$C_6$ alkenylene-, —$C_3$-$C_6$ cycloalkyl, heterocyclyl, aryl, and -aryl-($C_1$-$C_6$ alkyl)-, wherein any $C_1$-$C_6$ alkylene, $C_2$-$C_6$ alkenylene, —$C_3$-$C_6$ cycloalkyl, heterocyclyl or aryl moiety each independently optionally is substituted with one or more substituents, wherein $R^1$ is H or $C_1$-$C_6$ alkyl, and n is an integer from 1-6, preferably 1-2.

In a more specific embodiment of the invention -Zb- is selected from a single bond, —C(═O)—O—$C_1$-$C_6$ alkylene-, —O—C(═O)—$C_1$-$C_6$ alkylene-, —C(═O)—$C_1$-$C_6$ alkylene-, —C(═O)—$NR^1$—$C_1$-$C_6$ alkylene-, —$NR^1$—C(═O)—($C_1$-$C_6$ alkylene)-, —$SO_2$—$C_1$-$C_6$ alkylene-, —P(═O)($OR^1$)—($C_1$-$C_6$ alkylene)-, —$C_3$-$C_6$ cycloalkyl, heterocyclyl, aryl and -aryl-($C_1$-$C_6$ alkyl)-, wherein any $C_1$-$C_6$ alkylene, —$C_3$-$C_6$ cycloalkyl, heterocyclyl or aryl moiety each independently optionally is substituted with one or more substituents, wherein $R^1$ is H or $C_1$-$C_6$ alkyl, and n is an integer from 1-6, preferably 1-2.

Another specific and preferred embodiment of the invention relates to a selected group of Zb linkers being more hydrolytically stable during a polymerisation reaction, this group is selected from a single bond, —C(═O)—$C_1$-$C_6$ alkylene-, —$SO_2$—$C_1$-$C_6$ alkylene-, —P(═O)($OR^1$)—($C_1$-$C_6$ alkylene)-, —$C_3$-$C_6$ cycloalkyl, heterocyclyl, aryl and -aryl-($C_1$-$C_6$ alkyl)-, wherein any $C_1$-$C_6$ alkylene, —$C_3$-$C_6$ cycloalkyl, heterocyclyl or aryl moiety each independently optionally is substituted with one or more substituents, wherein $R^1$ is H or $C_1$-$C_6$ alkyl, and n is an integer from 1-6, preferably 1-2.

The optional substituents on linker -ZaZb- are selected from the group specified herein under the definition of "optionally substituted". In a preferred embodiment of the invention, the optional substituents are selected from the groups consisting of —F, —Cl, —Br, —I, —CN, —$NO_2$, —$C_1$-$C_6$ alkyl, aryl, —O—($C_1$-$C_6$ alkyl), —C(O)—O—($C_1$-$C_6$ alkyl), —S—($C_1$-$C_6$ alkyl), —S(O)—($C_1$-$C_6$ alkyl), —$SO_2$—($C_1$-$C_6$ alkyl), —NH—C(O)—($C_1$-$C_6$ alkyl), —C(O)—NH—($C_1$-$C_6$ alkyl), and —C(O)—$NH_2$.

Further, sub-structures which describe photoinitiator monomers of General Formula (I), wherein Y comprises the linker -Za-Zb- have the general formulas:

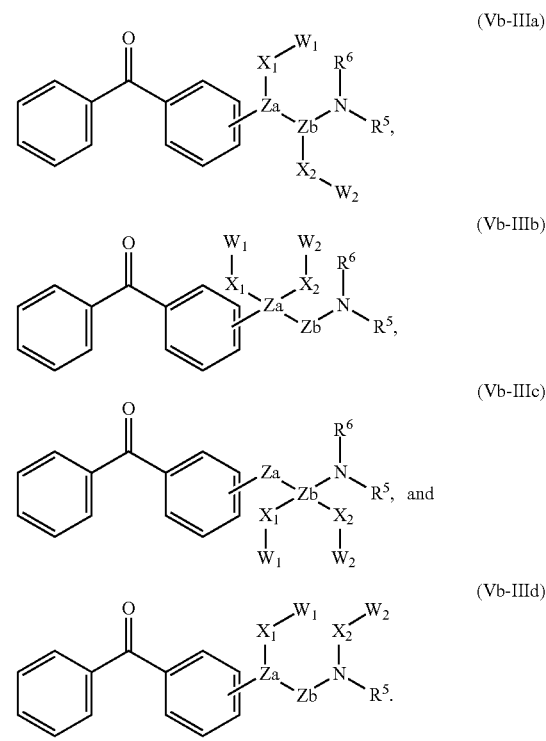

In a preferred embodiment of the invention the photoinitiator monomers are selected from Formula (IIIa), (IIIb), (IIIc), (Vb-IIIa), (Vb-IIIb), or (Vb-IIIc) as the N-atom of these Formulas are less sterically hindered when none of the —$X_1$—$W_1$ and the —$X_2$—$W_2$ groups are attached to the N-atom. Hereby providing photoinitiator monomers with increased catalytic properties.

Photoinitiator Monomers of Formula (I) Having Formula (IVa), (IVb), and (IVc)

Further aspects of the invention relates to photoinitiator monomers of Formula (I), where Y corresponds to sub-formula (IV):

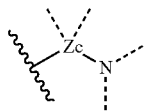
(IV)

Zc is a linker moiety selected from —C(O)—($C_1$-$C_{12}$ alkylene)-, —C(O)—$CH_2$—($C_2$-$C_{12}$ alkenylene)-, —C(O)—O—($C_1$-$C_{12}$ alkylene)-, —C(O)—O—($C_2$-$C_{12}$ alkenylene)-, —C(O)—$NR^1$—($C_1$-$C_{12}$ alkylene)-, —C(O)—$NR^1$—($C_2$-$C_{12}$ alkenylene)-, —($C_1$-$C_{12}$ alkylene)-C(O)—($C_1$-$C_{12}$ alkylene)-, —($C_1$-$C_{12}$ alkylene)-C(O)—O—($C_1$-$C_{12}$ alkylene)-, —($C_1$-$C_{12}$ alkylene)-O—C(O)—($C_1$-$C_{12}$ alkylene)-, —($C_1$-$C_{12}$ alkylene)-C(O)—$NR^1$—($C_1$-$C_{12}$ alkylene)-, —($C_1$-$C_{12}$ alkylene)-$NR^1$—C(O)—($C_1$-$C_{12}$ alkylene)-, —($C_1$-$C_{12}$ alkylene)-NH—C(O)—NH—($C_1$-$C_{12}$ alkylene)-, —NH—C(O)—NH—($C_1$-$C_{12}$ alkylene)-, and —[$NR^2$—($C_1$-$C_{12}$ alkylene)]$_n$-, wherein any alkylene or alkenylene moiety each independently is optionally substituted with one or more substituents;

—$X_1$—$W_1$ and —$X_2$—$W_2$ are each independently attached to Y at either the N-atom or the -Zc- linker, one or both of the —$X_1$—$W_1$ and —$X_2$—$W_2$ may be attached to Zc wherever it is chemically feasible;

when one of —$X_1$—$W_1$ or —$X_2$—$W_2$ is attached to the N-atom, said N-atom is also substituted with $R^5$; when neither of —$X_1$—$W_1$ or —$X_2$—$W_2$ are attached to the N-atom, it is substituted with $R^5$ and $R^6$;

$R^1$ is H or optionally substituted $C_1$-$C_{12}$ alkyl;

$R^2$ is optionally substituted $C_1$-$C_{12}$ alkyl;

$X_1$ and $X_2$ are each independently selected from optionally substituted $C_1$-$C_{12}$ alkylene, optionally substituted $C_2$-$C_{12}$ alkenylene, —O—, —S—, —$NR^4$—, —C(=O)—, —C(=$NR^3$)—, —Si($R^3$)$_2$—O—, optionally substituted $C_3$-$C_8$ cycloalkyl, optionally substituted heterocyclyl, optionally substituted aryl, and combinations thereof;

Zc, $X_1$ and $X_2$ are selected such that N is a tertiary amine;

$X_1$ and $X_2$, or a part thereof, may be linked to one another or to linker Zc to form one or more ring structures;

$R^3$ is H or optionally substituted $C_1$-$C_{12}$ alkyl;

$R^4$ is optionally substituted $C_1$-$C_{12}$ alkyl;

$R^5$ and $R^6$ are each independently selected from optionally substituted $C_1$-$C_6$ alkyl, wherein the carbon atom adjacent to the N-atom is in a —$CH_2$— moiety;

$W_1$ and $W_2$ are each independently selected from —OH, —$CH_2OH$, —$NH_2$, —$NHR^8$, —SH, —Si($OR^8$)$_2$—H, —C(=O)—OSi(R)$_3$, —NCO, —NCS, —COOH, —$COOR^8$, —COO-aryl, —C(=O)—Cl, —O—C(=O)—Cl, —C(O)—$NH_2$, —C(O)—$NHR^7$, —NH—C(O)—$OR^7$, and —OC(O)—$NHR^7$;

$R^7$ is H or $C_1$-$C_6$ alkyl; and $R^8$ is $C_1$-$C_6$ alkyl.

Formula (I), wherein Y is formula (IV), corresponds to Formulas (IVa), (IVb), and/or (IVc):

(IVa)

(IVb)

(IVc)

wherein Pi, Zc, $X_1$, $X_2$, $W_1$ and $W_2$, $R^5$, and $R^6$ are as described herein above and below for general Formula (I).

By having a Zc linker with a relatively high number of heteroatoms present, the solubility of the photoinitiators may be increased, and e.g. the tendency to form hydrogen bonds and the adherence to other polymeric materials, such as hydrophilic polyurethanes, may be increased for polymeric photoinitiator prepared there from.

In order to avoid unnecessary degradation of the Zc linker aryl ester (e.g. Ar—O—C(=O)-alkyl) are to be avoided as these hydrolyse faster and more easily than alkyl esters (e.g. Ar—C(=O)—O-alkyl).

In a preferred embodiment of the invention, Zc is selected from the group consisting of —C(O)—($C_1$-$C_{12}$ alkylene)-, —C(O)—O—($C_1$-$C_{12}$ alkylene)-, —C(O)—O—($C_2$-$C_{12}$ alkenylene)-, —C(O)—NR—($C_1$-$C_{12}$ alkylene)-, —C(O)—NR—($C_2$-$C_{12}$ alkenylene)-, —($C_1$-$C_{12}$ alkylene)-C(O)—($C_1$-$C_{12}$ alkylene)-, —($C_1$-$C_{12}$ alkylene)-C(O)—O—($C_1$-$C_{12}$ alkylene)-, —($C_1$-$C_{12}$ alkylene)-O—C(O)—($C_1$-$C_{12}$ alkylene)-, —($C_1$-$C_{12}$ alkylene)-C(O)—NR—($C_1$-$C_{12}$ alkylene)-, —($C_1$-$C_{12}$ alkylene)-NR—C(O)—($C_1$-$C_{12}$ alkylene)-, and —($C_1$-$C_{12}$ alkylene)-NH—C(O)—NH—($C_1$-$C_{12}$ alkylene)-, wherein alkylene or alkenylene moiety each independently may be optionally substituted with one or more substituents, and $R^1$ is H or optionally substituted $C_1$-$C_{12}$ alkyl.

In another preferred embodiment of the invention, Zc is selected from the group consisting of —C(O)—($C_1$-$C_{12}$ alkylene)-, —C(O)—$CH_2$—($C_2$-$C_{12}$ alkenylene)-, —($C_1$-$C_{12}$ alkylene)-C(O)—($C_1$-$C_{12}$ alkylene)-, wherein alkylene or alkenylene moiety each independently may be optionally substituted with one or more substituents. By having no hydrolytically unstable linkers the photoinitiator monomers may be applied in polymerisation reactions utilising harsher chemical conditions, this is for example desirable in industrial scale preparation where efficiency and costs are of importance.

$R^1$ may be H. $R^1$ may alternatively be optionally substituted $C_1$-$C_6$ alkyl, such as e.g. methyl, ethyl, propyl, butyl, pentyl or hexyl. $R^2$ may be optionally substituted $C_1$-$C_6$ alkyl, such as e.g. methyl, ethyl, propyl, isopropyl, butyl, isobutyl, pentyl, or isopentyl. In preferred embodiments of formulas (IVa), (IVb), or (IVc), $R^1$ or $R^2$ are each independently $C_1$-$C_4$ alkyl.

$R^5$ and $R^6$ may each independently be selected from optionally substituted $C_1$-$C_6$ alkyl. In a specific embodiment of the invention $R^5$ and $R^6$ are each independently selected from methyl, ethyl, n-propyl, sec-propyl, n-butyl, sec-butyl, n-pentyl, n-hexyl, sec-pentyl, benzyl, 2-methoxyethyl and 2-ethoxyethyl. More preferably $R^5$ and $R^6$ may each independently be selected from $C_1$-$C_4$ alkyl, such as e.g., methyl, ethyl, n-propyl, sec-propyl, n-butyl, or sec-butyl.

When Y corresponds to sub-formula (IV) comprising linker -Zc-, i.e. Formula (IVa), (IVb), and (IVc), then Zc is selected such that N is a tertiary amine, i.e Zc is for example selected such that N in these formulas is not incorporated in an amide moiety.

Further, sub-structures which describe photoinitiator monomers of General Formula (I), wherein Y comprises the linker Zc have the general formulas:

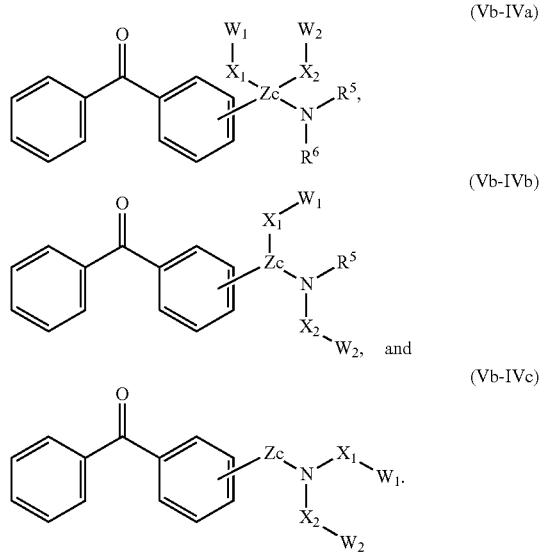

(Vb-IVa)

(Vb-IVb)

(Vb-IVc)

In a preferred embodiment of the invention the photoinitiator monomers are selected from Formula (IVa), (IVb), (Vb-IVa) or (Vb-IVb) as the N-atom of these Formulas are less sterically hindered when one or both of the —$X_1$—$W_1$ and the —$X_2$—$W_1$ groups are attached to the linker instead of to the N-atom. Hereby providing photoinitiator monomers with increased catalytic properties. In a more preferred embodiment of the invention the photoinitiator monomers are of Formula (IVa), as the N-atom here is even less sterically hindered, having the —$X_1$—$W_1$ and the —$X_2$—$W_1$ group fully removed from the N-atom.

$X_1$ and $X_2$

The groups $X_1$ and $X_2$ serve to connect the amine N with the end groups $W_1$ and $W_2$. The size and form of these groups can be varied to adjust the properties of the photoinitiator polymer such as e.g. a polyurethane photoinitiator polymer.

$X_1$ and $X_2$ may be the same or different, and are preferably the same, for ease of chemical synthesis.

In the first, second and third aspect of the invention $X_1$ and $X_2$ are each independently selected from a single bond, optionally substituted $C_1$-$C_{12}$ alkylene, optionally substituted $C_2$-$C_{12}$ alkenylene, —O—, —S—, —$NR^4$—, —C(=O)—, —C(=$NR^3$)—, —Si($R^3$)$_2$—O—, optionally substituted $C_3$-$C_8$ cycloalkyl, optionally substituted heterocyclyl, optionally substituted aryl, and combinations thereof.

Suitably, $X_1$ and $X_2$ may each independently be selected from optionally substituted $C_1$-$C_{12}$ alkylene, optionally substituted $C_2$-$C_{12}$ alkenylene, —O—, —S—, —$NR^4$—, —C(=O)—, —C(=$NR^3$)—, —Si($R^3$)$_2$—O—, optionally substituted $C_3$-$C_8$ cycloalkyl, optionally substituted heterocyclyl, optionally substituted aryl, and combinations thereof, wherein $R^3$ is H or optionally substituted $C_1$-$C_{12}$ alkyl, and $R^4$ is optionally substituted $C_1$-$C_{12}$ alkyl. In that $X_1$ and $X_2$ may comprise combinations of the above-mentioned groups, the invention encompasses photoinitiator monomers in which $X_1$ and $X_2$ are made up of two or more of the above-mentioned groups in series.

Suitably, $X_1$ and $X_2$ are independently selected from optionally substituted $C_1$-$C_{12}$ alkylene, optionally substituted $C_2$-$C_{12}$ alkenylene, —O—, —S—, —$NR^4$—, —C(=O)—, —C(=$NR^3$)—, optionally substituted $C_3$-$C_8$ cycloalkyl, optionally substituted heterocyclyl, optionally substituted aryl, wherein $R^3$ is H or optionally substituted $C_1$-$C_{12}$ alkyl, preferably $C_1$-$C_6$ alkyl, more preferably $C_2$-$C_6$ alkyl, and $R^3$ is optionally substituted $C_1$-$C_{12}$ alkyl, preferably $C_1$-$C_6$ alkyl, more preferably $C_2$-$C_6$ alkyl.

In order to minimize the sterically hindrance at the tertiary amine of formula (I) and subformulas thereof, it is preferred that the carbon atom of $X_1$ and/or $X_2$ adjacent to the tertiary amine atom carry no more than one substituent other than Hydrogen.

$R^3$ may be H. $R^3$ may alternatively be optionally substituted $C_1$-$C_6$ alkyl, such as e.g. methyl, ethyl, propyl, butyl, pentyl or hexyl. $R^4$ may be optionally substituted $C_1$-$C_6$ alkyl, such as e.g. methyl, ethyl, propyl, isopropyl, butyl, isobutyl, pentyl, or isopentyl. In preferred embodiments $R^3$ or $R^4$ are each independently $C_2$-$C_6$ alkyl.

$X_1$ and $X_2$, or parts thereof, may be linked to one another or to linkers Z, Za, Zb, or Zc to form one or more ring structures. $X_1$ and $X_2$ may be linked to one another to form one or more ring structures. In one embodiment of the invention, including the first second and third aspect, $X_1$ and $X_2$ is not linked to one another or to the linkers.

$X_1$ and $X_2$ may independently be selected from optionally substituted $C_1$-$C_{12}$ alkylene, —O—, —S—, —$NR^4$—, wherein $R^4$ is optionally substituted $C_1$-$C_{12}$ alkyl, and combinations thereof. $X_1$ and $X_2$ may be linked to one another to form one or more ring structures. Preferably, $X_1$ and $X_2$ may independently be selected from a single bond, optionally substituted $C_1$-$C_{12}$ alkylene, preferably optionally substituted $C_1$-$C_6$ alkylene. Additionally, $X_1$ and $X_2$ may independently be selected from optionally substituted $C_1$-$C_{12}$ alkylene, preferably optionally substituted $C_2$-$C_6$ alkylene.

Tertiary Amine, N

In the photoinitiator monomers of Formula (I), or the photoinitiator monomer (A) described by Formula (I), N represents a tertiary amine (i.e. a nitrogen atom bound directly to three carbon atoms, in which the carbon atoms are saturated alkyl or aryl carbon atoms).

The N atom in the photoinitiator monomers in Formula (I) has a number of functions. Firstly, and most importantly the N atom in the photoinitiator monomers of Formula (I)—being a tertiary amine—is basic. Suitably, the N atom has a $pK_b$ of less than 13, preferably a $pK_b$ less than 6. The amine N atom is therefore able to partially or completely replace the amine catalysts which are typically used in polyurethane polymerization reactions (e.g. 1,4-diazabicyclo[2.2.2]octane (DABCO), dimethylcyclohexylamine (DMCHA) and dimethylethanolamine (DMEA)). In this way, the use of such low molecular weight tertiary amine catalysts can be reduced or completely avoided. The fewer additives added during polymerization, the fewer compounds or reaction byproducts may migrate from the final polymer.

When the N atom is crowded due to large or bulky $X_1$ and/or $X_2$ groups attached thereto, the effectivity of the N atom as a catalyst decreases. Therefore in one embodiment of Formula (I) $X_1$, $X_2$, $R^5$, and/or $R^6$ each independently are selected to provide photoinitiator monomers with less crowded N atoms, accordingly, $X_1$ and $X_2$ may preferably each independently be selected from groups that are attached to Y via carbon atom which carries no more than one substituent other than hydrogen such as e.g. —$CH_2$— group, and $R^5$ and $R^6$ may preferably each independently be selected from $C_1$-$C_4$ alkyl, such as e.g., methyl, ethyl, n-propyl, sec-propyl, n-butyl, or sec-butyl.

Likewise, one preferred embodiment of the invention relates to photoinitiator monomers of Formula (I), or the photoinitiator monomer (A) described by Formula (I), having formulas (IIa), (IIIa), (IIIb), (IIIc) and (IVa), as these compounds are less crowded, the —$X_1$—$W_1$ and —$X_2$—$W_2$ groups therein are attached on either Z, Za, Zb, or Zc instead on the N atom. Hereby providing a more efficient and structural available catalyst for the polymerisation reaction.

Secondly, the tertiary amine in the structure, when irradiated with UV, can have a proton abstracted by the photoinitiator moiety (either intramolecularly or intermolecularly) from the carbon atoms adjacent to the amino nitrogen. This will give rise to an active radical capable of initiating polymerization or cross-linking.

Thirdly, in some embodiments of the present invention the N atom provides the appropriate branching of the molecule, so that the photoinitiator moieties are pendant from the polyurethane backbone. This is the case for e.g. photoinitiator monomers of Formula (IVc).

The linkers Z, Za, Zb, and Zc, and $X_1$ and $X_2$ are selected such that N is a tertiary amine (i.e. so that the atom adjacent N is a saturated carbon atom, or an aryl carbon atom) so that the basic properties of N are preserved. Preferably, at least two of the groups Z, Za, Zb, Zc, $X_1$ and $X_2$ in the tertiary amine are alkyl.

In formula (I) the N-atom of Y is always to be a tertiary amine. Hence, when there herein is written "when one of —$X_1$—$W_1$ or —$X_2$—$W_2$ is attached to the N-atom, said N-atom is substituted with $R^5$; when neither of —$X_1$—$W_1$ or —$X_2$—$W_2$ are attached to the N-atom, said N-atom is substituted with both $R^5$ and $R^{6'''}$" it is meant to described that the N-atom of the tertiary amine always will be "substituted" with three "moieties", one of which always is a linker (Z, Za, Zb or Zc), the other two being selected from: —$X_1$—$W_1$, —$X_2$—$W_2$, $R^5$ and $R^6$. Accordingly when e.g. Z and —$X_1$—$W_1$ are attached to the N-atom, the third moiety is a $R^5$ moiety. Similar when e.g. Z is attached to the N-atom, and —$X_1$—$W_1$ and —$X_2$—$W_2$ both are attached to Z, the second and the third moiety on the N-atom are $R^5$ and $R^6$. The above with the proviso that when the linker is either Z or -Za-Zb-, at least one of —$X_1$—$W_1$ and —$X_2$—$W_2$ is attached to an atom other than the N-atom.

End Groups, $W_1$, $W_2$

The end groups $W_1$ and $W_2$ in Formula (I) allow the photoinitiator to be incorporated into a growing polymer chain, such as e.g. a polyurethane chain. $W_1$ and $W_2$ are therefore selected from those functional groups which are reactive in polymerization reactions and which then are able to bond to other monomers. When the intended polymer is a polyurethane the monomers may therefore have reactive $W_1$ and $W_2$ groups in the form of —OH or —NCO, as these are able to bond to other polyurethane monomers to thus form polyurethane.

$W_1$ and $W_2$ are each independently selected from —OH (i.e. forming a secondary alcohol), —$CH_2OH$, —$NH_2$, —$NHR^8$, —SH, —$Si(OR^8)_2$—H, —C(=O)—$OSi(R^8)_3$, —NCO, —NCS, —COOH, —$COOR^8$, —COO-aryl, —C(=O)—Cl, —O—C(=O)—Cl,
—C(O)—$NH_2$, —C(O)—$NHR^7$, —NH—C(O)—$OR^7$, and —OC(O)—$NHR^7$, wherein $R^7$ is H or $C_1$-$C_6$ alkyl, and wherein $R^8$ is $C_1$-$C_6$ alkyl.

Preferably, $W_1$ and $W_2$ may independently be selected from the group consisting of —OH (i.e. forming a secondary alcohol), —$CH_2OH$, —$NH_2$, —$NHR^8$, —SH, —NCO, —NCS, and —COOH. This is for instance the case for the first, second and third aspect of the invention. More preferably, selected from the group consisting of —$CH_2OH$, —$NH_2$, —$NHR^8$, and —SH.

Care should be taken when selecting suitable $X_1$ and $X_2$ groups, such that $W_1$ and $W_2$ fulfil these criteria. For example, $X_1$ and $X_2$ may independently be selected from optionally substituted $C_1$-$C_{12}$ alkylene, when $W_1$ and $W_2$ are —OH. In the first, second and third aspect of the invention $X_1$ and $X_2$ may preferably be independently selected from a single bond or optionally substituted $C_1$-$C_{12}$ alkylene, when $W_1$ and $W_2$ are —$CH_2OH$.

In the definitions of $W_1$ and $W_2$, —$CH_2OH$ denotes primary alcohol attached onto $X_1$ or $X_2$. For instance, if $W_1$ is —$CH_2OH$ and $X_1$ is methylene then the moiety —$X_1$—$W_1$ is —$CH_2CH_2OH$; and if $W_1$ is —$CH_2OH$ and $X_1$ is a single bond then the moiety —$X_1$—$W_1$ is —$CH_2OH$. In the same manner in the definitions of $W_1$ and $W_2$, —OH is to be understood as a forming a secondary alcohol with $X_1$ or $X_2$. For instance, if $W_1$ is —OH and $X_1$ is ethane-1,1-diyl then the moiety —$X_1$—$W_1$ may be —CH(OH)$CH_3$; and if $W_1$ is —OH and $X_1$ is a single bond then the moiety —$X_1$—$W_1$ is —OH attached directly to the carbon branching atom. Due to the lower reactivity of tertiary alcohols these are undesirable as $W_1$ and $W_2$ groups.

$R^7$ and $R^8$ may independently be $C_1$-$C_6$ alkyl, such as e.g. methyl, ethyl, propyl, butyl, pentyl or hexyl. $R^7$ may additionally be H.

$W_1$ and $W_2$ are selected according to the design of the polymer. If desired, $W_1$ and $W_2$ may be different end groups. It is preferably for ease of synthesis of the photoinitiator, however, that $W_1$ and $W_2$ are the same.

When $W_1$ and $W_2$ are a two alcohol groups, it is preferred that these are attached at $X_1$ and $X_2$ so as both form a primary alcohol (i.e. —$CH_2OH$), or both form a secondary alcohol (i.e. —OH in the definition of $W_1$ and $W_2$). Hereby allowing for symmetric growth of the polymer chain. In the same manner, it is preferred that when $W_1$ and $W_2$ are two amine groups, i.e. —$NH_2$ or —$NHR^8$, they are either two primary amine groups or two secondary amine groups.

Accordingly, in one embodiment of the present invention $W_1$ and $W_2$ is selected from the group consisting of —OH, —$CH_2OH$, —$NH_2$, —$NHR^8$, —SH, —$Si(OR^8)_2$—H, —C(=O)—$OSi(R^8)_3$], —NCO, —NCS, —COOH, —$COOR^8$, —COO-aryl, —C(=O)—Cl, —O—C(=O)—Cl, —C(O)—$NH_2$, —C(O)—$NHR^7$, —NH—C(O)—$OR^7$, and —OC(O)—$NHR^7$, wherein $R^7$ is H or $C_1$-$C_6$ alkyl, $R^8$ is $C_1$-$C_6$ alkyl, and wherein $W_1$ and $W_2$ are the same.

In a preferred embodiment of the invention $W_1$ and $W_2$ is selected from the group consisting of —OH, —$CH_2OH$, —$NH_2$, —$NHR^8$, —SH, —NCO, —NCS, and —COOH; and more preferably from the group consisting of —OH, —$CH_2OH$, —$NH_2$, —$NHR^8$, and —SH; wherein $W_1$ and $W_2$ are the same.

A preferred embodiment of the invention relates to photoinitiator monomers of general formula (I), or subformulas thereof, where $W_1$ and $W_2$ are the same and are either —OH (i.e. forming a secondary alcohol) or —CH$_2$OH. Likewise, a preferred embodiment of the second aspect of the invention relates to a polymeric photoinitiator which is a co-polymer of at least one monomer (A) with at least one monomer (B), where the polymer is a polyurethane and photoinitioator monomer (A) is of general formula (I), or subformulas thereof, where $W_1$ and $W_2$ are the same and either —OH or —CH$_2$OH.

In that only two end groups $W_1$ and $W_2$ are present, the photoinitiator does not promote branching of the polyurethane. Instead, the photoinitiator monomers of Formula (I) are incorporated partly into the polymer chain, while the photoinitiator moieties are pendant from the chain via the linkers Z, -Za-Zb-, or Zc.

Specific Photoinitiator Monomers

Suitable photoinitiator monomers according to the invention include:

2-(4-benzoylphenoxymethyl)-2-[(dimethylamino)methyl] propane-1,3-diol;
2-(4-benzoylphenoxymethyl)-2-(piperidin-1-ylmethyl)propane-1,3-diol;
1-chloro-4-{2-[(dimethylamino)methyl]-3-hydroxy-2-(hydroxymethyl)propoxy}-9H-thioxanthen-9-one;
2-[(4-benzoylphenyl)methyl]-2-[(dimethylamino)methyl] propane-1,3-diol;
2-[3-(4-benzoylphenoxyl)propyl]-2-[(dimethylamino)methyl]propane-1,3-diol;
2-{[5-hydroxy-4-(hydroxymethyl)-4-(piperidin-1-ylmethyl)pentyl]oxy}-9H-thioxanthen-9-one;
3-(4-benzoylphenoxy)-2-{[(2-hydroxyethyl)(methyl)amino] methyl}propan-1-ol;
{4-[2-(dimethylamino)-3-hydroxy-2-(hydroxymethyl)propyl]phenyl}(phenyl)methanone;
2-[3-(4-benzoylphenoxyl)propyl]-2-(dimethylamino)propane-1,3-diol;
2-[(dimethylamino)methyl]-3-hydroxy-2-(hydroxymethyl) propyl 4-benzoylbenzoate;
2-[(dimethylamino)methyl]-3-hydroxy-2-(hydroxymethyl) propyl 2-benzoylbenzoate;
3-hydroxy-2-(hydroxymethyl)-2-(morpholin-4-ylmethyl) propyl 4-benzoylbenzoate;
3-hydroxy-2-(hydroxymethyl)-2-(morpholin-4-ylmethyl) propyl 2-benzoylbenzoate;
2-[(dimethylamino)methyl]-3-hydroxy-2-(hydroxymethyl) propyl 2-[(1-chloro-9-oxo-9H-thioxanthen-4-yl)oxy]acetate;
3-hydroxy-2-(hydroxymethyl)-2-(morpholin-4-ylmethyl) propyl 2-[(1-chloro-9-oxo-9H-thioxanthen-4-yl)oxy]acetate;
(4-{[3-(dimethylamino)-1,4-dihydroxybutan-2-yl] oxy}phenyl)(phenyl)methanone;
1-(4-benzoylphenyl)-2-[bis(2-hydroxyethyl)amino]ethanone; or
1-(4-benzoylphenyl)-3-[bis(2-hydroxyethyl)amino]propan-1-one.

Preferred photoinitiator monomers according to the invention include:

2-(4-benzoylphenoxymethyl)-2-[(dimethylamino)methyl] propane-1,3-diol;
2-(4-benzoylphenoxymethyl)-2-(piperidin-1-ylmethyl)propane-1,3-diol;
1-chloro-4-{2-[(dimethylamino)methyl]-3-hydroxy-2-(hydroxymethyl)propoxy}-9H-thioxanthen-9-one;
2-[3-(4-benzoylphenoxyl)propyl]-2-[(dimethylamino)methyl]propane-1,3-diol;
2-{[5-hydroxy-4-(hydroxymethyl)-4-(piperidin-1-ylmethyl)pentyl]oxy}-9H-thioxanthen-9-one;
2-[3-(4-benzoylphenoxyl)propyl]-2-(dimethylamino)propane-1,3-diol;
2-[(dimethylamino)methyl]-3-hydroxy-2-(hydroxymethyl) propyl 2-benzoylbenzoate;
2-[(dimethylamino)methyl]-3-hydroxy-2-(hydroxymethyl) propyl 2-[(1-chloro-9-oxo-9H-thioxanthen-4-yl)oxy]acetate; or
1-(4-benzoylphenyl)-2-[bis(2-hydroxyethyl)amino]ethanone.

Suitable photoinitiator monomers according to the first, second and third aspect of the invention include:

2-(4-benzoylphenoxymethyl)-2-[(dimethylamino)methyl] propane-1,3-diol;
1-chloro-4-{2-[(dimethylamino)methyl]-3-hydroxy-2-(hydroxymethyl)propoxy}-9H-thioxanthen-9-one;
2-[3-(4-benzoylphenoxyl)propyl]-2-[(dimethylamino)methyl]propane-1,3-diol;
2-[3-(4-benzoylphenoxyl)propyl]-2-(dimethylamino)propane-1,3-diol; or
(4-{[3-(dimethylamino)-1,4-dihydroxybutan-2-yl] oxy}phenyl)(phenyl)methanone.

Preferred photoinitiator monomers according to the first, second and third aspect of the invention include:

2-(4-benzoylphenoxymethyl)-2-[(dimethylamino)methyl] propane-1,3-diol;
1-chloro-4-{2-[(dimethylamino)methyl]-3-hydroxy-2-(hydroxylmethyl)propoxy}-9H-thioxanthen-9-one;
2-[3-(4-benzoylphenoxyl)propyl]-2-[(dimethylamino)methyl]propane-1,3-diol; or
2-[3-(4-benzoylphenoxyl)propyl]-2-(dimethylamino)propane-1,3-diol.

Polymeric Photoinitiators

In one aspect of the invention the polymeric photoinitiators, being co-polymers of at least one monomer (A) with at least one monomer (B), the monomer (A) is a photoinitiator monomer of the general formula (I), with either subformulas (II), (III), or (IV), or formulas (IIa), (IIb), (IIIa), (IIIb), (IIIc), (IIId), (IVa), (IVb), or (IVc), all of which is within the scope of general formula (I):

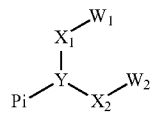

(I)

wherein general formula (I), including preferred options, is as defined herein for the photoinitiator monomers of general formula (I).

Accordingly, the definitions of Pi, Z, Za, Zb, Zc, $X_1$, $X_2$, $W_1$, $W_2$ $R^1$, $R^2$, $R^3$, $R^4$, $R^5$, $R^6$, $R^7$ and $R^8$ as described herein in connection with the photoinitiator monomers of formula (I) of the invention and the second aspect of the invention, applies for the polymeric photoinitiators of the invention and the first aspect of the invention as well. Polymerization of the polymeric photoinitiator is achieved by step-growth co-polymerization of monomers (A) and (B). The physical, chemical and photocatalytic properties of the polymeric photoinitiator can be varied depending on the nature and relative amounts of the monomers (A) and (B).

The other component of the polymeric photoinitiator is at least one monomer (B). Monomer (B) comprises at least two functional groups $W_3$ and $W_4$, said $W_3$ and $W_4$ being independently selected from —OH (i.e. forming a secondary alcohol), —CH$_2$OH, —NH$_2$, —NHR$^{11}$, —SH, —Si(OR$^{11}$)$_2$—H, —C(=O)—OSi(R$^{11}$)$_3$, —NCO, —NCS, —COOH, —COOR$^{11}$, —COO-aryl, —C(=O)—Cl, —O—C(=O)—Cl, —C(O)—NH$_2$, —C(O)—NHR$^{10}$, —NH—C(O)—OR$^{11}$, and —OC(O)—NHR$^{11}$, wherein R$^{10}$ is H or C$_1$-C$_6$ alkyl, and wherein R$^{11}$ is C$_1$-C$_6$ alkyl. Preferred options of R$^{10}$ and R$^{11}$ are as described herein for R$^7$ and R$^8$, mutatis mutandis.

In the above definition of W$_3$ and W$_4$ further details about the moieties —OH (forming a secondary alcohol), —CH$_2$OH, —NH$_2$, and —NHR$^4$ may be found in relation to W$_1$ and W$_2$, mutatis mutandis. The definitions and details are analogous.

Monomer (B) may have a structure of formula (VI):

$$W_3\text{-}Q\text{-}W_4 \quad (VI)$$

wherein W$_3$ and W$_4$ are defined above and wherein Q is selected from the group consisting of optionally substituted C$_1$-C$_{12}$ alkylene, optionally substituted C$_2$-C$_{12}$ alkenylene, optionally substituted C$_3$-C$_8$ cycloalkyl, optionally substituted C$_3$-C$_{12}$ heterocyclyl, optionally substituted aryl, optionally substituted biaryl, —[O—(C$_1$-C$_{12}$ alkylene)]$_m$-, —[S—(C$_1$-C$_{12}$ alkylene)]$_m$-, where m is an integer from 1-1000 and combinations thereof. Q could also comprise one of the photoinitiator moieties (Pi) set out above.

As an example, Q may for instance be a dicyclohexylmethylene and would then, in the above definition correspond to a (C$_3$-C$_8$ cycloalkyl)-(C$_1$-C$_{12}$ alkylene)-(C$_3$-C$_8$ cycloalkyl) moiety.

Q may be selected from the group consisting of optionally substituted C$_1$-C$_{12}$ alkylene, optionally substituted C$_2$-C$_{12}$ alkenylene, optionally substituted C$_3$-C$_8$ cycloalkyl, optionally substituted C$_3$-C$_{12}$ heterocyclyl, optionally substituted aryl, optionally substituted biaryl and combinations thereof.

Q may be selected from the group consisting of optionally substituted C$_1$-C$_{12}$ alkylene, optionally substituted C$_2$-C$_{12}$ alkenylene, optionally substituted C$_3$-C$_8$ cycloalkyl, optionally substituted C$_3$-C$_{12}$ heterocyclyl, optionally substituted aryl, and optionally substituted biaryl. Q may be selected from the group consisting of optionally substituted aryl and optionally substituted biaryl.

Preferably W$_3$ and W$_4$ may each independently be selected from isocyanate and thioisocyanate groups (i.e. —NCO and —NCS). Preferably W$_3$ and W$_4$ may be the same functional groups.

In particular embodiments, monomer (B) is a polyisocyanate, preferably a diisocyanate. Suitable polyisocyanates have an average of about two or more isocyanate groups, preferably an average of about two to about four isocyanate groups and include aliphatic, cycloaliphatic, aralkyl and aromatic polyisocyanates, used alone or in mixtures of two or more. Diisocyanates are preferred, this is for example the case where the polymeric photoinitiator is a polyurethane.

Specific examples of suitable aliphatic polyisocyanates include alpha, omega-alkylene diisocyanates having from 5 to 20 carbon atoms, such as hexamethylene-1,6-diisocyanate, 1,12-dodecane diisocyanate, 2,2,4-trimethyl-hexamethylene diisocyanate, 2,4,4-trimethyl-hexamethylene diisocyanate, 2-methyl-1,5-pentamethylene diisocyanate and the like. Polyisocyanates having fewer than 5 carbon atoms can be used but are less preferred because of their high volatility and toxicity. Preferred aliphatic polyisocyanates include hexamethylene-1,6-diisocyanate, 2,2,4-trimethyl-hexamethylene-diisocyanate and 2,4,4-trimethyl-hexamethylene diisocyanate.

Specific examples of suitable cycloaliphatic polyisocyanates include dicyclohexylmethane diisocyanate, isophorone diisocyanate, 1,4-cyclohexane diisocyanate, 1,3-bis-(isocyanatomethyl) cyclohexane and the like. Preferred cycloaliphatic polyisocyanates include dicyclohexylmethane diisocyanate and isophorone diisocyanate.

Specific examples of suitable araliphatic polyisocyanates include m-tetramethyl xylylene diisocyanate, p-tetramethyl xylylene diisocyanate, 1,4-xylylene diisocyanate, 1,3-xylylene diisocyanate, and the like. A preferred araliphatic polyisocyanate is tetramethyl xylylene diisocyanate.

Examples of suitable aromatic polyisocyanates include 4,4'-diphenylmethylene diisocyanate, toluene diisocyanate, their isomers, naphthalene diisocyanate and the like. A preferred aromatic polyisocyanate is toluene diisocyanate.

Monomer (B) may be selected from the group consisting of: 1,4-phenylene diisocyanate (PPDI), toluene diisocyanate (TDI) as both its 2,4 and 2,6 isomers, methylene diphenyl diisocyanate (MDI) as both its 4,4' and 2,4' isomers, 1,5-naphthalene diisocyanate (NDI), 3,3'-bitolylene-4,4'-diisocyanate (TODI), 1,3-xylylenediisocyanate (XDI), tetramethyl-m-xylidene diisocyanate (TMXDI), 1,6-hexamethylene diisocyanate (HDI), isophorone diisocyanate (IPDI), bis(4-isocyanatocyclohexyl)methane (HMDI), 2,2,5-trimethylhexane diisocyanate (TMHDI), 1,4-cyclohexane diisocyanate (CHDI) and 1,3-bis(isocyanato-methyl)cyclohexane (HXDI).

Importantly, W$_1$, W$_2$, W$_3$ and W$_4$ are selected such that—in the co-polymerization of monomers (A) and (B)—W$_1$ reacts with W$_3$ to form a urethane, thiourethane, urea, thiourea, ester, ether, amide, carbonate, allophanate or biuret moiety, and W$_2$ reacts with W$_4$ to form a urethane, thiourethane, urea, thiourea, ester, ether, amide, carbonate, allophanate or biuret moiety. In a preferred embodiment of the second aspect of the invention W$_1$ reacts with W$_3$ to form a urethane, thiourethane, urea, thiourea, ester or amide moiety, and W$_2$ reacts with W$_4$ to form a urethane, thiourethane, urea, thiourea, ester or amide moiety. Of most interest is the situation in which W$_1$ reacts with W$_3$ to form a urethane, or thiourethane moiety, and W$_2$ reacts with W$_4$ to form a urethane or thiourethane moiety.

Given a particular W$_1$ or W$_2$, the skilled person will be able to select the appropriate W$_3$ or W$_4$ to provide the polymeric photoinitiators of the invention.

Preferably, the polymeric photoinitiator is a polyurethane photoinitiator. In this case, W$_1$ and W$_2$ are selected to be alcohol functional groups, and W$_3$ and W$_4$ are selected as isocyanate groups to provide urethane moieties when monomer (A) reacts with monomer (B). A polyurethane photoinitiator will thus be formed. The reverse arrangement (W$_1$ and W$_2$ are isocyanate functional groups, while W$_3$ and W$_4$ are alcohol groups) will also provide a polyurethane. In this case in a preferred embodiment of monomer (A) W$_1$ and W$_2$ are selected so as both the alcohol functional groups are either primary (—CH$_2$OH) or secondary alcohol (i.e. —OH in the definition of W$_1$ and W$_2$) groups.

Similarly, if W$_1$ and W$_2$ are thiol functional groups, selection of W$_3$ and W$_4$ as isocyanate groups will provide thiourethane moieties when monomer (A) reacts with monomer (B). The reverse arrangement is also possible.

To form urea moieties from W$_1$-W$_4$, it is possible to select W$_1$ and W$_2$ as amine functional groups and W$_3$ and W$_4$ as isocyanate functional groups. Polyurea photoinitiators will thus be formed. The reverse situation is also possible (W$_1$ and W$_2$ are isocyanate functional groups, while W$_3$ and W$_4$ are amine functional groups). In this case in a preferred embodiment of monomer (A), W$_1$ and W$_2$ are selected so as both the amine functional groups are either primary or secondary amine groups.

Suitably, $W_3$ and $W_4$ are the same functional groups, as are $W_1$ and $W_2$. However, it is possible that $W_1$ and $W_2$ are different, as long as $W_3$ and $W_4$ are selected such that a polymer may be formed.

More than one type of monomer (A) and more than one type of monomer (B) may be used in the polymeric photoinitiators of the invention. As well as the regular structure . . . ABABABAB . . . , the polymeric photoinitiators may therefore also have a structure which incorporates variations of monomers A and B, e.g. . . . A'BABA'B'A'B'A'BABA'B' . . . .

One or more additional monomers (C) may also be present in the polymeric photoinitiators of the invention. Each of said one or more additional monomers (C) comprises at least two functional groups $W_5$ and $W_6$, said $W_5$ and $W_6$ being independently selected from —OH (i.e. forming a secondary alcohol), —CH$_2$OH, —NH$_2$, —NHR$^{13}$, —SH, —Si(OR$^{13}$)$_2$—H, —C(=O)—OSi(R$^{13}$)$_3$, —NCO, —NCS, —COOH, —COOR$^3$, —COO-aryl, —C(=O)—Cl, —O—C(=O)—Cl, —C(O)—NH$_2$, —C(O)—NHR$^{12}$, —NH—C(O)—OR$^{12}$, and —OC(O)—NHR$^{12}$, wherein R$^{12}$ is H or $C_1$-$C_6$ alkyl, and wherein R$^{13}$ is $C_1$-$C_6$ alkyl; and wherein $W_5$ and $W_6$ are selected such that—in the co-polymerization of monomers (A), (B) and (C)—$W_5$ reacts with $W_1$ or $W_3$ to form a urethane, thiourethane, urea, thiourea, ester, ether, amide, carbonate, allophanate or biuret moiety, and $W_6$ reacts with $W_2$ or $W_4$ to form a urethane, thiourethane, urea, thiourea, ester, ether, amide, carbonate, allophanate or biuret moiety. Suitably, $W_5$ reacts with $W_1$ or $W_3$ to form a urethane, thiourethane, urea, thiourea, ester or amide moiety, and $W_6$ reacts with $W_2$ or $W_4$ to form a urethane, thiourethane, urea, thiourea, ester, or amide moiety. Preferred options of R$^{12}$ and R$^{13}$ are as described herein for R$^7$ and R$^8$, mutatis mutandis.

In one embodiment of the invention, where one or more additional monomers (C) are present, these may be a macromonomer selected from polyether, polyester, polycarbonate, polyamine, and polydisulfide having the herein above or below described two functional groups $W_5$ and $W_6$. Suitably, polyether macromonomer (C) may be of a molecular weight between 200 and 20,000, more suitably between 200 and 15,000, even more suitably between 200 and 10,000, yet even more suitable between 1000 and 8,000, such as e.g. a polyethylene glycol (PEG), polypropylene glycol (PPG), random or block poly(ethylene glycol)-poly(propylene glycol) copolymer or poly(tetramethylene glycol) (PTMG). Suitably, polyester macromonomer (C) may be of a molecular weight between 200 and 10,000, such as e.g. 200 and 8,000, these being e.g. diol end-capped poly(1,4-butanediol adipate), poly(ethanediol 1,4-butanediol adipate), poly(caprolacton)diol or poly(ethylene terephthalate)diol. Suitably, polycarbonate macromonomer (C) may be of a molecular weight between 500 and 10,000, such as e.g. poly(hexamethylene carbonate)diol. Suitably, polyamine macromonomer (C) may be of a molecular weight between 500 and 10,000, such as e.g. a hydroxyl end-functionalised poly(2-methyl-2-oxazoline). Suitably, polydisulfide macromonomer (C) may be of a molecular weight between 1000 and 10,000, such as e.g. Thiokol® LP thiol end-capped polymer (e.g. Thiokol® LP-32 or Thiokol® LP-33).

Depending on the choice of $W_5$ and $W_6$, and the relative amounts of monomers (A), (B) and (C), the polymeric photoinitiator may have a variety of repeating structures such as e.g.:
 . . . ABABABABCBABABCBAB . . . (if $W_5$ and $W_6$ react with $W_3$ and $W_4$)
 . . . ABABACACABABABACAC . . . (if $W_5$ and $W_6$ react with $W_1$ and $W_2$)

Monomer (C) may have a structure of formula (VII):

$$W_5\text{-T-}W_6 \qquad \text{(VII)}$$

wherein $W_5$ and $W_6$ are defined above, and wherein T is selected from the group consisting of optionally substituted $C_1$-$C_{12}$ alkylene, optionally substituted $C_1$-$C_{12}$ alkenylene, optionally substituted $C_3$-$C_8$ cycloalkyl, optionally substituted $C_3$-$C_{12}$ heterocyclyl, optionally substituted aryl, optionally substituted biaryl, —[O—($C_1$-$C_{12}$ alkylene)]$_n$-, —[S—($C_1$-$C_{12}$ alkylene)]$_n$-, where n is an integer from 1-1000, and combinations thereof. T may be selected from the group consisting of —[O—($C_1$-$C_{12}$ alkylene)]$_m$-, —[S—($C_1$-$C_{12}$ alkylene)]$_m$-, where m is an integer from 1-1000.

Suitably, $W_5$ and $W_6$ are independently selected from —OH, —CH$_2$OH, —NH$_2$, —NHR$^{13}$, and —SH, preferably —OH or —CH$_2$OH. Typically, $W_5$ and $W_6$ are the same functional groups. In one embodiment of the invention where monomer C is a polyether macromonomer, one of $W_5$ and $W_6$ are —OH (forming a secondary alcohol), and the other is —CH$_2$OH (forming a primary alcohol).

Monomer (C) may be used to determine the physical properties of the polymeric photoinitiator. Monomer (C) may e.g. promote water solubility. Suitably, monomer (C) may be a macromonomer, i.e. a polymer or oligomer that has a functional group that can take part in further polymerization. As such, monomer (C) may be selected from the group consisting of: polyethylene glycol (PEG), polypropylene glycol (PPG), random and block poly(ethylene glycol)-poly(propylene glycol) copolymers, poly(tetramethylene glycol) (PTMG), poly(1,4-butanediol adipate), poly(ethanediol 1,4-butanediol adipate), poly(caprolacton)diol, poly(1,6-hexanediol carbonate) and poly(ethylene terephthalate)diol. Monomer (C) may also comprise diols of other poly($C_1$-$C_6$) alkylene oxides.

Monomer (C) could also be a low molecular weight monomer, such as a $C_1$-$C_{10}$ diol, e.g. 1,2-ethanediol, 1,3-propanediol or 1,4-butanediol.

The weight ratio of monomers (A):(B) is suitably 1:99-99:1, preferably 1:99-50:50. The weight ratio of monomers (A):(C) is suitably 1:99-99:1, preferably 1:99-50:50. The weight of the photoinitiator monomer (A) used to prepare polymeric photoinitiators may be between 0.1% and 99% of the total mass of other monomers, suitably between 0.2% and 10%, most suitably 0.5% to 5%.

Suitably, the polymeric photoinitiator has a molecular weight of more than 1 kDa, suitably between 10 kDa and 1000 kDa, most suitably between 20 kDa and 100 kDa.

In the polymeric photoinitiator, the photoinitiator moiety Pi is pendant on the polymer backbone. As such, it is not able to leach from the polymer matrix. In addition, radical bond-forming reactions between the photoinitiator moiety and other components of the polymerization mixture will cause cross-linking, rather than forming undesirable low molecular weight compounds.

One or more additional monomers (D) may also be present in the polymeric photoinitiators of the invention. Monomer (D) may be selected from R$^{18}$—PCl$_2$, Ar$_3$—PCl$_2$, R$^{18}$—P(=O)Cl$_2$, Ar$_3$—P(=O)Cl$_2$, R$^{18}$—O—P(=O)Cl$_2$, Ar$_3$—O—P(=O)Cl$_2$, wherein R$^{18}$ is optionally substituted $C_1$-$C_{12}$ alkyl and Ar$_3$ is optionally substituted aryl. Examples of such monomers include, but are not limited to, phenyldichlorophosphine (C$_6$H$_5$—PCl2), methyphosphonic dichloride (CH$_3$—P(=O)Cl$_2$) and methyl dichlorophosphate (CH$_3$—O—P(=O)Cl$_2$). These monomers (D) may be used in preparing polymeric photoinitiators of the invention by co-polymerization with monomer (A) alone or together with other monomers (B) or (C), such as are described herein in relation to the second aspect of the invention. Monomers (D) may furthermore be used in polymeric photoinitiators of the invention incorporated into a polyacrylate according to the third aspect of the invention. Monomers (D) are suitable for making polyphosphonites, polyphosphonates and polyphosphates.

Further Aspects of the Invention Relating to Polymeric Photoinitiators

The invention further relates to a method for producing a polymeric photoinitiator, said method comprising step-growth co-polymerization of at least one monomer (A) with at least one monomer (B), wherein (A) and (B) have the structures described above. Preferably the polymeric photoinitiator is a polyurethane photoinitiator. The co-polymerization reaction may additionally comprise one or more additional monomers (C), having the structure described above. Co-polymerization of monomers (A) and (B) may take place using any suitable reaction conditions, catalysts or reagents known to the skilled person.

The polymeric photoinitiators (e.g. polyurethane photoinitiators) of the present invention form radical species upon exposure to radiation and/or heat. Application of radiation (as described in the section above entitled "Curing") excites the photoinitiator moiety, Pi, which then extracts protons from neighbouring functionalities, forming reactive radicals.

If the polymeric photoinitiator is the only component when irradiated, it will cross-link with itself, providing a cured polymer. The invention thus provides a method of cross-linking the polymeric photoinitiator of the invention, said method comprising exposing the polymeric photoinitiator as described herein to UV radiation and/or heat.

If the polymeric photoinitiator of the invention is mixed with monomers which can undergo radical polymerization (e.g. alkene monomers or acrylate monomers), rapid curing (=polymerization and cross-linking) of such monomers can occur. The present invention thus provides the use of a polymeric photoinitiator as described herein as a photoinitiator of radical polymerization.

It has been found that the polymeric photoinitiators of the present invention act to cure polymer matrices, at least as effectively, if not more effectively than known photoinitiators.

Additionally, in a further aspect the present invention relates to use of a photoinitiator monomers of formula (I), including those of the second aspect of the invention of formula (I), or subformulas thereof, in preparation of a polymeric photoinitiator. When used in this manner the photoinitiator monomers of formula (I) becomes incorporated by covalent bonds as monomers into the polymer via the two functional groups ($W_1$ and $W_2$). Accordingly, the present invention provides the use of photoinitiator monomers of formula (I) for incorporation as monomers into a polymer backbone via the functional groups $W_1$ and $W_2$. Preferably, said polymer may be a polyurethane, such as e.g. a polyalkyletherurethane, a polyurea, a polythiourethane, a polythiourea, a polydithiourethane, a polyester, a polycarbonate, a polyphosphonite, a polyphosphonate, or a polyphosphate; more preferably said polymer may be a polyurethane, a polyurea, a polyester, or polycarbonate; even more preferably a polyurethane, a polyurea, or a polyester; and yet even more preferably a polyurethane, such as e.g. a polyalkyletherurethane. Further details about the different types of polymers, or suitable $W_1$ and $W_2$ groups for such types of polymers, are described herein elsewhere and applies in full for this aspect of the invention.

Polyacrylate Polymers

A further aspect of the present invention provides a polyacrylate. A polyacrylate is a polymer based on acrylate monomers (Ac) comprising the moiety C=C—C(=O)—O—, which polymerize at the alkene functional group.

The polyacrylate is obtained by radical polymerization of at least one acrylate monomer (Ac) in the presence of a polymeric photoinitiator. The polymeric photoinitiator is a co-polymer of at least one monomer (A) with at least one monomer (B):

monomer (A) is a photoinitiator monomer of general formula (I):

wherein general formula (I), or subformulas (II), (III), or (IV), or formulas (IIa), (IIb), (IIIa), (IIIb), (IIIc), (IIId), (IVa), (IVb), or (IVc), including preferred options of these, is as defined herein, including those of the second aspect of the invention, i.e. photoinitiator monomers of general formula (I); and monomer (B) is as defined herein for the first aspect of the invention.

wherein—in the co-polymerization of monomers (A) and (B) in the polymeric photoinitiator—$W_1$ reacts with $W_3$ to form a urethane, thiourethane, urea, thiourea, ester or amide moiety, and $W_2$ reacts with $W_4$ to form a urethane, thiourethane, urea, thiourea, ester or amide moiety.

Accordingly, the definitions of Pi, Z, Za, Zb, Zc, $X_1$, $X_2$, $W_1$, $W_2$ $R^1$, $R^2$, $R^3$, $R^4$, $R^5$, $R^6$, $R^7$ and $R^8$, as described herein in connection with the photoinitiator monomers of the invention, applies for the third aspect of the invention as well. Additionally the definitions of monomer (B), (C), and (D), and preferred options of these, together with the polymeric photoinitiator, including those of the first aspect of the invention, apply for the third aspect of the invention mutatis mutandis. For example in a preferred embodiment both $W_1$ and $W_2$ are alcohol functional groups and both $W_3$ and $W_4$ are isocyanate functional groups.

Polymerization is achieved by step-growth co-polymerization of monomers (A) and (B). The physical, chemical and photocatalytic properties of the polymeric photoinitiator can be varied depending on the nature and relative amounts of the monomers (A) and (B).

In the polymeric photoinitiator, the photoinitiator moiety Pi is pendant on the polymer backbone. As such, it is not able to leach from the polymer matrix or the polyacrylate. In addition, radical bond-forming reactions between the photoinitiator moiety and the acrylate monomer (Ac) will cause cross-linking between these components, rather than forming undesirable low molecular weight compounds.

The polymeric photoinitiators (e.g. polyurethane photoinitiators) form radical species upon exposure to radiation and/or heat. Application of radiation (as described in the section above entitled "Curing") excites the photoinitiator moiety, Pi, which then extracts protons from neighbouring functionalities, forming reactive radicals.

When the polymeric photoinitiator of the invention is mixed with acrylate monomers (Ac), these reactive radicals undergo chain propagation with the acrylate monomers (Ac), and rapid curing of such monomers can occur. As growth is initiated from the polymeric photoinitiator, the polymeric photoinitiator will itself be incorporated by means of covalent bonds into the growing polyacrylate.

The acrylate monomer (Ac) used in the invention may be a mono-, di- or tri-acrylate (i.e. comprising one, two or three C=C—C(=O)—O— moieties, respectively, or the corresponding N derivative C=C—C(=O)—N—). Preferably, the acrylate monomer is a mono-acrylate.

Examples of acrylate monomers (Ac) useful in the present invention include ethylenically unsaturated monocarboxylic and dicarboxylic acids, such as acrylic acid, methacrylic acid, itaconic acid, maleic acid and fumaric acid, and monoalkyl esters of dicarboxylic acids of the type mentioned above with alkanols, preferably alkanols having from 1 to 4 carbon atoms and their N-substituted derivatives (amides), amides of unsaturated carboxylic acids, such as acrylamide, methacrylamide, N-methoxyacrylamide or methacrylamide, and N-alkylacrylamides, ethylenic monomers containing a sulphonic acid group and ammonium or alkali metal salts thereof, for example vinylsulphonic acid, vinylbenzenesulphonic acid, alpha-acrylamidomethylpropanesulphonic acid and 2-sulphoethylene methacrylate, amides of vinylamine, especially vinylformamide or vinylacetamide, and unsaturated ethylenic monomers containing a secondary, tertiary or quaternary amino group, or a heterocyclic group containing nitrogen, such as, for example, vinylpyridines, vinylimidazole, aminoalkyl(meth)acrylates and aminoalkyl(meth)acrylamides such as dimethylaminoethyl acrylate or methacrylate, di-tert-butylaminoethyl acrylate or methacrylate, dimethylaminoacrylamide or dimethylaminomethacrylamide, and 2-{[2-(acryloyloxy)ethyl](dimethyl)ammonio}ethane-sulfonate.

In addition to the above (meth)acrylates with a hydrophilic pendant chain such as poly(ethylene glycol) methyl ether acrylate may be useful.

Examples of difunctional acrylate monomers useful in the present invention include oligomers having two acrylate, methacrylate, acrylamide, or methacrylamide groups. Each of these monomers may comprise the same two functional groups or different functional groups. The difunctional acrylate monomers may preferably be selected from bisphenol A dimethacrylate, ethoxylated bisphenol A diacrylates (e.g., ethoxylated bisphenol A diacrylate with EO/phenol 1.0, 1.5, 2, 4, 10 or 15), ethoxylated bisphenol A dimethacrylates (e.g., ethoxylated bisphenol A dimethacrylate with EO/phenol 2 or 15), bisphenol A glycerolate dimethacrylate (e.g., bisphenol A glycerolate dimethacrylate with glycerol/phenol 1), polyethylene glycol diacrylates (e.g., polyethylene glycol diacrylate with average $M_n$ of 250, 575, 700, 1000, 2000, 6000 and 10000), ethylene glycol dimethacrylate, diethylene glycol dimethacrylate, triethylene glycol dimethacrylate, tetraethylene glycol dimethacrylate, polyethylene glycol dimethacrylates (e.g., polyethylene glycol dimethacrylate with average $M_n$ of 330, 550, 750, 2000, 6000 and 10000), dipropyleneglycol diacrylate, tripropyleneglycol diacrylate, polypropylene glycol diacrylates (e.g., polypropylene glycol diacrylate with $M_n$ of 800), dipropylene glycol dimethacrylate, tripropyleneglycol dimethacrylate and polypropylene glycol dimethacrylates (e.g., polypropylene glycol dimethacrylate with $M_n$ of 560), tetramethylene dimethacrylate, methylenebisacrylamide, methacryloxyethyl vinyl carbonate, methacryloxyethyl vinyl urea, divinyl benzene, diallyl itaconate, allyl methacrylate, diallyl phtalate, and polysiloxanylbisalkyl methacrylate. $M_n$ is number average molecular weight value. It is defined as arithmetic mean of the molecular weights of the individual macromolecules.

Suitable di- or multifunctional cross-linking agents may be, but not being limited to, ethylene glycol dimethacrylate, triethylene glycol dimethacrylate, tetraethylene glycol dimethacrylate, trimethylopropane trimethacrylate, bisphenol A dimethacrylate, ethoxylate bisphenol A dimethacrylate, pentaerythritol tri- and tetrametacrylate, tetramethylene dimethacrylate, methylenebisacrylamide, methacryloxyethyl vinyl carbonate, triallylcyanurate, methacryloxyethyl vinyl urea, divinyl benzene, diallyl itaconate, allyl methacrylate, diallyl phtalate, polysiloxanylbisalkyl methacrylate and polyethylene glycol dimethacrylate.

Examples of multifunctional acrylate monomers useful in the present invention include oligomers having three or more acrylate, methacrylate, acrylamide, or methacrylamide groups. Each of these monomers may comprise the same two functional groups or different functional groups. The multifunctional acrylate monomers may preferably be selected from trimethylolpropane triacrylate, trimethylolpropane ethoxylate triacrylate (e.g., trimethylolpropane ethoxylate triacrylate with average $M_n$ of 400, 700 or 900), trimethylolpropane propoxylate triacrylate, trimethylopropane trimethacrylate, pentaerythritol triacrylate, pentaerythritol propoxylate triacrylate, glycerol propoxylate triacrylate, triallylcyanurate, pentaerythritol tetraacrylate, pentaerythritol tetramethacrylate, di(trimethylolpropane)tetraacrylate, dipentaerythritol pentaacrylate and dipentaerythritol hexaacrylate.

Oligo- or macromeric structures of a non-toxic nature are preferred. Of these, PEG containing di- or multifunctional oligo- or macromers may be of special interest. In the present invention, polyethylene glycol dimethacrylate of an approximately molecular weight of 400 (PEG-DMA 400) and an approximately molecular weight of 1000 (PEG-DMA 1000) may be preferred as cross-linking agent. In one embodiment the acrylate monomer (Ac) comprises a polyurethane oligomer having terminal acrylate groups.

Suitably, the acrylate monomer (Ac) is an acrylate ester of the formula (VIII):

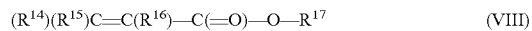

$$(R^{14})(R^{15})C=C(R^{16})-C(=O)-O-R^{17} \qquad (VIII)$$

wherein $R^{14}$-$R^{16}$ are independently selected from the group consisting of H, optionally substituted $C_1$-$C_{12}$ alkyl, optionally substituted $C_1$-$C_{12}$ alkenyl, optionally substituted $C_3$-$C_{12}$ heterocyclyl and optionally substituted aryl;

and $R^{17}$ is selected from the group consisting of optionally substituted $C_1$-$C_{12}$ alkyl, optionally substituted $C_1$-$C_{12}$ alkenyl, optionally substituted $C_3$-$C_{12}$ heterocyclyl and optionally substituted aryl.

Suitably, $R^{14}$ and $R^{15}$ are independently selected from H, methyl or ethyl.

Alternatively, the acrylate monomer (Ac) may comprise a polyurethane, a polyester or a polyether oligomer having terminal acrylate groups.

The polyacrylate of the invention may comprise two or more different acrylate monomers (Ac). Different acrylate monomers (Ac) can be mixed in various ratios, depending on the desired properties of the resulting polyacrylate.

The polyacrylate of the invention may comprise additional monomers. In this way, a copolymer of the acrylate monomer(s) (Ac) with other monomers may be obtained. For example, the polymeric photoinitiator of the invention may be used to initiate the copolymerization between acrylate monomers (Ac) and monomers such as vinylethers, vinylpyrrolidone and vinyllactams, vinyl acetates and vinylalcohol, vinylamines or mixtures of these. The additional monomers should be compatible with the acrylate monomers and the polymeric photoinitiator, and should polymerize via a radical-catalysed mechanism, so that they can be incorporated with the acrylate monomer (Ac). Such additional monomers provide the skilled person with further opportunities to vary the physical and chemical properties of the resulting polyacrylate.

The polymeric photoinitiators of the invention with the photoinitiator moieties incorporated as pendant groups on the polymeric backbone are capable of self-cross linking under UV light. In the presence of acrylate monomers (Ac), self-cross linking of original polymer chains and radical chain propagation of the acrylate monomers (Ac) take place. Particularly when suitable di- and/or multifunctional acrylate monomers are used, a densely cross-linked material is obtained that shows increased hardness.

Further Aspects of the Invention Relating to Polacrylates

The present invention further provides a method for producing a polyacrylate, said method comprising the steps of:
 a. combining one or more acrylate monomers with a polymeric photoinitiator, said polymeric photoinitiator being as defined herein;
 b. subjecting the mixture from step a. to UV radiation and/or heat.

The present invention also provides the use of a polymeric photoinitiator as described herein as a photoinitiator of radical polymerization of acrylate monomers (Ac).

Polymerization with Photoinitiator Monomers of Formula (I) or Photoinitiator Monomers (A)

Description of Polymerization Conditions

Polyurethanes, polythiourethanes and polydithiourethanes are typically prepared from their respective monomers in solvents or in bulk. For solvent-based procedures, the typical solvents include tetrahydrofuran, toluene and chlorobenzene at temperatures ranging from 20° C. to 100° C. Catalysts such as dibutyltin dilaurate (DBTDL) or 1,4-diazabicyclo[2.2.2]octane (DABCO) may be used to accelerate the reactions. Under bulk conditions, all components are reacted without solvent as a homogeneous reaction melt at temperatures typically between 50° C. to 120° C. Polyureas and polythioureas are typically prepared by analogous solvent-based or bulk procedures, but no catalyst is required since the polymerisation is typically very rapid at temperatures ranging from 20° C. to 100° C.

Polyurethane formation in the absence of a transition metal compound or a tertiary amine can be 10-500 times slower compared to the same reaction in the presence of a catalyst. The reaction times/reaction temperature can be increased accordingly to achieve the same degree of polymerisation. For general reference to polyurethane formation, see, for example, Encyclopedia of Polymer Science and Technology, John Wiley & Sons, Volume 4, p. 26.

Polyesters are typically prepared from their respective monomers in solvents such as toluene or xylenes in the presence of strong acid catalysts and with azeotropic removal of water or low molecular weight aliphatic alcohol by-product. Typical temperatures range from 80° C. to 150° C.

Polycarbonates are typically prepared in a solvent such as dichloromethane using a tertiary amine catalyst, while maintaining pH via the addition of NaOH. A melt transesterification process can also be used, which involves base-catalyzed reaction of a diol with diphenyl carbonate.

Polyphosphonites, polyphosphonates and polyphosphates are typically prepared from the appropriate phosophorus-based reagents bearing —$PCl_2$, —$P(=O)Cl_2$ or —O—$P(=O)Cl_2$ function group, respectively, and a diol. The reactions can be conveniently carried out in aromatic solvents such as toluene at temperatures ranging from 0° C. to 80° C. in the presence of tertiary amines.

A general scheme for the formation of polyurethanes of Formula (III) using photoinitiator monomers of Formula (I) is shown in Scheme 1 below:

Scheme 1:

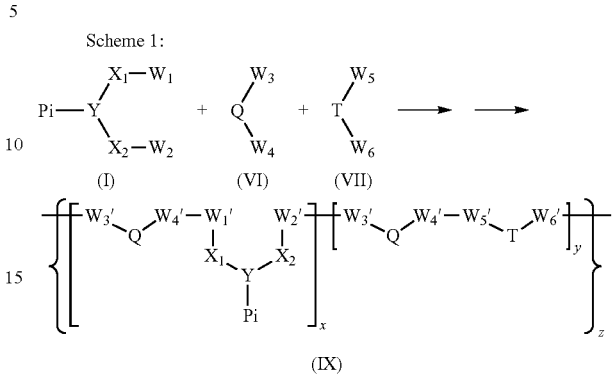

In Scheme 1, formulas (I), (VI), and (VII), and the preferred embodiment thereof are as described herein above. Formula (IX) is an example of a polymeric photoinitiator of the invention formed by co-polymerization of photoinitiator monomers of formula (I), for formation of for example a polyurethane. End groups $W_3$, $W_4$, $W_5$, $W_6$ are independently selected from the same end groups as $W_1$ and $W_2$. $W_3$ and $W_4$ are selected so as to be complementary to $W_1$, $W_2$, $W_5$ and $W_6$, so that urethane and urethane-like chains are formed. For instance, if the end groups $W_1$, $W_2$, $W_5$ and $W_6$ comprise alcohol, amine or thiol groups, suitable $W_3$ and $W_4$ will comprise isocyanate or isothiocyanate groups, and vice-versa.

Additional monomers may be introduced into the polyurethane according to the above scheme, as desired by the person skilled in the art. The additional monomers may be other photoinitiator monomers of Formula (I) or other monomers of Formula (VI) or Formula (VII).

The weight of the photoinitiator (I) used to prepare polyurethane polymer (IX) may be between 0.1% and 99% of the total mass of other monomers, suitably between 0.2% and 10%, most suitably 0.5% to 5%.

Suitably, the polymer, e.g. a polyurethane polymer, (IX) has a molecular weight of more than 1 kDa, suitably between 10 kDa and 1000 kDa, most suitably between 20 kDa and 100 kDa.

As set out above, the photoinitiator monomers of the present invention are incorporated into the polymer chain, as the end groups $W_1$, $W_2$, $W_5$ and $W_6$ react with the end groups $W_3$, $W_4$ of other monomers. The nomenclature $W_1'$, $W_2'$, $W_3'$, $W_4'$, $W_5'$ and $W_6'$ depict the corresponding end groups $W_1$-$W_6$ after being reacted.

The photoinitiator moiety therefore becomes pendant from the polymer backbone. As such, it is not able to leach from the polymer matrix. In addition, radical bond-forming reactions between the photoinitiator moiety and other components of the polymerization mixture will cause cross-linking, rather than forming undesirable low molecular weight compounds.

In addition, polyurethane films comprising the polymeric photoinitiators of the present invention exhibit good adhesion in film form to hydrophobic surfaces, such as polypropylene, or other polyurethane containing materials. Accordingly, the polymeric photoinitiators of the present invention may preferably be polyurethanes.

The following synthesis schemes show synthetic routes to photoinitiator monomers of structure (Vd).

Scheme 2:
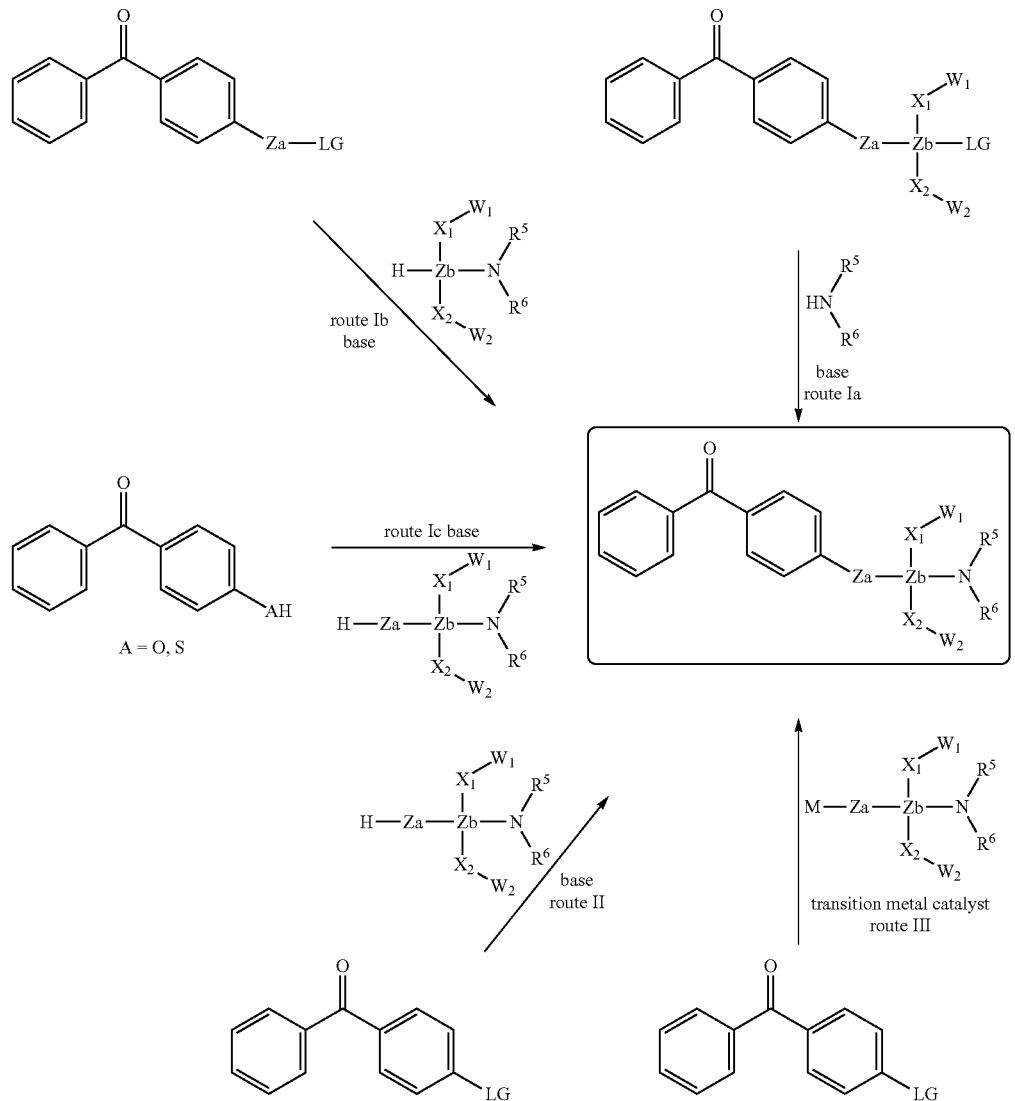
Scheme 2 depicts 5 different routes of synthesis for compounds of formula (IIIc), wherein Pi is benzophenone.
Scheme 3:
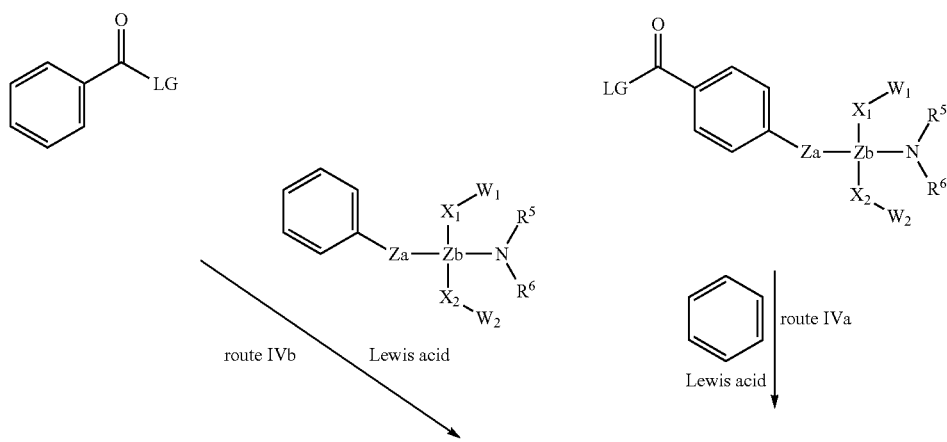

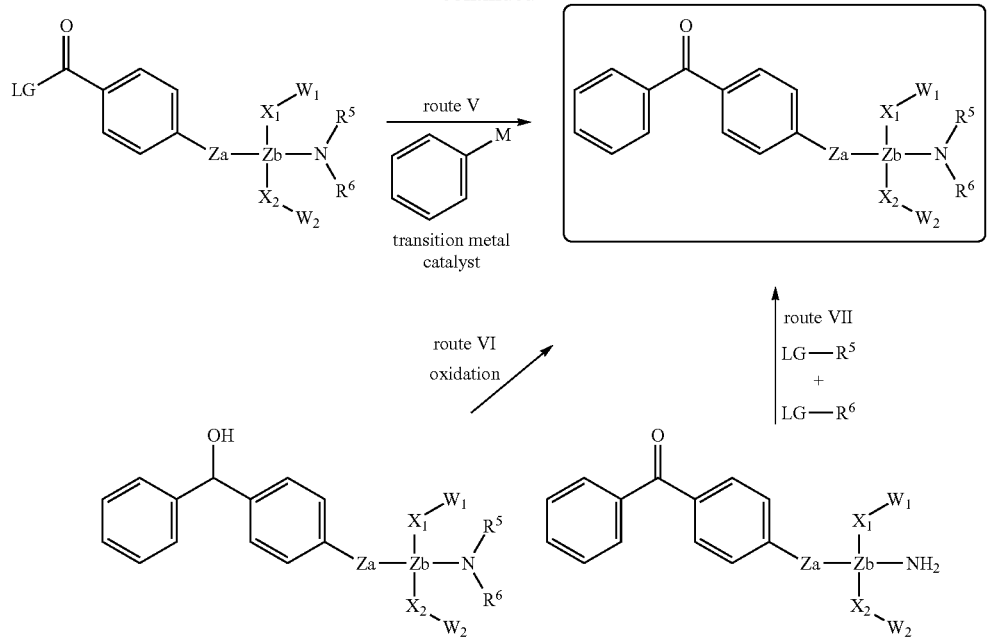
Scheme 3 depicts five additional routes of synthesis for photoinitiator monomers of formula (IIIc), wherein Pi is a benzophenone moiety.
Scheme 4:
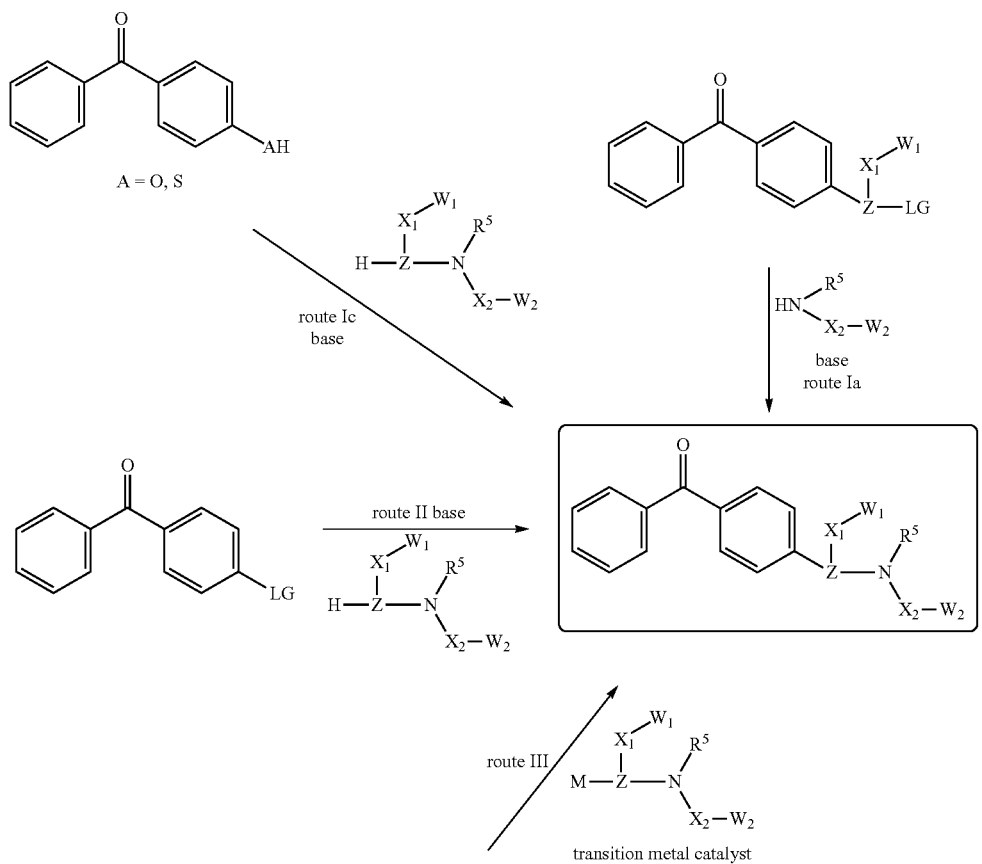

-continued

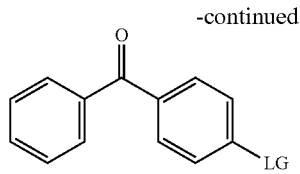

Scheme 4 depicts four different routes of synthesis for photoinitiator monomers of formula (IIb), wherein Pi is a benzophenone moiety.

In the above Schemes 2, 3 and 4, routes Ia, Ib and Ic are nucleophilic substitution, or carbonyl group transformation (i.e. nitrogen acylation). LG depicts a leaving group (preferably Cl, Br, I, OMs, OTs, OTf). The base used is preferably tertiary amine, alkali metal alkoxide, hydroxide or carbonate. These reactions are typically carried out in polar solvents such as tetrahydrofuran, dioxane, dimethylformamide or dichloromethane at temperatures typically ranging from 0° C. to 80° C.

Route II is a nucleophilic aromatic substitution. LG depicts a leaving group (preferably F, Cl). The base is preferably amine, alkali metal alkoxide, hydroxide or carbonate. These reactions are typically carried out in high boiling solvents such as toluene, xylenes, dimethylformamide or diphenyl ether at temperatures typically ranging from 50° C. to 150° C.

Route III is a cross-coupling reaction. LG depicts a leaving group (preferably Cl, Br, I, OMs, OTs, OTf). M depicts a nucleophilic organometallic substituent (preferably $R_2Al$—, $RZn$—, $R_3Sn$—, $RMg$—, $Li$—, $(RO)_2B$—). The transition metal catalyst is a salt or transition metal complex (preferably containing Pd, Pt, Ni, Ir, Rh, Ru, Cu, Fe). These reactions are typically carried out in non-polar aprotic solvents such as toluene or tetrahydrofuran at temperatures typically ranging from 20° C. to 60° C. Cross-coupling reactions with boron-based organometallic reagents are conveniently carried out in aqueous solvents such as tetrahydrofuran-water.

Routes IVa and IVb are Friedel-Crafts acylations. The Lewis acid may be preferably $BF_3$, $BCl_3$, $AlCl_3$, $FeCl_3$ or $SnCl_4$. These reactions are typically carried out medium polarity solvents such as dichloromethane, benzene or nitrobenzene at temperatures typically ranging from 0° C. to 80° C.

Route V may be a reaction of an aryl organometallic reagent with an acyl derivative. M depicts a nucleophilic organometallic substituent (preferably $RMg$—, $RZn$—, $RCd$— or $R_3Sn$—). These reactions are typically carried out in non-polar aprotic solvents such as toluene or tetrahydrofuran at temperatures typically ranging from 20° C. to 60° C.

Route VI is oxidation of a diarylmethanol. Preferable oxidants include manganese, ruthenium, chromium reagents and Swern oxidation. These reactions are typically carried out in aprotic solvents such as dichloromethane, toluene, tetrahydrofuran or dimethylformamide at temperatures typically ranging from 0° C. to 50° C.

Route VII may be nitrogen alkylation or acylation. Suitably, one or both reagents LG-$R^5$ and LG-$R^6$ may contain an epoxide (aziridine) which is opened by the nucleophilic N-atom to reveal a reactive hydroxy (amino) end group. These reactions are typically carried out in polar solvents such as tetrahydrofuran, dioxane, dimethylformamide or dichloromethane at temperatures typically ranging from 0° C. to 80° C.

SPECIFIC EMBODIMENTS OF THE INVENTION

1. A photoinitiator of Formula (I):

wherein:
Pi is a photoinitiator moiety;
Y is selected from:

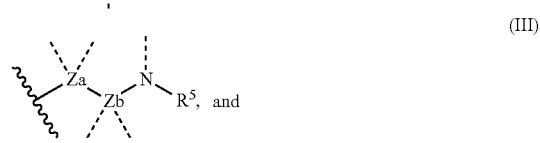

—$X_1$—$W_1$ and —$X_2$—$W_2$ are each independently attached to Y at either the N-atom or the —Z—, -Za-, -Zb-, or -Zc- linker, one or both of the —$X_1$—$W_1$ and —$X_2$—$W_2$ may be attached to the same linker moiety wherever it is chemically feasible; with the proviso that when the linker is either Z or -Za-Zb-, at least one of —$X_1$—$W_1$ and —$X_2$—$W_2$ is attached to an atom other than the N-atom;

when one of —$X_1$—$W_1$ or —$X_2$—$W_2$ is attached to the N-atom, said N-atom is substituted with $R^5$; when neither of —$X_1$—$W_1$ or —$X_2$—$W_2$ are attached to the N-atom, said N-atom is substituted with both $R^5$ and $R^6$;

Z is a linker moiety;

Za and Zb together form a linker in which Za is selected from optionally substituted —[O—($C_1$-$C_{12}$ alkylene)]$_n$-, optionally substituted —[$NR^2$—($C_1$-$C_{12}$ alkylene)]$_n$, and optionally substituted —[S—($C_1$-$C_{12}$ alkylene)]$_n$-, wherein Za is joined to Pi via the O, N or S atom in Za, and Zb is a linker moiety;

Zc is a linker moiety selected from —C(O)—($C_1$-$C_{12}$ alkylene)-, —C(O)—$CH_2$—($C_2$-$C_{12}$ alkenylene)-, —C(O)—O—($C_1$-$C_{12}$ alkylene)-, —C(O)—O—($C_2$-$C_{12}$ alkenylene)-, —C(O)—$NR^1$—($C_1$-$C_{12}$ alkylene)-, —C(O)—$NR^1$—($C_2$-$C_{12}$ alkenylene)-, —($C_1$-

$C_{12}$ alkylene)-C(O)—($C_1$-$C_{12}$ alkylene)-, —($C_1$-$C_{12}$ alkylene)-C(O)—O—($C_1$-$C_{12}$ alkylene)-, —($C_1$-$C_{12}$ alkylene)-O—C(O)—($C_1$-$C_{12}$ alkylene)-, —($C_1$-$C_{12}$ alkylene)-C(O)—NR—($C_1$-$C_{12}$ alkylene)-, —($C_1$-$C_{12}$ alkylene)-NR—C(O)—($C_1$-$C_{12}$ alkylene)-, —($C_1$-$C_{12}$ alkylene)-NH—C(O)—NH—($C_1$-$C_{12}$ alkylene)-, —NH—C(O)—NH—($C_1$-$C_{12}$ alkylene)-, and —[$NR^2$—($C_1$-$C_{12}$ alkylene)]$_n$-, wherein any alkylene or alkenylene moiety each independently is optionally substituted with one or more substituents;

$R^1$ is H or optionally substituted $C_1$-$C_{12}$ alkyl;

$R^2$ is optionally substituted $C_1$-$C_{12}$ alkyl;

n is an integer from 1-20;

$X_1$ and $X_2$ are each independently selected from optionally substituted $C_1$-$C_{12}$ alkylene, optionally substituted $C_2$-$C_{12}$ alkenylene, —O—, —S—, —$NR^4$—, —C(=O)—, —C(=$NR^3$)—, —Si($R^3$)$_2$—O—, optionally substituted $C_3$-$C_8$ cycloalkyl, optionally substituted heterocyclyl, optionally substituted aryl, and combinations thereof;

Z, Za, Zb, Zc, $X_1$ and $X_2$ are selected such that N is a tertiary amine;

$X_1$ and $X_2$, or a part thereof, may be linked to one another or to linkers Z, Za, Zb, or Zc to form one or more ring structures;

$R^3$ is H or optionally substituted $C_1$-$C_{12}$ alkyl;

$R^4$ is optionally substituted $C_1$-$C_{12}$ alkyl;

$R^5$ and $R^6$ are each independently selected from optionally substituted $C_1$-$C_6$ alkyl, wherein the carbon atom adjacent to the N-atom is in a —$CH_2$— moiety;

$W_1$ and $W_2$ are each independently selected from —OH, —$CH_2OH$, —$NH_2$, —$NHR^8$, —SH, —Si($OR^8$)$_2$—H, —C(=O)—OSi($R^8$)$_3$, —NCO, —NCS, —COOH, —$COOR^8$, —COO-aryl, —C(=O)—Cl, —O—C(=O)—Cl, —C(O)—$NH_2$, —C(O)—$NHR^7$, —NH—C(O)—$OR^7$, and —OC(O)—$NHR^7$;

$R^7$ is H or $C_1$-$C_6$ alkyl; and $R^8$ is $C_1$-$C_6$ alkyl.

2. A photoinitiator of Formula (I):

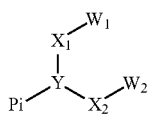

(I)

wherein:

Pi is a photoinitiator moiety;

Y is:

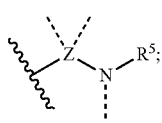

(II)

Z is a linker moiety;

—$X_1$—$W_1$ and —$X_2$—$W_2$ are each independently attached to Y at either the N-atom or the Z-linker, one or both of the —$X_1$—$W_1$ and —$X_2$—$W_2$ may be attached to the Z-linker wherever it is chemically feasible;

with the proviso that at least one of —$X_1$—$W_1$ and —$X_2$—$W_2$ is attached to an atom other than the N-atom;

when one of —$X_1$—$W_1$ or —$X_2$—$W_2$ is attached to the N-atom, said N-atom is also substituted with $R^5$;

when neither of —$X_1$—$W_1$ or —$X_2$—$W_2$ are attached to the N-atom, it is substituted with $R^5$ and $R^6$;

$X_1$ and $X_2$ are each independently selected from optionally substituted $C_1$-$C_{12}$ alkylene, optionally substituted $C_2$-$C_{12}$ alkenylene, —O—, —S—, —$NR^4$—, —C(=O)—, —C(=$NR^3$)—, —Si($R^3$)$_2$—O—, optionally substituted $C_3$-$C_8$ cycloalkyl, optionally substituted heterocyclyl, optionally substituted aryl, and combinations thereof;

Z, $X_1$ and $X_2$ are selected such that N is a tertiary amine;

$X_1$ and $X_2$, or a part thereof, may be linked to one another or to linker Z to form one or more ring structures;

$R^3$ is H or optionally substituted $C_1$-$C_{12}$ alkyl;

$R^4$ is optionally substituted $C_1$-$C_{12}$ alkyl;

$R^5$ and $R^6$ are each independently selected from optionally substituted $C_1$-$C_6$ alkyl, wherein the carbon atom adjacent to the N-atom is in a —$CH_2$— moiety;

$W_1$ and $W_2$ are each independently selected from —OH, —$CH_2OH$, —$NH_2$, —$NHR^8$, —SH, —Si($OR^8$)$_2$—H, —C(=O)—OSi($R^8$)$_3$, —NCO, —NCS, —COOH, —$COOR^8$, —COO-aryl, —C(=O)—Cl, —O—C(=O)—Cl, —C(O)—$NH_2$, —C(O)—$NHR^7$, —NH—C(O)—$OR^7$, and —OC(O)—$NHR^7$;

$R^7$ is H or $C_1$-$C_6$ alkyl; and $R^8$ is $C_1$-$C_6$ alkyl.

3. The photoinitiator according to any of the preceding embodiments, wherein Z is selected from the group consisting of optionally substituted $C_1$-$C_{12}$ alkylene, optionally substituted $C_2$-$C_{12}$ alkenylene, —O—, —S—, —$NR^2$—, —C(=O)—, —C(=O)—$NR^1$, —$NR^1$—C(=O)—, —C(=$NR^1$)—, —$SO_2$—, —P(=O)($OR^1$)—, optionally substituted —$C_3$-$C_8$ cycloalkyl, optionally substituted heterocyclyl, optionally substituted aryl, —[O—($C_1$-$C_{12}$ alkylene)]$_n$-, —[$NR^2$—($C_1$-$C_{12}$ alkylene)]$_n$-, —[S—($C_1$-$C_{12}$ alkylene)]$_n$-, and combinations thereof, wherein $R^1$ is H or optionally substituted $C_1$-$C_{12}$ alkyl, $R^2$ is optionally substituted $C_1$-$C_{12}$ alkyl, and n is an integer from 1-20.

4. The photoinitiator according to any of the preceding embodiments, wherein, in the definition of Z, n is an integer from 1-10, preferably from 1-5, more preferably from 1-2.

5. The photoinitiator according to any of the preceding embodiments, wherein Z is selected from optionally substituted $C_1$-$C_6$ alkylene, optionally substituted $C_2$-$C_6$ alkenylene, —O—, —S—, —$NR^2$—, —C(=O)—, —C(=O)—$NR^1$, —$NR^1$—C(=O)—, —C(=$NR^1$)—, optionally substituted —$C_3$-$C_6$ cycloalkyl, optionally substituted heterocyclyl, optionally substituted aryl, —[O—($C_1$-$C_6$ alkylene)]$_n$-, —[$NR^2$—($C_1$-$C_6$ alkylene)]$_n$-, —[S—($C_1$-$C_6$ alkylene)]$_n$-, and combinations thereof, wherein $R^1$ is H or optionally substituted $C_1$-$C_6$ alkyl, $R^2$ is optionally substituted $C_1$-$C_6$ alkyl, and n is an integer from 1-6, 6. The photoinitiator according to any of embodiments 1-2, wherein Z is selected from $C_1$-$C_6$ alkylene, $C_2$-$C_6$ alkenylene, —$NR^2$—, —C(=O)—($C_1$-$C_6$ alkylene)-, —C(=O)—O—($C_1$-$C_6$ alkylene)-, —C(=O)—NR—($C_1$-$C_6$ alkylene), —$C_3$-$C_6$ cycloalkyl, aryl, heterocyclyl, —[O—($C_1$-$C_6$ alkylene)]$_n$-, —[($C_1$-$C_6$ alkylene)-O—($C_1$-$C_6$ alkylene)]$_n$-, —[$NR^2$—($C_1$-$C_6$ alkylene)]$_n$, and —[S—($C_1$-$C_6$ alkylene)]$_n$-, wherein $R^1$ is H or optionally substituted $C_1$-$C_6$ alkyl, $R^2$ is optionally substituted $C_1$-$C_6$ alkyl, n is an integer from 1-2, and wherein any $C_1$-$C_6$ alkylene, $C_2$-$C_6$ alkenylene, —$C_3$-$C_6$ cycloalkyl, aryl or heterocyclyl moiety each independently is optionally substituted with one or more substituents.

7. A photoinitiator of Formula (I):

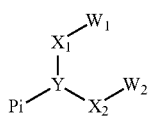
(I)

wherein:
Pi is a photoinitiator moiety;
Y is:

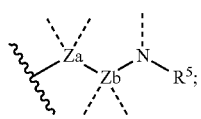
(III)

Za and Zb together form a linker in which Za is selected from optionally substituted —[O—($C_1$-$C_{12}$ alkylene)]$_n$-, optionally substituted —[NR$^2$—($C_1$-$C_{12}$ alkylene)]$_n$-, and optionally substituted —[S—($C_1$-$C_{12}$ alkylene)]$_n$-, wherein Za is joined to Pi via the O, N or S atom in Za, and Zb is a linker moiety;

—$X_1$—$W_1$ and —$X_2$—$W_2$ are each independently attached to Y at either the N-atom or the Za-linker or Zb-linker, one or both of the —$X_1$—$W_1$ and —$X_2$—$W_2$ may be attached to the same linker moiety wherever it is chemically feasible;

with the proviso that at least one of —$X_1$—$W_1$ and —$X_2$—$W_2$ is attached to an atom other than the N-atom;

when one of —$X_1$—$W_1$ or —$X_2$—$W_2$ is attached to the N-atom, said N-atom is also substituted with R$^5$; when neither of —$X_1$—$W_1$ or —$X_2$—$W_2$ are attached to the N-atom, it is substituted with R$^5$ and R$^6$;

R$^1$ is H or optionally substituted $C_1$-$C_{12}$ alkyl;
R$^2$ is optionally substituted $C_1$-$C_{12}$ alkyl;
n is an integer from 1-20;

$X_1$ and $X_2$ are each independently selected from optionally substituted $C_1$-$C_{12}$ alkylene, optionally substituted $C_2$-$C_{12}$ alkenylene, —O—, —S—, —NR$^4$—, —C(=O)—, —C(=NR$^3$)—, —Si(R$^3$)$_2$—O—, optionally substituted $C_3$-$C_8$ cycloalkyl, optionally substituted heterocyclyl, optionally substituted aryl, and combinations thereof;

Za, Zb, $X_1$ and $X_2$ are selected such that N is a tertiary amine;

$X_1$ and $X_2$, or a part thereof, may be linked to one another or to linkers Za or Zb, to form one or more ring structures;

R$^3$ is H or optionally substituted $C_1$-$C_{12}$ alkyl;
R$^4$ is optionally substituted $C_1$-$C_{12}$ alkyl;
R$^5$ and R$^6$ are each independently selected from optionally substituted $C_1$-$C_6$ alkyl, wherein the carbon atom adjacent to the N-atom is in a —CH$_2$— moiety;
$W_1$ and $W_2$ are each independently selected from —OH, —CH$_2$OH, —NH$_2$, —NHR$^8$, —SH, —Si(OR$^8$)$_2$—H, —C(=O)—OSi(R$^8$)$_3$, —NCO, —NCS, —COOH, —COOR$^8$, —COO-aryl, —C(=O)—Cl, —O—C(=O)—Cl, —C(O)—NH$_2$, —C(O)—NHR$^7$, —NH—C(O)—OR$^7$, and —OC(O)—NHR$^7$;

R$^7$ is H or $C_1$-$C_6$ alkyl; and
R$^8$ is $C_1$-$C_6$ alkyl.

8. The photoinitiator according to any of embodiments 1 or 7, wherein Zb is selected from a single bond, optionally substituted $C_1$-$C_{12}$ alkylene, optionally substituted $C_2$-$C_{12}$ alkenylene, —O—, —S—, —NR$^2$—, —C(=O)—, —C(=O)—NR$^1$, —NR$^1$—C(=O)—, —C(=NR$^1$)—, —SO$_2$—, —P(=O)(OR$^1$)—, optionally substituted $C_3$-$C_8$ cycloalkyl, optionally substituted heterocyclyl, optionally substituted aryl, optionally substituted —[O—($C_1$-$C_{12}$ alkylene)]$_n$-, optionally substituted —[NR$^2$—($C_1$-$C_{12}$ alkylene)]$_n$-, optionally substituted —[S—($C_1$-$C_{12}$ alkylene)]$_n$-, and combinations thereof, wherein R$^1$ is H or optionally substituted $C_1$-$C_{12}$ alkyl, R$^2$ is optionally substituted $C_1$-$C_{12}$ alkyl, and n is an integer from 1-20.

9. The photoinitiator according to any of embodiments 1 or 7, wherein Zb is selected from a single bond, optionally substituted $C_1$-$C_{12}$ alkylene, optionally substituted $C_2$-$C_{12}$ alkenylene, —O—, —S—, —NR$^2$—, —[O—($C_1$-$C_{12}$ alkylene)]$_n$-, and combinations thereof, wherein R$^2$ is optionally substituted $C_1$-$C_{12}$ alkyl and n is an integer from 1-20.

10. The photoinitiator according to any of embodiments 1 or 7, wherein Zb is selected from a single bond, —C(=O)—$C_1$-$C_6$ alkylene-, —SO$_2$—$C_1$-$C_6$ alkylene-, —P(=O)(OR$^1$)—($C_1$-$C_6$ alkylene)-, —$C_3$-$C_6$ cycloalkyl, heterocyclyl, aryl and -aryl-($C_1$-$C_6$ alkyl)-, wherein any $C_1$-$C_6$ alkylene, —$C_3$-$C_6$ cycloalkyl, heterocyclyl or aryl moiety each independently is optionally substituted with one or more substituents, wherein R$^1$ is H or $C_1$-$C_6$ alkyl, and n is an integer from 1-6.

11. The photoinitiator according to any of embodiments 1 or 7, wherein Zb is a single bond.

12. The photoinitiator according to any of embodiments 1, 7-11, wherein Za is selected from —[O—($C_1$-$C_6$ alkylene)]n-, —[NR$^2$—($C_1$-$C_6$ alkylene)]n, —[S—($C_1$-$C_6$ alkylene)]n-, —O—($C_1$-$C_6$ alkylene)-NR$^2$—($C_1$-$C_6$ alkylene)-, —NR$^2$—($C_1$-$C_6$ alkylene)-O—($C_1$-$C_6$ alkylene)-, —S—($C_1$-$C_6$ alkylene)-O—($C_1$-$C_6$ alkylene)-, —O—($C_1$-$C_6$ alkylene)-S—($C_1$-$C_6$ alkylene)-, —S—($C_1$-$C_6$ alkylene)-NR$^2$—($C_1$-$C_6$ alkylene)-, and —NR$^2$—($C_1$-$C_6$ alkylene)-S—($C_1$-$C_6$ alkylene)-, wherein $C_1$-$C_6$ alkylene optionally is substituted with one or more substituents, wherein R$^2$ is $C_1$-$C_6$ alkyl, and n is an integer from 1-2.

13. The photoinitiator according to any of embodiments 1, 7-12, wherein Za is selected from optionally substituted —O—($C_1$-$C_{12}$ alkylene)-, preferably optionally substituted —O—($C_1$-$C_6$ alkylene)-.

14. A photoinitiator of Formula (I):

(I)

wherein:
Pi is a photoinitiator moiety;
Y is selected from:

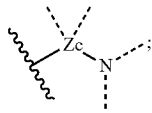

(IV)

Zc is a linker moiety selected from —C(O)—($C_1$-$C_{12}$ alkylene)-, —C(O)—$CH_2$—($C_2$-$C_{12}$ alkenylene)-, —C(O)—O—($C_1$-$C_{12}$ alkylene)-, —C(O)—O—($C_2$-$C_{12}$ alkenylene)-, —C(O)—$NR^1$—($C_1$-$C_{12}$ alkylene)-, —C(O)—NR—($C_2$-$C_{12}$ alkenylene)-, —($C_1$-$C_{12}$ alkylene)-C(O)—($C_1$-$C_{12}$ alkylene)-, —($C_1$-$C_{12}$ alkylene)-C(O)—O—($C_1$-$C_{12}$ alkylene)-, —($C_1$-$C_{12}$ alkylene)-O—C(O)—($C_1$-$C_{12}$ alkylene)-, —($C_1$-$C_{12}$ alkylene)-C(O)—NR—($C_1$-$C_{12}$ alkylene)-, —($C_1$-$C_{12}$ alkylene)-NR—C(O)—($C_1$-$C_{12}$ alkylene)-, —($C_1$-$C_{12}$ alkylene)-NH—C(O)—NH—($C_1$-$C_{12}$ alkylene)-, —NH—C(O)—NH—($C_1$-$C_{12}$ alkylene)-, and —[$NR^2$—($C_1$-$C_{12}$ alkylene)]$_n$-, wherein any alkylene or alkenylene moiety each independently is optionally substituted with one or more substituents;
—$X_1$—$W_1$ and —$X_2$—$W_2$ are each independently attached to Y at either the N-atom or the -Zc- linker, one or both of the —$X_1$—$W_1$ and —$X_2$—$W_2$ may be attached to Zc wherever it is chemically feasible;
when one of —$X_1$—$W_1$ or —$X_2$—$W_2$ is attached to the N-atom, said N-atom is also substituted with $R^5$; when neither of —$X_1$—$W_1$ or —$X_2$—$W_2$ are attached to the N-atom, it is substituted with $R^5$ and $R^6$;
$R^1$ is H or optionally substituted $C_1$-$C_{12}$ alkyl;
$R^2$ is optionally substituted $C_1$-$C_{12}$ alkyl;
$X_1$ and $X_2$ are each independently selected from optionally substituted $C_1$-$C_{12}$ alkylene, optionally substituted $C_2$-$C_{12}$ alkenylene, —O—, —S—, —$NR^4$—, —C(=O)—, —C(=$NR^3$)—, —Si($R^3$)$_2$—O—, optionally substituted $C_3$-$C_8$ cycloalkyl, optionally substituted heterocyclyl, optionally substituted aryl, and combinations thereof;
Zc, $X_1$ and $X_2$ are selected such that N is a tertiary amine;
$X_1$ and $X_2$, or a part thereof, may be linked to one another or to linker Zc to form one or more ring structures;
$R^3$ is H or optionally substituted $C_1$-$C_{12}$ alkyl;
$R^4$ is optionally substituted $C_1$-$C_{12}$ alkyl;
$R^5$ and $R^6$ are each independently selected from optionally substituted $C_1$-$C_6$ alkyl, wherein the carbon atom adjacent to the N-atom is in a —$CH_2$— moiety;
$W_1$ and $W_2$ are each independently selected from —OH, —$CH_2OH$, —$NH_2$, —$NHR^8$, —SH, —Si($OR^8$)$_2$—H, —C(=O)—OSi($R^8$)$_3$, —NCO, —NCS, —COOH, —$COOR^8$, —COO-aryl, —C(=O)—Cl, —O—C(=O)—Cl, —C(O)—$NH_2$, —C(O)—$NHR^7$, —NH—C(O)—$OR^7$, and —OC(O)—$NHR^7$;
$R^7$ is H or $C_1$-$C_6$ alkyl; and
$R^8$ is $C_1$-$C_6$ alkyl.

15. The photoinitiator according to any of embodiments 1 or 14, wherein Zc is selected from —C(O)—($C_1$-$C_{12}$ alkylene)-, —C(O)—$CH_2$—($C_2$-$C_{12}$ alkenylene)-, —($C_1$-$C_{12}$ alkylene)-C(O)—($C_1$-$C_{12}$ alkylene)-, wherein alkylene or alkenylene moiety each independently is optionally substituted with one or more substituents.

16. The photoinitiator according to any of the preceding embodiments, wherein $W_1$ and $W_2$ each independently are selected from —OH, —$CH_2OH$, —$NH_2$, —$NHR^7$, —SH, —NCO, —NCS, and —COOH.

17. The photoinitiator according to any of the preceding embodiments, wherein $W_1$ and $W_2$ each independently are selected from —OH, —$NH_2$, —$NHR^7$, and —SH.

18. The photoinitiator according to any of the preceding embodiments, wherein $W_1$ and $W_2$ are the same.

19. The photoinitiator according to any of the preceding embodiments, wherein $X_1$ and $X_2$ are independently selected from optionally substituted $C_1$-$C_{12}$ alkylene, preferably optionally substituted $C_1$-$C_6$ alkylene.

20. The photoinitiator according to any of the preceding embodiments, wherein the carbon atom of $X_1$ and/or $X_2$ adjacent to the tertiary amine atom carry no more than one substituent other than Hydrogen.

21. The photoinitiator according to any of the preceding embodiments, wherein $X_1$ and $X_2$ are the same.

22. The photoinitiator according to any one of embodiments 1-20, wherein $X_1$ and $X_2$ are independently selected from optionally substituted $C_1$-$C_{12}$ alkylene, and $W_1$ and $W_2$ are —$CH_2OH$.

23. The photoinitiator according to any of the preceding embodiments, wherein one or more substituents are selected from —F, —Cl, —Br, —I, —CN, —$NO_2$, —$C_1$-$C_6$ alkyl, —$C_2$-$C_6$ alkenyl, —$C_3$-$C_6$ cycloalkyl, aryl, heterocyclyl, —O—($C_1$-$C_6$ alkyl), —O—$C_3$-$C_8$ cycloalkyl, —O-aryl, —C(O)—($R^9$), —C(O)-aryl, —C(O)O—($C_1$-$C_6$ alkyl), —C(O)O-aryl, —O—C(O)-aryl, —O—C(O)—O—($C_1$-$C_6$ alkyl), —O—C(O)—O-aryl, —N($C_1$-$C_6$alkyl)$_2$, —N($C_1$-$C_6$alkyl)($C_3$-$C_6$ cycloalkyl), —N($C_1$-$C_6$alkyl)(aryl), —N(aryl)$_2$, —N($R^9$)—C(O)—($C_1$-$C_6$ alkyl), —N($R^9$)—C(O)-aryl, —C(O)—N($R^9$)$_2$, —C(O)—N($R^9$)-aryl, —C(O)—N(aryl)$_2$, —O—C(O)—N($R^9$)$_2$, —O—C(O)—NH—($C_1$-$C_6$aryl), —N($R^9$)—C(O)—O—($C_1$-$C_6$alkyl), —NH—C(O)—O—($C_1$-$C_6$aryl), —S(O)—($C_1$-$C_6$ alkyl), —S(O)-aryl, —$SO_2$—($C_1$-$C_6$ alkyl), —$SO_2$-aryl, —S—($C_1$-$C_6$ alkyl), and —S-aryl; wherein $R^9$ is H or $C_1$-$C_6$ alkyl.

24. The photoinitiator according to any of the preceding embodiments, wherein one or more substituents are selected from —F, —Cl, —Br, —I, —CN, —$NO_2$, —$C_1$-$C_6$ alkyl, aryl, —O—($C_1$-$C_6$ alkyl), —C(O)—O—($C_1$-$C_6$ alkyl), —S—($C_1$-$C_6$ alkyl), —S(O)—($C_1$-$C_6$ alkyl), —$SO_2$—($C_1$-$C_6$ alkyl), —NH—C(O)—($C_1$-$C_6$ alkyl), —C(O)—NH—($C_1$-$C_6$ alkyl), and —C(O)—$NH_2$.

25. The photoinitiator according to any of the preceding embodiments, wherein Pi is a photoinitiator moiety selected from the group consisting of benzoin ethers, phenyl hydroxyalkyl ketones, phenyl aminoalkyl ketones, benzophenones, thioxanthones, xanthones, acridones, anthraquinones, fluorenones, dibenzosuberones, benzils, benzil ketals, α-dialkoxy-acetophenones, α-hydroxy-alkyl-phenones, α-amino-alkyl-phenones, acyl-phosphine oxides, phenyl ketocoumarins, camphorquinones, silane and derivatives thereof, and maleimides.

26. The photoinitiator according to any of the preceding embodiments, wherein Pi is a photoinitiator moiety selected from benzophenones, thioxanthones, benzilketals and phenyl hydroxyalkyl ketones, such as 2-hydroxy-2-methyl-1-phenylpropan-1-ones.

27. The photoinitiator according to any one of embodiments 1-24, wherein Pi is a non-cleavable photoinitiator.

28. The photoinitiator according to any one of embodiments 1-24, having the general formula (Va):

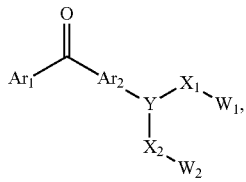

(Va)

wherein $Ar_1$ and $Ar_2$ are independently selected from the same or different aryl, where Y may be present at any position on $Ar_2$, and where each aryl independently may be optionally substituted with one or more substituents selected from the substituents defined in embodiment 23 or 24.

29. The photoinitiator according to embodiment 28, wherein $Ar_1$ and $Ar_2$ each independently are optionally substituted phenyl; where Y may be attached at any position on $Ar_2$.

30. The photoinitiator according to any one of embodiments 28-29, wherein $Ar_1$ and $Ar_2$ are both phenyl.

31. The photoinitiator according to any one of embodiments 28-30, wherein Y is present at the para-position on $Ar_2$.

32. The photoinitiator according to any of the preceding embodiments, having the general formula (Vb):

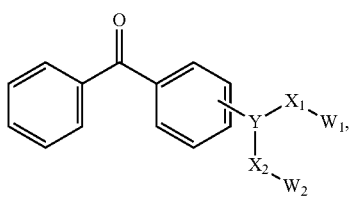

(Vb)

wherein Y, $X_1$, $X_2$, $W_1$ and $W_2$, are as defined in any one of embodiments 1-31.

33. The photoinitiator according to any one of embodiments 1-30, having the general formula (Vc):

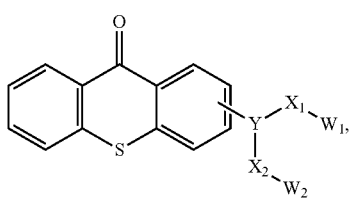

(Vc)

wherein Y, $X_1$, $X_2$, $W_1$ and $W_2$, are as defined in any one of embodiments 1-31.

34. The photoinitiator according to any of the embodiments 1-32, having the general formula (Vd):

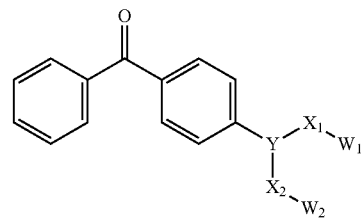

(Vd)

wherein Y, $X_1$, $X_2$, $W_1$ and $W_2$ are as defined in any one of embodiments 1-31.

35. The photoinitiator according to any one of embodiments 2-31, having the general formula:

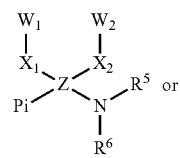

(IIa)

or

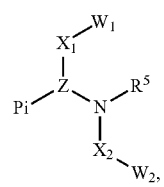

(IIb)

wherein Pi, Z, $X_1$, $X_2$, $W_1$, $W_2$, $R^5$, and $R^6$ are as defined in any one of embodiments 2-31.

36. The photoinitiator according to any one of embodiments 7-31, having the general formula:

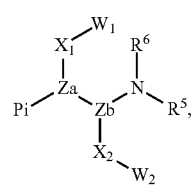

(IIIa)

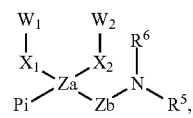

(IIIb)

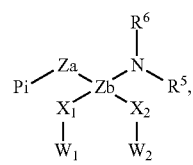

(IIIc)

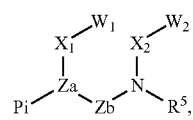

(IIId)

wherein Pi, Za, Zb, $X_1$, $X_2$, $W_1$, $W_2$, $R^5$, and $R^6$ are as defined in any one of embodiments 7-31.

37. The photoinitiator according to any one of embodiments 14-31, having the general formula:

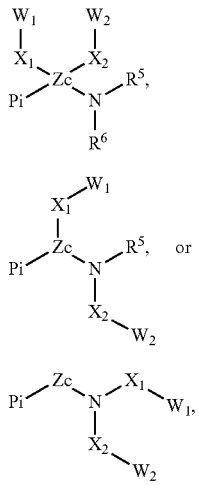

wherein Pi, Zc, $X_1$, $X_2$, $W_1$, $W_2$, $R^5$, and $R^6$ are as defined in any one of embodiments 14-31.

38. The photoinitiator according to embodiment 1, being
2-(4-benzoylphenoxymethyl)-2-[(dimethylamino)methyl] propane-1,3-diol;
2-(4-benzoylphenoxymethyl)-2-(piperidin-1-ylmethyl)propane-1,3-diol;
1-chloro-4-{2-[(dimethylamino)methyl]-3-hydroxy-2-(hydroxymethyl)propoxy}-9H-thioxanthen-9-one;
2-[(4-benzoylphenyl)methyl]-2-[(dimethylamino)methyl] propane-1,3-diol;
2-[3-(4-benzoylphenoxyl)propyl]-2-[(dimethylamino)methyl]propane-1,3-diol;
2-{[5-hydroxy-4-(hydroxymethyl)-4-(piperidin-1-ylmethyl) pentyl]oxy}-9H-thioxanthen-9-one;
3-(4-benzoylphenoxy)-2-{[(2-hydroxyethyl)(methyl)amino] methyl}propan-1-ol;
{4-[2-(dimethylamino)-3-hydroxy-2-(hydroxymethyl) propyl]phenyl}(phenyl)methanone;
2-[3-(4-benzoylphenoxyl)propyl]-2-(dimethylamino)propane-1,3-diol;
2-[(dimethylamino)methyl]-3-hydroxy-2-(hydroxymethyl) propyl 4-benzoylbenzoate;
2-[(dimethylamino)methyl]-3-hydroxy-2-(hydroxymethyl) propyl 2-benzoylbenzoate;
3-hydroxy-2-(hydroxymethyl)-2-(morpholin-4-ylmethyl) propyl 4-benzoylbenzoate;
3-hydroxy-2-(hydroxymethyl)-2-(morpholin-4-ylmethyl) propyl 2-benzoylbenzoate;
2-[(dimethylamino)methyl]-3-hydroxy-2-(hydroxymethyl) propyl 2-[(1-chloro-9-oxo-9H-thioxanthen-4-yl)oxy]acetate;
3-hydroxy-2-(hydroxymethyl)-2-(morpholin-4-ylmethyl) propyl 2-[(1-chloro-9-oxo-9H-thioxanthen-4-yl)oxy]acetate;
(4-{[3-(dimethylamino)-1,4-dihydroxybutan-2-yl] oxy}phenyl)(phenyl)methanone;
1-(4-benzoylphenyl)-2-[bis(2-hydroxyethyl)amino]ethanone; or
1-(4-benzoylphenyl)-3-[bis(2-hydroxyethyl)amino]propan-1-one.

39. The photoinitiator according to embodiment 1, being:
2-(4-benzoylphenoxymethyl)-2-[(dimethylamino)methyl] propane-1,3-diol;
2-(4-benzoylphenoxymethyl)-2-(piperidin-1-ylmethyl)propane-1,3-diol;
1-chloro-4-{2-[(dimethylamino)methyl]-3-hydroxy-2-(hydroxymethyl)propoxy}-9H-thioxanthen-9-one;
2-[3-(4-benzoylphenoxyl)propyl]-2-[(dimethylamino)methyl]propane-1,3-diol;
2-{[5-hydroxy-4-(hydroxymethyl)-4-(piperidin-1-ylmethyl) pentyl]oxy}-9H-thioxanthen-9-one;
2-[3-(4-benzoylphenoxyl)propyl]-2-(dimethylamino)propane-1,3-diol;
2-[(dimethylamino)methyl]-3-hydroxy-2-(hydroxymethyl) propyl 2-benzoylbenzoate;
2-[(dimethylamino)methyl]-3-hydroxy-2-(hydroxymethyl) propyl 2-[(1-chloro-9-oxo-9H-thioxanthen-4-yl)oxy]acetate; or
1-(4-benzoylphenyl)-2-[bis(2-hydroxyethyl)amino]ethanone.

40. A polymeric photoinitiator, being a co-polymer of at least one monomer (A) with at least one monomer (B), wherein:
monomer (A) is a photoinitiator monomer (A) of the formula (I):

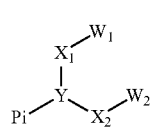

as defined in any of embodiments 1-39;
monomer (B) comprises at least two functional groups $W_3$ and $W_4$, said $W_3$ and $W_4$ being independently selected from —OH, —CH$_2$OH, —NH$_2$, —NHR$^{11}$, —SH, —Si(OR$^{11}$)$_2$—H, —C(=O)—OSi(R$^{11}$)$_3$, —NCO, —NCS, —COOH, —COOR$^{11}$, —COO-aryl, —C(=O)—Cl, —O—C(=O)—Cl, —C(O)—NH$_2$, —C(O)—NHR$^{10}$, —NH—C(O)—OR$^{10}$, and —OC(O)—NHR$^{11}$, wherein R$^{10}$ is H or C$_1$-C$_6$ alkyl, and wherein R$^{11}$ is C$_1$-C$_6$ alkyl;
wherein $W_1$, $W_2$, $W_3$ and $W_4$ are selected such that—in the co-polymerization of monomers (A) and (B)—$W_1$ reacts with $W_3$ to form a urethane, thiourethane, urea, thiourea, ester, ether, amide, carbonate, allophanate or biuret moiety, and $W_2$ reacts with $W_4$ to form a urethane, thiourethane, urea, thiourea, ester, ether, amide, carbonate, allophanate or biuret moiety.

41. The polymeric photoinitiator according to embodiment 40, wherein monomer (B) has the structure of formula (VI):

$$W_3\text{-}Q\text{-}W_4 \qquad (VI)$$

wherein $W_3$ and $W_4$ are defined as in embodiment 40, and wherein Q is selected from the group consisting of optionally substituted C$_1$-C$_{12}$ alkylene, optionally substituted C$_2$-C$_{12}$ alkenylene, optionally substituted C$_3$-C$_8$ cycloalkyl, optionally substituted C$_3$-C$_{12}$ heterocyclyl, optionally substituted aryl, optionally substituted biaryl, —[O—(C$_1$-C$_{12}$ alkylene)]$_m$-, —[S—(C$_1$-C$_{12}$ alkylene)]$_m$-, where m is an integer from 1-1000, and combinations thereof.

42. The polymeric photoinitiator according to any one of embodiments 40-41, wherein Q is selected from the group consisting of optionally substituted C$_1$-C$_{12}$ alkylene, optionally substituted C$_2$-C$_{12}$ alkenylene, optionally substituted $C_3$-$C_8$ cycloalkyl, optionally substituted $C_3$-$C_{12}$ heterocyclyl, optionally substituted aryl and optionally substituted biaryl.

43. The polymeric photoinitiator according to any of embodiments 40-42, wherein Q is selected from the group consisting of optionally substituted aryl and optionally substituted biaryl.

44. The polymeric photoinitiator according to any one of embodiments 40-43, wherein $W_3$ and $W_4$ are independently selected from isocyanate and thioisocyanate groups.

45. The polymeric photoinitiator according to any one of embodiments 40-44, wherein $W_3$ and $W_4$ are the same functional groups.

46. The polymeric photoinitiator according to any of embodiments 40-41, wherein monomer (B) is selected from the group consisting of: 1,4-phenylene diisocyanate (PPDI), toluene diisocyanate (TDI) as both its 2,4 and 2,6 isomers, methylene diphenyl diisocyanate (MDI) as both its 4,4' and 2,4' isomers, 1,5-naphthalene diisocyanate (NDI), 3,3'-bitolylene-4,4'-diisocyanate (TODI), 1,3-xylylenediisocyanate (XDI), tetramethyl-m-xylidene diisocyanate (TMXDI), 1,6-hexamethylene diisocyanate (HDI), isophorone diisocyanate (IPDI), bis(4-isocyanatocyclohexyl)methane (HMDI), 2,2,5-trimethylhexane diisocyanate (TMHDI), 1,4-cyclohexane diisocyanate (CHDI), and 1,3-bis(isocyanato-methyl)cyclohexane (HXDI).

47. The polymeric photoinitiator according to any one of embodiments 40-46, wherein—in the co-polymerization of monomers (A) and (B)—$W_1$ reacts with $W_3$ to form a urethane, thiourethane, urea, thiourea, ester or amide moiety, and $W_2$ reacts with $W_4$ to form a urethane, thiourethane, urea, thiourea, ester or amide moiety.

48. The polymeric photoinitiator according to any one of embodiments 40-47, wherein—in the co-polymerization of monomers (A) and (B)—$W_1$ reacts with $W_3$ to form a urethane, or thiourethane moiety, and $W_2$ reacts with $W_4$ to form a urethane or thiourethane moiety.

49. The polymeric photoinitiator according to any one of embodiments 40-48, wherein both $W_1$ and $W_2$ are alcohol functional groups and both $W_3$ and $W_4$ are isocyanate functional groups.

50. The polymeric photoinitiator according to any one of embodiments 40-49, further comprising one or more additional monomers (C),
wherein each of said one or more additional monomers (C) comprises at least two functional groups $W_5$ and $W_6$, said $W_5$ and $W_6$ being independently selected from —OH, —$CH_2OH$, —$NH_2$, —$NHR^{13}$, —SH, —$Si(OR^{13})_2$—H, —C(=O)—$OSi(R^{13})_3$, —NCO, —NCS, —COOH, —$COOR^{13}$, —COO-aryl, —C(=O)—Cl, —O—C(=O)—Cl, —C(O)—$NH_2$, —C(O)—$NHR^{12}$, —NH—C(O)—$OR^{12}$, and —OC(O)—$NHR^2$, wherein $R^{12}$ is H or $C_1$-$C_6$ alkyl, $R^{13}$ is $C_1$-$C_6$ alkyl; and
wherein $W_5$ and $W_6$ are selected such that—in the co-polymerization of monomers (A), (B) and (C)—$W_5$ reacts with $W_1$ or $W_3$ to form a urethane, thiourethane, urea, thiourea, ester, ether, amide, carbonate, allophanate or biuret moiety, and $W_6$ reacts with $W_2$ or $W_4$ to form a urethane, thiourethane, urea, thiourea, ester, ether, amide, carbonate, allophanate or biuret moiety.

51. The polymeric photoinitiator according to embodiment 50, wherein monomer (C) has the structure of formula (VII):

$$W_5\text{-T-}W_6 \quad\quad\quad (VII)$$

wherein $W_5$ and $W_6$ are defined as in embodiment 50 and wherein T is selected from the group consisting of optionally substituted $C_1$-$C_{12}$ alkylene, optionally substituted $C_1$-$C_{12}$ alkenylene, optionally substituted $C_3$-$C_8$ cycloalkyl, optionally substituted $C_3$-$C_{12}$ heterocyclyl, optionally substituted aryl, optionally substituted biaryl, —[O—($C_1$-$C_{12}$ alkylene)]$_m$-, —[S—($C_1$-$C_{12}$ alkylene)]$_m$-, where m is an integer from 1-1000, and combinations thereof.

52. The polymeric photoinitiator according to embodiment 51, wherein T is selected from the group consisting of —[O—($C_1$-$C_{12}$ alkylene)]$_m$-, —[S—($C_1$-$C_{12}$ alkylene)]$_m$-, where m is an integer from 1-1000.

53. The polymeric photoinitiator according to any one of embodiments 50-52, wherein $W_5$ and $W_6$ are independently selected from —OH, —$CH_2OH$, —$NH_2$, —$NHR^{13}$, and —SH, preferably —OH or —$CH_2OH$.

54. The polymeric photoinitiator according to any one of embodiments 50-53, wherein $W_5$ and $W_6$ are the same functional groups.

55. The polymeric photoinitiator according to embodiment 50, wherein monomer (C) is selected from the group consisting of: polyethylene glycol (PEG), polypropylene glycol (PPG), random and block poly(ethylene glycol)-poly(propylene glycol) copolymers, poly(tetramethylene glycol) (PTMG), poly(1,4-butanediol adipate), poly(ethanediol 1,4-butanediol adipate), poly(caprolacton)diol, poly(1,6-hexanediol carbonate) and poly(ethylene terephthalate)diol.

56. The polymeric photoinitiator according to any one of the preceding embodiments, wherein the weight ratio of monomers (A):(B) is 1:99-99:1, preferably 1:99-50:50.

57. The polymeric photoinitiator according to any one of embodiments 50-56, wherein the weight ratio of monomers (A):(C) is 1:99-99:1, preferably 1:99-50:50.

58. A polyacrylate obtained by radical polymerization of at least one acrylate monomer (Ac) in the presence of a polymeric photoinitiator, said polymeric photoinitiator being a co-polymer of at least one monomer (A) with at least one monomer (B), wherein:
monomer (A) is a photoinitiator monomer (A) of the formula (I):

$$Pi\diagup Y\diagdown{\overset{\displaystyle X_1{-}W_1}{\underset{\displaystyle X_2{-}W_2}{|}}} \quad\quad (I)$$

as defined in any one of embodiments 1-39; and
monomer (B) is as defined in any one of embodiments 40-46;
wherein—in the co-polymerization of monomers (A) and (B) in the polymeric photoinitiator—$W_1$ reacts with $W_3$ to form a urethane, thiourethane, urea, thiourea, ester or amide moiety, and $W_2$ reacts with $W_4$ to form a urethane, thiourethane, urea, thiourea, ester or amide moiety.

59. The polyacrylate according to embodiment 58, wherein—in the co-polymerization of monomers (A) and (B) in the polymeric photoinitiator—$W_1$ reacts with $W_3$ to form a urethane, or thiourethane moiety, and $W_2$ reacts with $W_4$ to form a urethane or thiourethane moiety.

60. The polyacrylate according to any one of embodiments 58-59, wherein the polymeric photoinitiator further comprises one or more additional monomers (C) as defined in any one of embodiments 30-55.
61. The polyacrylate according to any one of embodiments 58-60, wherein the weight ratio of monomers (A):(B) is as defined in any one of embodiments 56-57.
62. The polyacrylate according to any one of embodiments 58-61, wherein the acrylate monomer (Ac) is a mono-, di- or tri-acrylate, preferably a mono-acrylate.
63. The polyacrylate according to any one of embodiments 58-62, wherein the acrylate monomer (Ac) comprises a polyurethane oligomer having terminal acrylate groups.
64. The polyacrylate according to any of embodiments 58-63, wherein the acrylate monomer (Ac) is an acrylate ester of the formula (VIII):

$(R^{14})(R^{15})C=C(R^{16})-C(=O)-O-R^{17}$ (VIII)

wherein $R^{14}$-$R^{16}$ are independently selected from the group consisting of H, optionally substituted $C_1$-$C_{12}$ alkyl, optionally substituted $C_1$-$C_{12}$ alkenyl, optionally substituted $C_3$-$C_{12}$ heterocyclyl, and optionally substituted aryl, and $R^{17}$ is selected from the group consisting of optionally substituted $C_1$-$C_{12}$ alkyl, optionally substituted $C_1$-$C_{12}$ alkenyl, optionally substituted $C_3$-$C_{12}$ heterocyclyl, and optionally substituted aryl.

65. A method for producing a polymeric photoinitiator, said method comprising step-growth co-polymerization of at least one monomer (A) with at least one monomer (B), wherein (A) and (B) have the structures described in embodiments 40-46.
66. The method according to embodiment 43, wherein the co-polymerization reaction additionally comprises one or more additional monomers (C), having the structure described in embodiments 50-55.
67. A method of cross-linking the polymeric photoinitiator as defined in any one of embodiments 40-57, said method comprising exposing the polymeric photoinitiator to UV radiation and/or heat.
68. Use of a polymeric photoinitiator according to any one of embodiments 40-57 as a photoinitiator of radical polymerization.
69. A method for producing a polyacrylate, said method comprising the steps of:
   a. combining one or more acrylate monomers with a polymeric photoinitiator, said polymeric photoinitiator being as defined in any one of embodiments 40-57,
   b. subjecting the mixture from step a. to UV radiation and/or heat.
70. Use of a polymeric photoinitiator according to any one of embodiments 40-57, as a photoinitiator of radical polymerization of acrylate monomers.
71. Use of a photoinitiator according to any of embodiments 1-39 in preparation of a polymeric photoinitiator.

EXPERIMENTAL SECTION

Example 1

2-(4-benzoylphenoxymethyl)-2-[(dimethylamino)methyl]propane-1,3-diol

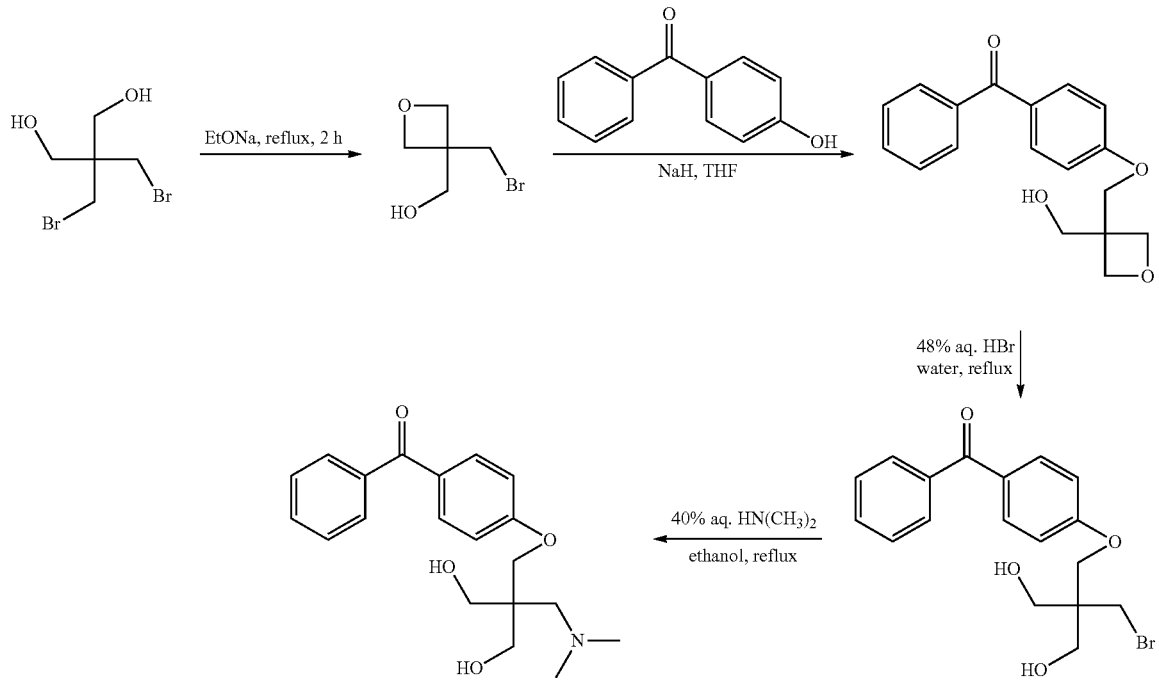

Dissolve 4-hydroxybenzophenone in anhydrous THF and treat it with equimolar quantity of sodium hydride at 0° C. for 2 h. Stir and warm the suspension to 50° C. and treat it with an equimolar quantity of 3-Bromomethyl-3-hydroxymethyloxetane (readily prepared in one step by method described in U.S. Pat. No. 5,489,700 or Tet. Lett. 2011, 52, p. 565-567 from commercially available 2,2-bis-(bromomethyl)propane-1,3-diol). Stir overnight at 50° C., filter the reaction mixture, evaporate the filtrate to dryness and purify the residue by column chromatography to provide (4-{[3-(hydroxymethyl)oxetan-3-yl]methoxy}phenyl)(phenyl)methanone.

Suspend (4-{[3-(hydroxymethyl)oxetan-3-yl]methoxy}phenyl)(phenyl)methanone in a mixture of 48% aq. HBr and water and heat the mixture to reflux for 1 hour. Extract the product into dichloromethane, and evaporate the solvent, the solid residue may be recrystallised from ethanol to provide {4-[3-bromo-2,2-bis(hydroxymethyl)propoxy]phenyl}(phenyl)methanone.

Dissolve the {4-[3-bromo-2,2-bis(hydroxymethyl)propoxy]phenyl}(phenyl)methanone obtained in the previous stage in ethanol and treat it with excess of 40% aq. dimethylamine at reflux for 8 h. Remove the solvent in vacuo and purify the residue by column chromatography to provide the desired 2-(4-benzoylphenoxymethyl)-2-[(dimethylamino)methyl]propane-1,3-diol.

Example 2

General Procedure for the for Preparation of Polyurethanes in Solvent

A glass vial is charged with a reactive photoinitiator and polyethylene glycol. The reaction vessel is heated to 120-130° C. under vacuum for 1 h to remove all moisture. The reaction vessel is then allowed to cool under vacuum, fitted with a reflux condenser and flushed with nitrogen. Dry chlorobenzene is added and the reaction is stirred at 60° C. to obtain a homogeneous clear solution with 30 wt % of solids. Appropriate equimolar amount of diisocyanate is added via syringe and the reaction mixture is heated to 70° C. for 10 h. The viscous yellow mixture is evaporated in vacuo, residual chlorobenzene is removed by co-evaporation with MeOH-water. The resulting gummy solid is dried in vacuo for 4-6 h at 75° C. This provide the appropriate polyurethane polymer as a light yellow gummy solid.

Example 3

UV Curing of Polyurethanes

A polyurethane prepared in Example 2 is processed to a plate using a heat press. A disc is cut from this plate (Ø25 mm) and placed in a plate-plate rheometer, where the bottom plate consists of a quartz window. Rheological properties is measured at 1 Hz at 120° C., where a UV-light source irradiating the polyurethane sample through the quartz plate is turned on at t=0 s. After approximately 60 s the sample may a transition from a liquid state to a solid state, i.e. a gel-point, which demonstrates that the photoinitiator moieties within the polyurethane are actually responsible for curing the sample when exposed to UV light.

Example 4

UV Curing of Acrylics

Route to Polymerized N-Butyl Acrylate

A solution of 500 mg of a copolymer prepared in Example 2 in 10 mL THF is prepared. This solution is added to 10 mL of N-butylacrylate and mixed thoroughly. A film of this solution is spread out on a flat substrate and is subjected to UV irradiation and cured to provide a sticky solid.

Although the invention has been described with reference to a number of examples and reaction schemes, it should not be considered as limited by the above description. The full scope of the invention is defined by the appended claims.

The invention claimed is:

1. A polymeric photoinitiator, comprising a co-polymer of at least one monomer (A) with at least one monomer (B), wherein:

monomer (A) is a photoinitiator monomer comprising formula (I):

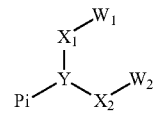

wherein:
Pi is a photoinitiator moiety;
Y is:

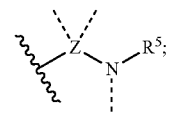

Z is a linker moiety selected from an optionally substituted —O—($C_1$-$C_{12}$ alkylene)-, an optionally substituted —S—($C_1$-$C_{12}$ alkylene)-, and an optionally substituted —$NR^2$—($C_1$-$C_{12}$ alkylene)-;
—$X_1$—$W_1$ and —$X_2$—$W_2$ are each independently attached to Y via the Z-linker;
—$X_1$—$W_1$ and —$X_2$—$W_2$ may be attached to the Z-linker wherever it is chemically feasible, corresponding to formula (IIa):

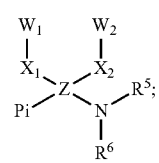

$R^2$ is an optionally substituted $C_1$-$C_{12}$ alkyl;
$X_1$ and $X_2$ are each independently selected from a single bond, an optionally substituted $C_1$-$C_{12}$ alkylene, an optionally substituted $C_2$-$C_{12}$ alkenylene, —O—, —S—, —$NR^4$—, —C(=O)—, —C(=$NR^3$)—, —Si($R^3$)$_2$—O—, an optionally substituted $C_3$-$C_8$ cycloalkyl, an optionally substituted heterocyclyl, an optionally substituted aryl, and combinations thereof;
Z is selected such that N is a tertiary amine;
$R^3$ is H or an optionally substituted $C_1$-$C_{12}$ alkyl;
$R^4$ is an optionally substituted $C_1$-$C_{12}$ alkyl;
$R^5$ and $R^6$ are each independently selected from an optionally substituted $C_1$-$C_6$ alkyl, wherein the carbon atom adjacent to the N-atom is in a —$CH_2$— moiety;
$W_1$ and $W_2$ are each independently selected from —OH, —$CH_2OH$, —$NH_2$, —$NHR^8$, —SH, —NCO, —NCS, and —COOH;
$R^8$ is a $C_1$-$C_6$ alkyl; and
any optional substituents are selected from —F, —Cl, —Br, —I, —CN, —$NO_2$, —$C_1$-$C_6$ alkyl, aryl, —O—($C_1$-$C_6$ alkyl), —C(O)—O—($C_1$-$C_6$ alkyl), —S—($C_1$-$C_6$ alkyl), —S(O)—($C_1$-$C_6$ alkyl), —$SO_2$—($C_1$-$C_6$ alkyl), —NH—C(O)—($C_1$-$C_6$ alkyl), —C(O)—NH—($C_1$-$C_6$ alkyl), and —C(O)—$NH_2$;

monomer (B) comprises formula (VI):

$$W_3\text{-}Q\text{-}W_4 \quad (VI)$$

Q is selected from the group consisting of an optionally substituted $C_1$-$C_{12}$ alkylene, an optionally substituted $C_2$-$C_{12}$ alkenylene, an optionally substituted $C_3$-$C_8$ cycloalkyl, an optionally substituted $C_3$-$C_{12}$ heterocyclyl, an optionally substituted aryl, an optionally substituted biaryl, a —[O—($C_1$-$C_{12}$ alkylene)]m-, a —[S—($C_1$-$C_{12}$ alkylene)]$_m$-, where m is an integer from 1-1000, and combinations thereof;

$W_3$ and $W_4$ each independently selected from —OH, —$CH_2OH$, —$NH_2$, —$NHR^{11}$, —SH, —Si$(OR^{11})_2$—H, —C(=O)—OSi$(R^{11})_3$, —NCO, —NCS, —COOH, —COOR$^{11}$, —COO-aryl, —C(=O)—Cl, —C(O)—$NH_2$, —C(O)—NHR$^{10}$, —NH—C(O)—OR$^{10}$, and —OC(O)—NHR$^{10}$; wherein R$^{10}$ is H or $C_1$-$C_6$ alkyl, and R$^{11}$ is $C_1$-$C_6$ alkyl;

wherein $W_1$, $W_2$, $W_3$ and $W_4$ are selected such $W_1$ reacts with $W_3$ to form a urethane, thiourethane, urea, thiourea, ester, ether, amide, carbonate, allophanate or biuret moiety, and $W_2$ reacts with $W_4$ to form a urethane, thiourethane, urea, thiourea, ester, ether, amide, carbonate, allophanate or biuret moiety.

2. The polymeric photoinitiator according to claim 1, wherein Z is selected from an optionally substituted —O—($C_1$-$C_6$ alkylene)-, an optionally substituted —S—($C_1$-$C_6$ alkylene)-, and an optionally substituted —NR$^2$—($C_1$-$C_6$ alkylene)-.

3. The polymeric photoinitiator according to claim 1, wherein R$^2$ is an optionally substituted $C_1$-$C_6$ alkyl.

4. The polymeric photoinitiator according to claim 1, wherein $W_1$ and $W_2$ each independently are selected from —$CH_2OH$, —OH, —$NH_2$, —NHR$^8$, and —SH.

5. The polymeric photoinitiator according to claim 1, wherein $W_1$ and $W_2$ are the same.

6. The polymeric photoinitiator according to claim 1, wherein $X_1$ and $X_2$ are independently selected from a single bond or an optionally substituted $C_1$-$C_{12}$ alkylene.

7. The polymeric photoinitiator according to claim 1, wherein $X_1$ and $X_2$ are the same.

8. The polymeric photoinitiator according to claim 1, wherein Pi is a photoinitiator moiety selected from the group consisting of benzoin ethers, phenyl hydroxyalkyl ketones, phenyl aminoalkyl ketones, benzophenones, thioxanthones, xanthones, acridones, anthraquinones, fluorenones, dibenzosuberones, benzils, benzil ketals, α-dialkoxy-acetophenones, α-hydroxy-alkyl-phenones, α-amino-alkyl-phenones, acylphosphine oxides, phenyl ketocoumarins, camphorquinones, silane and derivatives thereof, and maleimides.

9. The polymeric photoinitiator according to claim 1, wherein Pi is a non-cleavable photoinitiator.

10. The polymeric photoinitiator according to claim 1, wherein formula (I) is of general formula (Va):

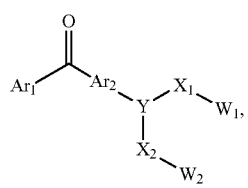

(Va)

wherein Ar$_1$ and Ar$_2$ are independently selected from the same or a different aryl, where Y may be present at any position on Ar$_2$, and where each aryl independently may be optionally substituted with one or more substituents selected from the —F, —Cl, —Br, —I, —CN, —$NO_2$, —$C_1$-$C_6$ alkyl, aryl, —O—($C_1$-$C_6$ alkyl), —C(O)—O—($C_1$-$C_6$ alkyl), —S—($C_1$-$C_6$ alkyl), —S(O)—($C_1$-$C_6$ alkyl), —$SO_2$—($C_1$-$C_6$ alkyl), —NH—C(O)—($C_1$-$C_6$ alkyl), —C(O)—NH—($C_1$-$C_6$ alkyl), and —C(O)—$NH_2$.

11. The polymeric photoinitiator according to claim 10, wherein Ar$_1$ and Ar$_2$ each independently are an optionally substituted phenyl and where Y may be attached at any position on Ar$_2$.

12. The polymeric photoinitiator according to claim 10, wherein Y is present at the para-position on Ar$_2$.

13. The polymeric photoinitiator according to claim 1, wherein formula (I) is of the general formula (Vb):

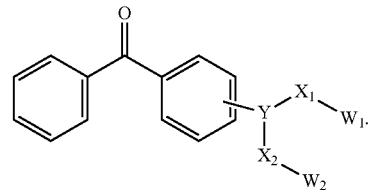

(Vb)

14. The polymeric photoinitiator according to claim 1, wherein formula (I) is of general formula (Vc):

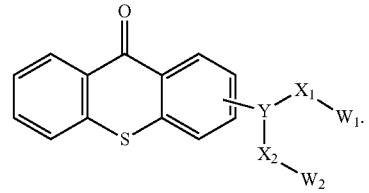

(Vc)

15. The polymeric photoinitiator according to claim 1, wherein formula (I) is of general formula (Vd):

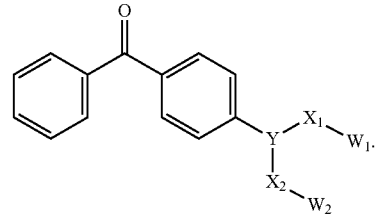

(Vd)

16. The polymeric photoinitiator according to claim 1, wherein the photoinitiator monomer A is
  2-(4-benzoylphenoxymethyl)-2-[(dimethylamino)methyl]propane-1,3-diol;
  1-chloro-4-{2-[(dimethylamino)methyl]-3-hydroxy-2-(hydroxylmethyl)propoxy}-9H-thioxanthen-9-one;
  2-[3-(4-benzoylphenoxy)propyl]-2-[(dimethylamino)methyl]propane-1,3-diol;
  2-[3-(4-benzoylphenoxy)propyl]-2-(dimethylamino)propane-1,3-diol; or
  (4-{[3-(dimethylamino)-1,4-dihydroxybutan-2-yl]oxy}phenyl)(phenyl)methanone.

17. The polymeric photoinitiator according to claim 1, wherein Q is selected from the group consisting of an optionally substituted $C_1$-$C_{12}$ alkylene, an optionally substituted $C_2$-$C_{12}$ alkenylene, an optionally substituted $C_3$-$C_8$ cycloalkyl, an optionally substituted $C_3$-$C_{12}$ heterocyclyl, an optionally substituted aryl and an optionally substituted biaryl.

18. The polymeric photoinitiator according to claim 1, wherein $W_3$ and $W_4$ are each independently selected from isocyanate and thioisocyanate groups.

19. The polymeric photoinitiator according to claim 1, wherein $W_3$ and $W_4$ are the same functional groups.

20. The polymeric photoinitiator according to claim 1, wherein monomer (B) is selected from the group consisting of: 1,4-phenylene diisocyanate (PPDI), toluene diisocyanate (TDI), methylene diphenyl diisocyanate (MDI), 1,5-naphthalene diisocyanate (NDI), 3,3'-bitolylene-4,4'-diisocyanate (TODI), 1,3-xylylenediisocyanate (XDI), tetramethyl-m-xylidene diisocyanate (TMXDI), 1,6-hexamethylene diisocyanate (HDI), isophorone diisocyanate (IPDI), bis(4-isocyanatocyclohexyl)methane (HMDI), 2,2,5-trimethylhexane diisocyanate (TMHDI), 1,4-cyclohexane diisocyanate (CHDI), and 1,3-bis(isocyanato-methyl)cyclohexane (HXDI).

21. The polymeric photoinitiator according to claim 1, wherein in the co-polymerization of monomers (A) and (B), $W_1$ reacts with $W_3$ to form a urethane, thiourethane, urea, thiourea, ester or amide moiety, and $W_2$ reacts with $W_4$ to form a urethane, thiourethane, urea, thiourea, ester or amide moiety.

22. The polymeric photoinitiator according to claim 1, wherein in the co-polymerization of monomers (A) and (B), $W_1$ reacts with $W_3$ to form a urethane, or thiourethane moiety, and $W_2$ reacts with $W_4$ to form a urethane or thiourethane moiety.

23. The polymeric photoinitiator according to claim 1, wherein both $W_1$ and $W_2$ are alcohol functional groups and both $W_3$ and $W_4$ are isocyanate functional groups.

24. The polymeric photoinitiator according to claim 1, further comprising one or more additional monomers (C), comprising formula (VII):

$$W_5\text{-}T\text{-}W_6 \quad (VII)$$

T is selected from the group consisting of an optionally substituted $C_1$-$C_{12}$ alkylene, an optionally substituted $C_1$-$C_{12}$ alkenylene, an optionally substituted $C_3$-$C_8$ cycloalkyl, an optionally substituted $C_3$-$C_{12}$ heterocyclyl, an optionally substituted aryl, an optionally substituted biaryl, a —[O—($C_1$-$C_{12}$ alkylene)]$_m$-, a —[S—($C_1$-$C_{12}$ alkylene)]$_m$-, where m is an integer from 1-1000, and combinations thereof;

$W_5$ and $W_6$ each independently selected from —OH, —CH$_2$OH, —NH$_2$, —NHR$^{13}$, —SH, —Si(OR$^{13}$)$_2$—H, —C(=O)—OSi(R$^{13}$)$_3$, —NCO, —NCS, —COOH, —COOR$^{13}$, —COO-aryl, —C(=O)—Cl, —O—C(=O)—Cl, —C(O)—NH$_2$, —C(O)—NHR$^{12}$, —NH—C(O)—OR$^{12}$, and —OC(O)—NHR$^{12}$, wherein R$^{12}$ is H or $C_1$-$C_6$ alkyl, R$^{13}$ is $C_1$-$C_6$ alkyl; and wherein $W_5$ and $W_6$ are selected such $W_5$ reacts with $W_1$ or $W_3$ to form a urethane, thiourethane, urea, thiourea, ester, ether, amide, carbonate, allophanate or biuret moiety, and $W_6$ reacts with $W_2$ or $W_4$ to form a urethane, thiourethane, urea, thiourea, ester, ether, amide, carbonate, allophanate or biuret moiety.

25. The polymeric photoinitiator according to claim 24, wherein $W_5$ and $W_6$ are each independently selected from —OH, —CH$_2$OH, —NH$_2$, —NHR$^{13}$, and —SH.

26. The polymeric photoinitiator according to any claim 24, wherein $W_5$ and $W_6$ are the same functional groups.

27. The polymeric photoinitiator according to claim 24, wherein monomer (C) is selected from the group consisting of: polyethylene glycol (PEG), polypropylene glycol (PPG), random and block poly(ethylene glycol)-poly(propylene glycol) copolymers, poly(tetramethylene glycol) (PTMG), poly (1,4-butanediol adipate), poly(ethanediol 1,4-butanediol adipate), poly(caprolacton) diol, poly(1,6-hexanediol carbonate) and poly(ethylene terephthalate) diol.

28. The polymeric photoinitiator according to claim 1, wherein the weight ratio of monomers (A):(B) is 1:99-99:1.

29. The polymeric photoinitiator according to claim 24, wherein the weight ratio of monomers (A):(C) is 1:99-99:1.

30. A polyacrylate obtained by radical polymerization of at least one acrylate monomer (Ac) in the presence of a polymeric photoinitiator, said polymeric photoinitiator being a co-polymer of at least one monomer (A) with at least one monomer (B), wherein:

monomer (A) is a photoinitiator comprising formula (I):

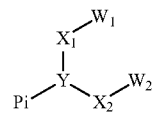

(I)

as defined in claim 1; and monomer (B) is as defined in claim 1;

wherein $W_1$ reacts with $W_3$ to form a urethane, thiourethane, urea, thiourea, ester or amide moiety, and $W_2$ reacts with $W_4$ to form a urethane, thiourethane, urea, thiourea, ester or amide moiety.

31. The polyacrylate according to claim 30, wherein the polymeric photoinitiator is as defined in claim 24.

32. The polyacrylate according to claim 30, wherein the acrylate monomer (Ac) is a mono-, di- or tri-acrylate.

33. The polyacrylate according to claim 30, wherein the acrylate monomer (Ac) is an acrylate ester of the formula (VIII):

$$(R^{14})(R^{15})C=C(R^{16})-C(=O)-O-R^{17} \quad (VIII)$$

wherein R$^{14}$, R$^{15}$ and R$^{16}$ are each independently selected from the group consisting of H, an optionally substituted $C_1$-$C_{12}$ alkyl, an optionally substituted $C_1$-$C_{12}$ alkenyl, an optionally substituted $C_3$-$C_{12}$ heterocyclyl, and an optionally substituted aryl, and R$^{17}$ is selected from the group consisting of an optionally substituted $C_1$-$C_{12}$ alkyl, an optionally substituted $C_1$-$C_{12}$ alkenyl, an optionally substituted $C_3$-$C_{12}$ heterocyclyl, and an optionally substituted aryl.

34. A photoinitiator monomer of Formula (I):

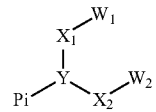

(I)

wherein:
Pi is a photoinitiator moiety;
Y is:

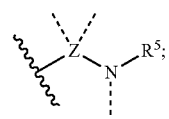

(II)

Z is a linker moiety selected from an optionally substituted —O—($C_1$-$C_{12}$ alkylene)-, an optionally substituted —S—($C_1$-$C_{12}$ alkylene)-, and an optionally substituted —$NR^2$—($C_1$-$C_{12}$ alkylene)-;

—$X_1$—$W_1$ and —$X_2$—$W_2$ are each independently attached to Y via the Z-linker;

—$X_1$—$W_1$ and —$X_2$—$W_2$ may be attached to the Z-linker wherever it is chemically feasible, corresponding to formula (IIa):

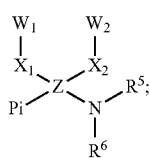

(IIa)

$R^2$ is an optionally substituted $C_1$-$C_{12}$ alkyl;

$X_1$ and $X_2$ are each independently selected from a single bond, an optionally substituted $C_1$-$C_{12}$ alkylene, an optionally substituted $C_2$-$C_{12}$ alkenylene, —O—, —S—, —$NR^4$—, —C(=O)—, —C(=$NR^3$)—, —Si($R^3$)$_2$—O—, an optionally substituted $C_3$-$C_8$ cycloalkyl, an optionally substituted heterocyclyl, an optionally substituted aryl, and combinations thereof;

Z is selected such that N is a tertiary amine;

$R^3$ is H or an optionally substituted $C_1$-$C_{12}$ alkyl;

$R^4$ is an optionally substituted $C_1$-$C_{12}$ alkyl;

$R^5$ and $R^6$ are each independently selected from an optionally substituted $C_1$-$C_6$ alkyl, wherein the carbon atom adjacent to the N-atom is in a —$CH_2$— moiety;

$W_1$ and $W_2$ are each independently selected from —OH, —$CH_2OH$, —$NH_2$, —$NHR^8$, —SH, —NCO, —NCS, and —COOH;

$R^8$ is a $C_1$-$C_6$ alkyl; and any optional substituents are selected from —F, —Cl, —Br, —I, —CN, —$NO_2$, —$C_1$-$C_6$ alkyl, aryl, —O—($C_1$-$C_6$ alkyl), —C(O)—O—($C_1$-$C_6$ alkyl), —S—($C_1$-$C_6$ alkyl), —S(O)—($C_1$-$C_6$ alkyl), —$SO_2$—($C_1$-$C_6$ alkyl), —NH—C(O)—($C_1$-$C_6$ alkyl), —C(O)—NH—($C_1$-$C_6$ alkyl), and —C(O)—$NH_2$.

35. A method for producing a polymeric photoinitiator, said method comprising step-growth co-polymerization of at least one monomer (A) with at least one monomer (B), wherein (A) and (B) comprise the formulae defined in claim 1.

36. The method according to claim 35, wherein the co-polymerization reaction additionally comprises one or more additional monomers (C), comprising the formula defined in claim 24.

37. A method of cross-linking the polymeric photoinitiator as defined in claim 1, said method comprising exposing the polymeric photoinitiator to UV radiation and/or heat.

38. A method for producing a polyacrylate, said method comprising the steps of:
  a) combining one or more acrylate monomers with a polymeric photoinitiator to form a mixture, said polymeric photoinitiator being as defined in claim 1; and
  b) subjecting the mixture from step a) to UV radiation and/or heat.

* * * * *